(12) United States Patent
Pettegrew et al.

(10) Patent No.: US 7,407,778 B2
(45) Date of Patent: Aug. 5, 2008

(54) COMPOUNDS, COMPOSITIONS AND METHODS FOR TREATING NEUROPSYCHIATRIC DISORDERS

(76) Inventors: Jay W. Pettegrew, 630 S. Linden Ave., Pittsburgh, PA (US) 15208; Samuel Gershon, 1981 Squaw Run Rd., Fox Chapel, PA (US) 15238; Kanagasabai Panchalingam, 1214 Holy Cross Dr., Monroeville, PA (US) 15146

(*) Notice: Subject to any disclaimer, the term of this patent is extended or adjusted under 35 U.S.C. 154(b) by 0 days.

(21) Appl. No.: 11/198,761

(22) Filed: Aug. 5, 2005

(65) Prior Publication Data
US 2006/0088614 A1 Apr. 27, 2006

Related U.S. Application Data

(63) Continuation-in-part of application No. 11/117,126, filed on Apr. 25, 2005, which is a continuation-in-part of application No. 10/359,560, filed on Feb. 7, 2003.

(60) Provisional application No. 60/354,323, filed on Feb. 7, 2002.

(51) Int. Cl.
- C12P 21/04 (2006.01)
- A61K 35/78 (2006.01)
- A61K 31/225 (2006.01)
- A01B 79/00 (2006.01)
- A01N 37/30 (2006.01)

(52) U.S. Cl. .................. 435/70.1; 47/58.1; 424/195.1; 514/548; 514/556

(58) Field of Classification Search ............... 435/70.1; 424/195.1; 47/58.1; 514/546, 556
See application file for complete search history.

(56) References Cited

U.S. PATENT DOCUMENTS

| | | | |
|---|---|---|---|
| 329,638 A | 11/1885 | Frank | |
| 394,841 A | 12/1888 | Duisberg | |
| 401,024 A | 9/1889 | Frank | |
| 622,961 A | 4/1899 | Levinstein | |
| 1,979,534 A | 11/1934 | Ebert | |
| 4,221,869 A | 9/1980 | Vandecasteele | |
| 4,346,107 A * | 8/1982 | Cavazza et al. ............. | 514/547 |
| 4,542,098 A | 9/1985 | Vandecasteele | |
| 4,642,290 A | 2/1987 | Sih | |
| 4,650,759 A | 3/1987 | Yokozeki | |
| 4,708,936 A | 11/1987 | Kulla | |
| 4,743,621 A | 5/1988 | Cavazza | |
| 4,933,156 A | 6/1990 | Quay | |
| 4,965,364 A | 10/1990 | Marko | |
| 4,996,041 A | 2/1991 | Arai | |
| 5,008,099 A | 4/1991 | Quay | |
| 5,028,538 A | 7/1991 | Seim | |
| 5,039,511 A | 8/1991 | Quay | |
| 5,066,583 A | 11/1991 | Mueller | |
| 5,156,966 A | 10/1992 | Takahashi | |
| 5,187,093 A | 2/1993 | Kulla | |
| 5,208,037 A * | 5/1993 | Wright et al. ............... | 424/473 |
| 5,231,000 A | 7/1993 | Majocha | |
| 5,276,059 A | 1/1994 | Caughey | |
| 5,358,712 A | 10/1994 | Efange | |
| 5,545,566 A | 8/1996 | Growden | |
| 5,631,168 A | 5/1997 | Growdon | |
| 5,668,117 A | 9/1997 | Shapiro | |
| 5,773,024 A | 6/1998 | Unger | |
| 5,837,219 A | 11/1998 | Watanabe | |
| 5,846,517 A | 12/1998 | Unger | |
| 5,853,985 A | 12/1998 | Salbaum | |
| 5,866,427 A | 2/1999 | Mendelson | |
| 5,879,884 A * | 3/1999 | Peroutka ........................ | 435/6 |
| 5,889,055 A | 3/1999 | Howard | |
| 5,973,004 A | 10/1999 | Howard | |
| 5,976,816 A | 11/1999 | Alkon | |
| 6,037,373 A | 3/2000 | De Simone | |

(Continued)

FOREIGN PATENT DOCUMENTS

WO   WO9409371   4/1994

(Continued)

OTHER PUBLICATIONS (V) Pettegrew et al. (II), "Acetylk-L-Carnitine Physical-Chemical, Metabolic, and Therapeutic Properties: Relevance for its Mode of Action in Alzheimer's Disease and Geriatric Depression," Molecular Psychiatry, 5(6), 616-632 (2000).*

(Continued)

*Primary Examiner*—Patrick T. Lewis
*Assistant Examiner*—L. E. Crane
(74) *Attorney, Agent, or Firm*—Lesavich High-Tech Law Group, P.C.; Stephen Lesavich

(57) ABSTRACT

Acetyl-L-carnitine (ALCAR) and L-carntine (LCAR) are nutraceuticals with indications in treating a variety of mental health disorders. A metabolomics-guided bioprocess method is presented to enhance aLCAR and LCAR formation in germinating plant seeds. Metabolic fluxes are manipulated by germination in bioreactors to increase oxygen availability as well as provide an aseptic environment to alter carbohydrate consumption and feedback repress gluconeogenesis. Large shifts in sunflower seed fatty acid, phospholipid and high-energy metabolism change the germination environment and these metabolic changes lead to an approximate 1000-fold increase in natural LCAR and ALCAR production by the seeds. The resulting LCAR and ALCAR products from the seeds are used for treating mental health disorders including Alzheimer's disease, geriatric depression, non-geriatric depression and schizophrenia.

6 Claims, 24 Drawing Sheets

U.S. PATENT DOCUMENTS

| | | | |
|---|---|---|---|
| 6,066,664 A | 5/2000 | Cavazza |
| 6,071,494 A | 6/2000 | Unger |
| 6,080,582 A | 6/2000 | Alkon |
| 6,107,050 A | 8/2000 | Alkon |
| 6,114,175 A | 9/2000 | Kiunk |
| 6,133,259 A | 10/2000 | Kiunk |
| 6,139,819 A | 10/2000 | Unger |
| 6,166,077 A | 12/2000 | De Simone |
| 6,168,776 B1 | 1/2001 | Klunk |
| 6,175,061 B1 | 1/2001 | Bright |
| 6,183,777 B1 | 2/2001 | Chen |
| 6,231,834 B1 | 5/2001 | Unger |
| 6,255,057 B1 | 7/2001 | Gordon |
| 6,300,085 B1 | 10/2001 | Alkon |
| 6,313,159 B1 | 11/2001 | Jackson |
| 6,335,021 B1 | 1/2002 | Cavazza |
| 6,337,197 B2 | 1/2002 | Elssner |
| 6,346,282 B1 | 2/2002 | Cavazza |
| 6,348,464 B1 | 2/2002 | Jackson |
| 6,379,936 B1 | 4/2002 | Elssner |
| 6,380,244 B2 | 4/2002 | Martin |
| 6,380,252 B1 | 4/2002 | De Simone |
| 6,403,056 B1 | 6/2002 | Unger |
| 6,416,740 B1 | 7/2002 | Unger |
| 6,417,178 B1 | 7/2002 | Klunk |
| 6,420,599 B2 | 7/2002 | Marzi |
| 6,479,034 B1 | 11/2002 | Unger |
| 6,521,211 B1 | 2/2003 | Unger |
| 6,548,047 B1 | 4/2003 | Unger |
| 6,551,576 B1 | 4/2003 | Unger |
| 6,576,220 B2 | 6/2003 | Unger |
| 6,589,547 B1 | 7/2003 | Igari |
| 6,589,948 B1 | 7/2003 | Malfroy-Camine |
| 6,653,112 B2 | 11/2003 | Kleber |
| 6,708,053 B1 | 3/2004 | Brooks |
| 6,716,412 B2 | 4/2004 | Unger |
| 6,808,720 B2 | 10/2004 | Unger |

FOREIGN PATENT DOCUMENTS

| | | |
|---|---|---|
| WO | WO99/66914 A2 | 12/1999 |
| WO | WO9966914 | 12/1999 |
| WO | WO03066041 | 8/2003 |
| WO | WO2004054567 | 7/2004 |

OTHER PUBLICATIONS (W) Garzya et al., "Evaluation of the Effects of L-Acetylcarnitine on Senile Patients Suffering from Depression," Drugs Under Experimental and Clinical Research, 16(2), 101-106 (1990).*

[R] Pettegrew et al. (I), "31P-MRS Study of Acetyl-L-Carnitine Treatment in Geriatric Depression: Preliminary Results," Bipolar Disorders, 4(1), 61-66 (Feb. 2002).*

(S) Fulgente et al., "Laevo-Acetylcarnitine (Nicetile®) Treatment of Senile Depression," /Clinical Trials Journal, 27(3), 155-163 (1990).*

(T) Casella et al., "L-Acetylcarnitine in Depressed Elderly Subjects. A Cross-Over Study vs. Placebo," Drugs Under Experimental and Clinical Research, 13(7), 417-423 (1987).*

(U) Bella et al., "Effect of Acetyl-L-Carnitine on Geriatric Patients Suffering From Dysthymic Disorders," Int. J. Clinical Pharmacology Research, 10(6), 355-360 (1990).*

(X) Alpha-GPC ((L-Alpha glycerylphosphorylcholine, Choline alfoscerate), on-line information published by Global Information Hub on Integrated Medicine, 2003: web address; <www.nhiondemand.com>.*

(Y) O'Neil et al. (eds.), The Merck Index, An Encyclopedia of Chemicals, Drugs, and Biologicals, 13th Edition, 2001, Merck & Co., Whitehouse Station, NJ, only pp. 16 and 312 supplied, see entry 86 (acetylcarnitine) and 1862 (carnitine).*

Asplund, P.T. (2001): "Intrinsic Oxygen use Kinetics of Transformed Plant Root Culture" Biotechnology Progress, vol. 17 No. 3 pp. 481-489.

Balasaraswathi, R et al (1997): "Changes in oil, sugars, and nitrogenous components during germination of sunflower seeds, Helianthus annuus" Plant Foods for Human Nutrition, vol. 51, No. 1, pp. 71-77.

Cabot et al.: "Vasopressin, phorbol diesters and serum elicit choline glycerophospholipid hydrolysis and diacyiglycerol formation in nontransformed cells: transformed derivatives do not respond" Biochimica et Biophysica Acta, vol. 959, 1988, pp. 46-57.

De Simone C et al.(1998): "Amerlioration of the depression of HIV-infected subjects with L acetyl carnitine therapy" Journal of Drug Development vol. 1, No. 3, pp. 163-166.

Eastmond, P. et al (2001):"Re-examining the Role of the Glyoxylate Cylce in Oilseeds" Trends in Plant Science, vol. 6. No. 2 pp. 72-77.

Eckardt, N. (2005): "Peroxisomal Citrate Synthase Provides Exit Route from Fatty Acid Metabolism in Oilseeds" Plant Cell vol. 17, No. 7. pp. 1863-1865.

Gürel, E., and K. Kazan (1998): "Development and efficient plant regeneration system in sunflower (Helianthus annus L.)" Tr. J. of Botany, vol. 22, pp. 381-387.

Kanfer, N; W. Pettegrew, Moossy and D.G. McCartney (1993): "Alterations of Selected Enzymes of Phospholipid Metabolism in Alzheimer's Disease Brain Tissue as Compared to Non-Alzheimer's Demented Controls," Neurochemical Research, v.18, N.3, pp. 33 1-334.

Klunk, W.; Chong-Jun Xu, Richard McClure, Kanagasavai Panchalinigam, Jeff Stanley and Jay Pettegrew (1997): "Aggregation of B-Amyloid Peptide Is Promoted by Membrane Phospholipid Metabolites Elevated in Alzheimer's Disease Brain ," Journal of Neurochemistiy, v. 69, n. 1, pp. 266-272.

Lacey, Jeffery C and Leslie M. Loew (1983): "Phospholipid Synthesis Based on New Sequential Phosphate and Carboxylate Ester Bond Formation Steps," J. Org. Chem. v. 48, pp. 5214-5221.

Le Page-Degivry M-T et al (1990): "Involvment of endogenous abscisic acid in onset and release of helianthus-annuus embryo dormancy" Plant Physiology, vol. 92 No. 4, pp. 1164-1168.

Mandal, Pravat K; Richard J. McClure and Jay W. Pettegrew, (2004): "Interactions of A3(1-40) with Glycerophosphocholine and Intact Erythrocyte Membranes: Fluorescence and Circular Dichroism Studies," Neurochemical Research, 29 pages 2273-2279.

McClure, RJ.; K. Panchanlingam, J. A. Stanely and J.W. Pettegrew (2001): "Molecualr Modeling of Glycerophosphocholine with an Axnyloid Beta(I-28) Peptide Fragment," Society of Neuroscience Abstracts, 27: 322.9, 2001.

Meiboom, S.(1961): "Nuclear Magnetic Resonance Study of the Proton Transfer in Water," The Journal of Chemical Physics, v.34,n. 2,pp. 375-388.

Meiboom, S; Z. Luz, and D. Gill (1957): "Proton Relaxation in Water," The Journal of Chemical Physics, v. 27, n.6, pp. 1411-1412.

Mushika et al.(1971): "A New Phosphorylating Reagent. V. The Preparation of alpha-Glycerophosphoryl Choline and its Analogues by Means of 2-Chloromethyl-4-nitrophenyl Phosphorodichloridate" Chem. Pharm. Bull.,vol. 19, No. 4.

Nasca D et al (1989): "Action of acetyl-L-carnitine in association with mianserine on depressed old people" New trends in clinical neuropharmacology. Italy. vol. 3, No. 4, pp. 225-230.

Nifant'ev et al.(1978): "Synthesis of lipids and their models from glycerol alkylene phosphites. II. Phosphatidylcholines and their analogs" J. Org. Chem. USSR, vol. 14, pp. 56-63.

Ohkatsu et al.(1998): "Synthesis and polymerization of a macromonomer derived from phosphatidicholine" Makromol. Chem., vol. 189, pp. 755-760.

Pettegrew, J.W.; P.K. Mandal, R.J. McClure and K. Panchanlingam (2003): "Glycerophosphocholine promotes aggregation of A-peptide: evidence from fluorescence, circular dichorism, and multidimensional NMR studies," University of Pittsburgh Publication, program No. 944.2.

Pettegrew, J; Kanagasabai Panchalingam, Ronald Hamilton and Richard McClure (2001): "Brain Membrane Phospholipid Alterations in Alzheimer's Disease," Neurochemical Research, v.26, n.7, pp. 771-782.

Pettegrew, JW; E. Klunk, K. Panchalingam, R.J. VcClure and 3. A. Stanely (2000): "Molecular insights into neurodevelopmental and neurodegenerative diseases," Brain Research Bulletin, v.53, n.4, pp. 455-469.

Scuccimarra A et al.(1998): "La L-Acetilcarnitina neele sindromi dpressive di Ogni Eta L-acetylcarnitine in depressive syndromes for all ages" Gazzetta Medica Italiana, Minerva Medica. Torino, IT, vol. 147, No. 6,pp. 213-214.

Spanner et al.(1987): "The Hydrolysis of Glycerophosphocholine by Rat Brain Microsomes: Activation and Inhibition" Neurochemical Research, vol. 12, No. 2, pp. 203-206.

Sweet et al.(2002): "Psychosis in Alzheimer disease: postmortem magnetic resonance spectroscopy evidence of excess neuronal and membrane phospholipid pathology" Neurobiology of Aging, vol. 23, 2002, pp. 547-553.

Volz et al(1983): "31P magnetic resonance spectroscopy in the frontal lobe of major depressed patients" European Archives of Psychiatry and Clinical Neuroscience. vol. 248, No. 6. December pp. 289-295.

Yanker, B; Lawrence Duffy and Daniel Kirschner (1990): "Neurotrophic and neurotoxic effects of amyloid beta protein: reversal by tachykinin neuropeptides," Science, v.250, n.4978, pp. 279-283.

Yildiz A et al (2001): "P.nuclear magnetic resonance spectroscopy findings in bipolar illness: A meta-analysis" Psychiatry Research-Neuroimaging. vol. 106, No. 3, May 30, 2001, pp. 181-191.

International Search Report PCT/US2004/016,750.

International Search Report PCT/US2006/016,095.

Lepage-Degivry M-T et al.; "Involvement of Endogenous Abscisic Acid in Onset and Release of Helianthus-Annus Embryo Dormancy" Plant Physiology (Rockville), vol. 92, No. 4, 1990, pp. 1164-1168, XP002411901.

Gurel, E and Kazan K; "Development and efficient plant regeneration system in sunflower (Helianthus annus L.)" TR. J. Botany, vol. 22, 1998, pp. 381-387, XP002411902.

Balasaraswathi R et al.; "Changes in oil, sugars and nitrogenous components during germination of sunflower seeds, Hellanthus annus" Plant Foods for Human Nutition (Dordrecht) vol. 51, No. 1, 1997, pp. 71-77, XP002411903.

Eastmond Peter J et al.; "Re-examining the role of glyoxylate cycle in oilseeds" Trends in Plant Science, Elsevier Science. Oxford, GB, vol. 6, No. 2, Feb. 2001, pp. 72-77, XP00236781.

Eckardt Nancy A.; "Peroxisomal citrate synthase provides exit route from fatty acid metabolism in oilseeds" Plant Cell, vol. 17, No. 1, Jul. 2005, pp. 1863-1865, XP002411904.

Asplund Patrick T et al.;"Intrinsic oxygen use kinetics of transformed plant root culture" Biotechnology Progress, vol. 17, No. 3, May 2001, pp. 481-489. XP 0023411905.

Partial PCT Search Report PCT/2006/030,717, mailed Jan. 22, 2007.

* cited by examiner

FIG. 1A
FIG. 1B
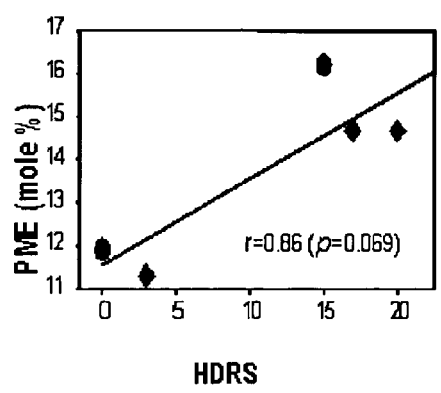
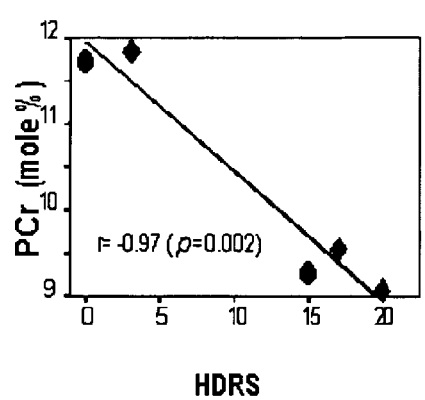

Entry

12 Weeks

Entry

12 Weeks

126

COMPOUNDS, COMPOSITIONS AND METHODS FOR TREATING NEUROPSYCHIATRIC DISORDERS

CROSS REFERENCES TO RELATED APPLICATIONS

This application is a Continuation-In-Part (CIP) of U.S. application Ser. No. 11/117,126, filed Apr. 27, 2005, which is a CIP of Ser. No. 10/359,560, filed Feb. 7, 2003, which claims priority to U.S. Provisional application No. 60/354,323, filed Feb. 7, 2002, contents of all of which are incorporated by reference.

FIELD OF THE INVENTION

The present invention relates to compounds, compositions and methods for synthesis and use adapted for treating neuropsychiatric disorders, generally, and of Alzheimer's disease, geriatric depression, non-geriatric depression and schizophrenia specifically.

BACKGROUND OF THE INVENTION

The clinical response to antidepressant treatment in later life follows a variable temporal response, with a median time to remission of 12 weeks. Newer antidepressants still demonstrate a disturbing side-effect profile in this fragile patient population. Thus, there is a need for the development of newer antidepressants. One such candidate is acetyl-L-carnitine (ALCAR), a molecule that is naturally present in human brain demonstrating only few side effects.

Seven parallel, double-blind, placebo-controlled studies have examined ALCAR efficacy in various forms of geriatric depression. Phosphorus magnetic resonance spectroscopy ($^{31}$P MRS) directly provides information on membrane phospholipid and high-energy phosphate metabolism in defined, localized brain regions. Although in vivo $^{31}$P MRS studies in major depression are limited, there is evidence of altered high-energy phosphate and membrane phospholipid metabolism in the prefrontal and basal ganglia regions. Increased levels of precursors of membrane phospholipids [i.e., increased phosphomonoesters (PME) levels] in the frontal lobe of major depressed subjects compared to controls was reported. Other researchers also observed higher PME levels in bipolar subjects in their depressive phase compared with the euthymic state. In terms of high-energy phosphates, reduced levels of adenosine triphosphate (ATP) have been observed in both the frontal and basal ganglia of major depressed subjects. The level of the high-energy phosphate buffer, phosphocreatine (PCr), was lower in severely depressed subjects compared with mildly depressed subjects. Accordingly, the relationship between membrane phospholipid and high-energy phosphate metabolism as assessments of beneficial results in the treatment of depression are recognized.

Epidemiology of Depressive Disorders

Depressive disorders (i.e., major depression, dysthymia, bipolar disorder) are among the most common and disabling medical conditions throughout the world. For example, about 9.5% of the US adult population will suffer from a form of depression during any given year which is approximately 18.8 million people. In addition, 16-18% of women and 10% of men (3-4 million) will experience some form of depression. The lifetime risk for depression is approximately 15-20% regardless of gender.

When one episode of depression is experienced, there is a 50% likelihood of recurrent episodes. When a second episode of depression occurs, there is a 80-90% likelihood of recurrent episodes and 75% of depressive disorders are recurrent.

It is estimated 20% of depressed individuals will attempt suicide and 6% will be successful. 75% of those committing suicide have a depressive disorder. The rate of successful suicide is four times greater in men.

About 10% of people with depression also will experience episodes of mania. Bipolar depressive episodes usually last longer, have a greater likelihood of psychotic features, and convey a greater risk of suicide. Bipolar disorder may be misdiagnosed as depression resulting in inappropriate treatment that may worsen the disease progression and outcome.

Depression is a acotraveler with a number of other medical and psychiatric conditions and numerous medications can cause depressive symptoms.

The prevailing dogma concerning the pathophysiology of depressive disorders (major depression, dysthymia, bipolar disorder) is that of an altered neurotransmitter receptor and many studies have been conducted to find such an alteration. To date, there has been no demonstration of an alteration in the binding site for any of the targeted neurotransmitters. Another problem with the altered neurotransmitters receptor dogma is that although the tricyclic antidepressants and selective neurotransmitter reuptake inhibitor drugs quickly enter brain and bind to their targeted sites, the clinical therapeutic effect does not occur for 4-6 weeks even though the onset of side effects is immediate.

Studies by Samuel Gershon over the years, since early 1950, have questioned the concepts of the established modes of action of antidepressants and those of the etiology of affective disorders.

In the early 50's a number of papers appeared suggesting that lithium not only had anti-manic properties but that it also exhibited anti-depressant and prophylactic activity in depression. These observations were confirmed by the controlled studies carried out by Schou et al. in Denmark and Prien et al. in Australia. This tended to indicate that perhaps a single neurotransmitter and a single receptor site would not qualify as the full explanation of their effects. In 1961, Gershon published a report in the Lancet on the psychiatric sequelae of organo-phosphorus insecticides in an exposed human population. Thus a role for acetylcholine in contributing to the production of major depressive disorder (MDD) was presented. This added to the complexity of current theories. In the 1970's an antidepressant Ludiomil was marketed with the effect of being a specific norepinephrine (NE) uptake inhibitor and thus exerting its effect by this route. This was an effective agent and was taken off the market because of other adverse effects (AE). In 1970 Gershon and colleagues carried out a number of experiments with synthesis inhibitors in patients undergoing treatment with different antidepressants and showed that only the inhibition of serotonin synthesis and not NE synthesis interfered with antidepressant outcomes.

These experiments demonstrated that a single transmitter or a single receptor could not account for therapeutic activity and clearly suggested other mechanisms are involved relating to membrane effects and second messenger systems. Antidepressant use has now clearly been associated with treatment emergent mania and the induction of rapid cycling in affective disorder patients (Tamada et al., 2004).

In addition to the concerns that have been established with the more classic bipolar I (BPI) type, much controversy surrounds the use of antidepressants in bipolar II (BPII) depression, a growing population.

Antidepressant induced cycle acceleration has been reported to be more likely in BPII patients than in BPI (Altshuler et al., 1995; Joffe et al., 2002; Benazzi, 1997; Henry et al., 2001; Ramasubbu, 2001).

The data has increasingly shown the need for the use of effective antidepressants but at the same time has produced data indicating the need for caution with the agents available. These effective antidepressants cause both the risk of switch into mania and the even more serious effect of rapid cycling of the affective disorder and an alteration of the frequency and severity of episodes.

A different conceptual approach has been the subject of almost 3 decades of research by Jay W. Pettegrew. This concept is that there is nothing structurally wrong with neurotransmitter receptors, but the receptors are in a membrane environment that has altered molecular structure and dynamics. It is these membrane alterations that alter the functional dynamics of neurotransmitter receptors which in turn alters their physiological function. Dr. Pettegrew was one of the first to demonstrate alterations in membrane molecular dynamics in living cells obtained from patients with neuropsychiatric disorders. Alterations were similarly demonstrated in cells obtained from patients with depression (Pettegrew et al., 1979c; Pettegrew et al., 1980a; Pettegrew et al., 1981a; Pettegrew et al., 198; Pettegrew et al., 1979b; Pettegrew et al., 1980b; Pettegrew et al., 1981b; Pettegrew et al., 1982b; Pettegrew et al., 1987b; Pettegrew et al., 1993b; Pettegrew et al., 1990c; Pettegrew et al., 1993a; Pettegrew et al., 1990b). Lithium was shown to correct the membrane dynamic alterations observed in depressive patients.

Given the rather striking changes in membrane molecular dynamics, Dr. Pettegrew turned to investigate alterations in membrane metabolism (Pettegrew et al., 1978; Pettegrew and Minshew, 1981; Pettegrew et al., 1982a; Glonek et al., 1982a) (Pettegrew et al., 1979a; Glonek et al., 1982b; Cohen et al., 1984; Pettegrew et al., 1986; Pettegrew et al., 1987a; Pettegrew et al., 1988a; Pettegrew et al., 1988b; Pettegrew et al., 1990a; Pettegrew et al., 1991; Keshavan et al., 1991; Kanfer et al., 1993; Pettegrew et al., 1994; Singh et al., 1994; Pettegrew et al., 1995; Klunk et al., 1996; Geddes et al., 1997; Klunk et al., 1998; Pettegrew et al., 2001; Keshavan et al., 2003; Sweet et al., 2002) and again significant alterations were observed in several neuro-psychiatric disorders including major depressive disorder (Pettegrew et al., 2002). Again, lithium was shown to correct the alteration in membrane metabolism observed in patients with depression.

Concerns About Current Classes of Antidepressants in Depressive Disorders

Concerns have been accumulating on the widespread use of all the current classes of antidepressants. This is reflected in the recently published North American based treatment guidelines (Grunze et al., 2002; Hirschfeld et al., 2002); including those of the APA (Sachs et al., 2000). These recommendations have voiced considerable limitations and a conservative attitude to their use, recommending use be restricted to severe bipolar depressions (Goodwin & Jamison, 1990; Murray & Lopez, 1996; Bostwick & Pankratz, 2000). The recommendations go on to suggest that if antidepressants are used they should be withdrawn as early as possible; thus we are now seeing a shift away from both the use of the current classes of antidepressants and recommendations for their long term use since they are associated with the following problems.

1. The risk for induced mania. There is now established a considerable risk of antidepressant induced manic switching and/or rapid cycling. This is seen in both short term and long term exposures. For example with selective reuptake inhibitors (SRIs) clinical samples demonstrate length of switch that are not minimal, that is 15 to 27%. The authors of a number of review articles on this topic suggest that the real rates are around 40% for tricyclic antidepressants (TCAs) and 20% with new SRI antidepressants. Substance abuse has been shown to be a major predictor of antidepressant-induced mania.

2. The risk of suicide in bipolar depressed patients. This risk is in and of itself a significant issue of concern. An analysis of SRIs and other novel antidepressants submitted to the FDA totaling nearly 20 thousand cases showed that there was no significant difference in completed or attempted suicides between patients on antidepressants and placebo treated groups. Simply stated, it appears that antidepressants as a group have not been shown to adequately reduce suicide rates. However, the data on lithium is in contrast to this with a very well established finding of its prophylactic effects against suicidality in a variety of diagnostic categories.

3. Antidepressant efficiency in treating bipolar depression. Prophylactic studies with antidepressants are not robust in the treatment of depressive episodes in bipolar disorders. Again, in contrast, the evidence of efficiency in treating bipolar depression with mood stabilizers is much higher (e.g., lithium and lamotrogine).

4. The potential value of other antidepressant classes. Based on this extensive new information as to the cautions that need to be employed in the use of the standard and SRI antidepressant classes, there is an urgent need for new classes of antidepressant thymoleptics. One such agent, ALCAR has a body of literature that supports the possibility of its therapeutic value in a number of depressive categories.

In view of its unique biochemical effects on the nervous system and its stabilizing effects on membrane functions, ALCAR's antidepressant activity may indeed provide a unique opportunity to address the above-described concerns. Since ALCAR is a natural substance and has been shown to have antidepressant properties without significant side effects and without the potential to induce mania, it is a logical new therapeutic approach.

ALCAR has been shown to have beneficial effects on age-related neurodegenernation and brain energetic stress providing a rationale for its use in Major Depressive Disorder (MDD). In European clinical trials to date, ALCAR has demonstrated antidepressant activity in MDD subjects without significant side effects (Villardita et al., 1983; Tempesta et al., 1987; Nasca et al., 1989; Bella et al., 1990; Fulgente et al., 1990; Garzya et al., 1990).

Overview of Biological Findings in Major Depressive Disorder

MDD has been shown to be associated with changes in: (1) neurotransmitter systems such as serotonin, acetylcholine, and noradrenergic; (2) membranes (e.g., composition, metabolism, biophysical parameters, signal transduction, and ion transport); (3) brain energy metabolism; and (4) brain structure. Computed tomography (CT) and magnetic resonance imaging (MRI) studies in subjects with non-demented, geriatric, major depressive disorder suggest neurodegenerative changes are associated with vascular risk factors (Krishnan, 1993). Beyond brain structural changes, there is evidence from functional neuroimaging studies for molecular, metabolic, and physiologic brain changes suggestive of energetic stress in subjects with MDD. Positron emission tomography (PET) and single photon emission computed tomography (SPECT) studies show a reduced fluorodeoxyglucose metabolic rate (rCMRg) (Buchsbaum et al., 1986) and reduced regional cerebral blood flow (rCBF) (Schlegel et al., 1989) in the basal ganglia and a decrease in rCMRg and rCBF in the frontal lobes of subjects with MDD (Mayberg et al., 1994). Of the neuroimaging methods, $^{31}$P and $^{1}$H magnetic resonance spectroscopic imaging ($^{31}$P-$^{1}$H MRSI) studies provide direct information on membrane phospholipid and high-energy phosphate metabolism ($^{31}$P MRSI) as well as a marker for neuronal structural and metabolic integrity ($^{1}$H MRSI). $^{31}$P and $^{1}$H MRS studies of subjects with MDD indicate alterations in high-energy phosphate and membrane phospholipid metabolism in basal ganglia and prefrontal cortex (Moore et al., 1997a; Charles et al., 1994; Pettegrew et al. 2002).

Neuromorphometric Changes in MDD

Neuroimaging studies have enhanced our understanding of the pathophysiology of MDD. MRI studies provide neuromorphometric correlates of MDD (reviewed by Botteron & Figiel, 1997). MRI studies of third ventricle size in major depression give mixed results; Coffey et al. (1993) report no difference in ventricle size and Rabins et al. (1991) report increased third ventricle size in subjects with MDD compared with controls. Brain MRI subcortical white matter hyperintensities have been reported in the basal ganglia, periventricular region, and frontal lobe of elderly depressed (Coffey et al., 1988; Figiel et al., 1989; Rabins et al., 1991). There have been reports of decreased volumes of the basal ganglia in MDD; Husain et al. (1991) found reduced volume in the putamen, Krishnan et al. (1993) found reduced volume in the caudate, and Dupont et al. (1995) found reduced volume in the caudate, lenticular nucleus, and thalamus. Coffey et al. (1993) report an approximately 7% reduction in bilateral frontal lobe volume in subjects with MDD.

These studies reveal neurodegenerative change in MDD. Other as yet unknown molecular and metabolic factors could predispose to both depression and the neuromorphometric changes associated with it.

Magnetic Resonance Spectroscopy Studies of Major Depressive Disorder (MDD)

While there are several MRS studies in bipolar disorder (reviewed by Moore & Renshaw, 1997b), there are only two $^{31}$P MRS studies (Kato et al., 1992; Moore et al., 1997a) and one $^{1}$H MRS analysis of MDD (Charles et al., 1994). Kato et al. (1992), using a coronal slice DRESS $^{31}$P MRS protocol, examined the frontal cortex of 12 subjects (age 35.3∀12.1 years) with MDD, 10 subjects (age 42∀8.6 years) with bipolar disorder and 22 control subjects (age 36.1∀11.5 years). Although the pH and PME levels were significantly higher in euthymic MDD subjects compared with euthymic bipolar subjects, no significant differences were found for $^{31}$P MRS parameters of MDD subjects compared with control subjects. A study by Moore et al. (1997a) using a $^{31}$P MRS ISIS protocol, measured $^{31}$P metabolites in a 45 cm$^3$ voxel containing the bilateral basal ganglia in 35 unmedicated subjects (age 37.2∀lain 8.5 years) with MDD and 18 control subjects (age 38.2∀9.9 years). There was a 16% reduction in ATP (β-ATP peak) in the MDD subjects. The PCr/Pi ratio of MDD subjects compared with control subjects did not change. This study indicates that an abnormality in basal ganglia high-energy phosphate metabolism is associated with MDD. A $^{1}$H MRS study by Charles et al. (1994), using a combination of the STEAM technique for spatial lipid suppression and 1D CSI for additional spatial localization of the basal ganglia and thalamus, examined seven subjects with MDD (age range 63-76, mean=71.4 years ) compared with ten control subjects (age range 65-75, mean=68.9 years). The subjects with MDD were medication free for two (1 subject) or three (6 subjects) weeks. The authors report an increase in the TMA MRS peak in the basal ganglia of MDD subjects and subsequent drop in the trimethlyamine (TMA) peak in four subjects after treatment. We have recently observed an increase in PME and a decrease in PCr in two subjects with MDD (Pettegrew et al., unpublished results).

Molecular and Metabolic Effects of ALCAR

There is neuroimaging evidence for neurodegeneration and a reduction in energy metabolite levels and rCBF in MDD. These findings provide a rationale for the use of ALCAR in MDD as there is a considerable body of research that indicates that ALCAR has a positive modulating influence on membrane structure, function and metabolism, energy metabolism, and the physiology and metabolism of neurotrophic factors. There also is clinical evidence that ALCAR is beneficial in the treatment of neurodegenerative disorders as well as normal aging-related processes and the treatment of geriatric depression. A thorough review of the possible CNS actions of ALCAR has appeared (Calvani & Carta, 1991; Pettegrew et al., 2000). What follows is a brief review of the metabolic, physiologic, behavioral, and clinical roles for ALCAR.

ALCAR'S Effect on Energy Metabolism

ALCAR has been shown to exert a beneficial effect on brain metabolism after energetic stresses. In a canine model of complete, global cerebral ischemia and reperfusion, ALCAR treated animals exhibited significantly lower neurological deficit scores (p=0.0037) and more normal cerebral cortex lactate/pyruvate ratios than did vehicle-treated control animals (Rosenthal et al., 1992). In a rat cyanide model of acute hypoxia, increased rate of phosphatidic acid formation, possibly reflecting increased phospholipase C activity was observed and spatial navigation performance in a Morris task was impaired. Chronic treatment with ALCAR attenuated the cyanide-induced behavioral deficit but had no effect on energy-dependent phosphoinositide metabolism suggesting ALCAR affected free fatty acid metabolism by increasing the reservoir of activated acyl groups involved in the reacylation of membrane phospholipids (Blokland et al., 1993). In a canine model employing 10 minutes of cardiac arrest followed by restoration of spontaneous circulation for up to 24 hours, ALCAR eliminated the reperfusion elevation of brain protein carbonyl groups which reflect free radical-induced protein oxidation (Liu et al., 1993). In a rat streptozotocin-induced model of brain hypoglycemia, ALCAR attenuated both the streptozotocin-induced impairment in spatial discrimination learning and decrease in hippocampal choline acetyltransferase activity (Prickaerts et al., 1995). A deficiency in ALCAR has been shown to be a cause for altered nerve myo-inositol content, $Na^+$—$K^+$-ATPase activity, and motor conduction velocity in the streptozotocin-diabetic rat (Stevens et al., 1996). Finally, sparse-fur mice have a deficiency of hepatic ornithine transcarbamylase resulting in congenital hyperammonemic with elevated cerebral anmonia and glutamine and reduced cerebral cytochrome oxidase activity and a reduction in cerebral high-energy phosphate levels. ALCAR treatment increased cytochrome oxidase subunit I mRNA, and restored both cytochrome oxidase activity and the levels of high-energy phosphates (Rao et al., 1997). Our studies of hypoxia in Fischer 344 rats demonstrate ALCAR's beneficial effect on brain membrane phospholipid and high-energy phosphate metabolism (Pettegrew et al., unpublished results.

ALCAR'S Effect on Membrain Composition, Structure, and Dynamics

ALCAR has been shown to effect membrane structure and function in a number of different systems. ALCAR administration affects the inner mitochondrial membrane protein composition in rat cerebellum (Villa et al., 1988), increases human erythrocyte membrane stability possibly by interacting with cytoskeletal proteins (Arduini et al., 1990), increases human erythrocyte cytoskeletal protein-protein interactions (Butterfield & Rangachari, 1993), and alters the membrane dynamics of human erythrocytes in the region of the glycerol backbone of membrane phospholipid bilayers (Arduini et al., 1993).

ALCAR∝S Enhancement of Nerve Growth Factor Activity

A number of studies have demonstrated that ALCAR enhances the neurotrophic activity of nerve growth factor (NGF). ALCAR increases NGF binding in aged rat hippocampus and basal forebrain (Angelucci et al., 1988), increases NGF receptor expression in rat striatum, and increases choline acetyltranferase activity in the same area (De Simone R. et al., 1991), enhances PC12 cells response to NGF (Taglialatela et al., 1991), increases the level of NGF receptor (P75NGFR) mRNA (Taglialatela et al., 1992), increases choline acetyltransferase activity and NGF levels in adult rats following total fimbria-fomix transection (Piovesan et al., 1994; 1995), and enhances motomeuron survival in rat facial nucleus after facial nerve transection (Piovesan et al., 1995).

Influence of ALCAR on Cholinergic and Serotonergic Neurotransmitter Systems

ALCAR has some cholinergic activity (Fritz, 1963; Tempesta et al., 1985), possibly because it shares conformational properties with acetylcholine (Sass & Werness, 1973). This is interesting as acetylcholine may play an important role in the chronobiological organization of the human body (Morley & Murrin, 1989; Wee & Turek, 1989), mediating also some effects of light on the circadian clock (Wee & Turek, 1989). Acetylcholine is implicated in the regulation of the hypothalamic-pituitary-adrenal (HPA) axis (Mueller et al., 1977; Risch et al., 1981) and cholinomimetics are effective on the HPA axis (Janowsky et al., 1981; Risch et al., 1981). ALCAR also seems to interfere with the serotonergic system (Tempesta et al., 1982; 1985). There is ample evidence supporting a reduction in serotonergic activity in depression (Ashcroft et al., 1966; Asberg et al., 1976; Cochran et al., 1976; Traskman et al., 1981; Stanley & Mann, 1983); although these results have not always been confirmed (Bowers, 1974; Murphy et al., 1978). The efficacy of 5-HTP also has been reported in involutional depression (Aussilloux et al., 1975). Moreover the selective serotonin reuptake inhibitors (SSRI) antidepressants increase serotonergic transmission and are currently widely used in treating MDD (Aberg-Wistedt et al., 1982; Stark & Hardison, 1985). Serotonin plays an important role in the regulation of circadian rhythms (Kordon et al., 1981; Leibiwitz et al., 1989) and there is consistent evidence that it affects cortisol secretion (Imura et al., 1973; Krieger, 1978; Meltzer et al., 1982).

ALCAR'S Effect on Aging-Relating Metabolic Changes

ALCAR has been demonstrated to reverse aging-related changes in brain ultrastructure, neurotransmitter systems, membrane receptors, mitochondrial proteins, membrane structure and metabolism, memory, and behavior. ALCAR restores the number of axosomatic and giant bouton vesicles in aged rat hippocampus (Badiali et al., 1987), reduces aging-related lipofuscin accumulation in prefrontal pyramidal neurons and hippocampal CA3 neurons in rats (Kohjimoto et al., 1988; Amenta et al., 1989), and reduces aging-related changes in the rat hippocampal mossy fiber system (Ricci et al., 1989). ALCAR reduces the age-dependent loss of glucocorticoid receptors in rat hippocampus (Ricci et al., 1989), attenuates the age-dependent decrease in NMDA receptors in rat hippocampus (Fiore & Rampello, 1989; Castorina et al., 1993; 1994; Piovesan et al., 1994; and reviewed by Castorina & Ferraris, 1988), and reduces age-related changes in the dopaminergic system of aging mouse brain (Sershen et al., 1991). Age-related changes in mitochondria also are reduced by ALCAR. ALCAR increases cytochrome oxidase activity in rat cerebral cortex, hippocampus, and striatum (Curti et al., 1989), restores to normal reduced transcripts of mitochondrial DNA in rat brain and heart but not liver (Gadaleta et al., 1990), increases cytochrome oxidase activity of synaptic and non-synaptic mitochondria (Villa & Gorini, 1991), reverses age-related reduction in the phosphate carrier and cardiolipin levels in heart mitochondria (Paradies et al., 1992), reverses age-related reduction in cytochrome oxidase and adenine nucleotide transferase activity in rat heart by modifying age-related changes in mitochondrial cardiolipin levels (Paradies et al., 1994; 1995), and reverses age-related alteration in the protein composition of the inner mitochondrial membrane (Villa et al., 1988). ALCAR also increases synaptosomal high-affinity choline uptake in the cerebral cortex of aging rats (Curti et al., 1989; Piovesan et al., 1994), increases choline acetyltransferase activity in aged rat striatum (De Simone R. et al., 1991; Taglialatela et al., 1994), modulates age-related reduction in melatonin synthesis (Esposti et al., 1994), reverses the age-related elevation in free and esterified cholesterol and arachidonic acid (20:4) in rat plasma (Ruggiero et al., 1990), and increases PCr and reduces lactate/pyruvate and sugar phosphate levels in adult and aged rat brain (Aureli et al., 1990). Age-related changes in NGF are reduced by ALCAR: ALCAR increases NGF receptor expression in rat striatum (De Simone R. et al., 1991) and in PC12 cells (Castorina et al., 1993); enhances the effect of NGF in aged dorsal root ganglia neurons (Manfridi et al., 1992); exerts a neurotrophic effect in three month old rats after total fimbria transection (Piovesan et al., 1994); and increases NGF levels in aged rat brain (Taglialatela et al., 1994). ALCAR has been shown in aged rats to modulate synaptic structural dynamics (Bertoni-Freddari et al., 1994) and improve measures of behavior (Angelucci, 1988; Kohjimoto et al., 1988) as well as memory (Barnes et al., 1990; Caprioli et al., 1990; 1995). ALCAR has been reported to normalize the pituitary-adrenocortical hyperactivity in pathological brain aging (Nappi et al., 1988; Ghirardi et al., 1994). We have reported that ALCAR improves standardized clinical measures and measures of membrane phospholipid and high-energy phosphate metabolism in subjects with Alzheimer's disease (AD) measured by in vivo $^{31}$P MRS (Pettegrew et al., 1995). We now have data in a rat hypoxia model which demonstrate that ALCAR has more beneficial effects on aged rats (30 months) than on adolescent (1 month) or adult (12 months) animals (Pettegrew et al., unpublished results).

Antidepressant Effects of ALCAR

In European clinical trials, ALCAR has been shown to have significant antidepressant activity in geriatric depressed subjects with minimal or no side effects (Villardita et al., 1983; Tempesta et al., 1987; Nasca et al., 1989; Bella et al., 1990; Fulgente et al., 1990; Garzya et al., 1990; Gecele et al., 1991). Villardita et al. (1983) reported a double-blind ALCAR/placebo study of 28 subjects (18 males, 10 females; 72.3∀7.3 years). Sixteen subjects were treated with ALCAR (1.5 gm/day; baseline HDRS=26.3∀3.3) and 12 Patients were treated with placebo (baseline HDRS=26.6∀3.2) for 40 days. By day 40, the ALCAR treated subjects showed significant improvement (p<0.001) in the Hamilton Depressive Rating Scale (HDRS) but the placebo treated subjects did not. There were no side effects to ALCAR. Tempesta et al. (1987) in an open label, cross over study of 24 subjects over the age of 70 years, all of whom were nursing home residents, reported ALCAR (2 gm/day) to be highly effective in reducing HDRS scores, especially in subjects with more severe clinical symptoms. Again there were no reported ALCAR side effects. In a simple blind ALCAR/placebo study of 20 subjects (10 ALCAR treated subjects; 62.5∀5.7 years, 8 males, 2 females, baseline HDRS=44.9∀3.1 and 10 placebo treated subjects; 62.5∀5.3 years, 8 males, 2 females, baseline HDRS=43.9∀2.8), Nasca et al. (1989) demonstrated a significant improvement in the HDRS scores of ALCAR treated subjects at day 40 of treatment (p<0.001). There was no improvement in the placebo treated group. Similar significant beneficial effects of ALCAR on the HDRS were observed in randomized, double-blind, ALCAR/placebo studies of Garzya et al. (1990) (28 subjects; ages 70-80 years; ALCAR 1.5 gm/day), Fulgente et al. (1990) [60 subjects; 70-80 years; ALCAR 3.0 gm/day; baseline HDRS (ALCAR=25; placebo=23); day 60 HDRS (ALCAR=12; placebo=22); p # 0.0001], and Bella et al. (1990) [60 subjects, 60-80 years, ALCAR 3.0 gm/day; baseline HDRS (ALCAR=22; placebo=21); day 60 HDRS (ALCAR=11; placebo=20); p # 0.0001]. ALCAR was well tolerated in these studies even at the higher dosages. A double-blind, ALCAR/placebo study by Gecele et al. (1991) (30 subjects, 66-79 years, ALCAR 2 gm/day) not only showed a significant improvement in the HDRS of ALCAR treated subjects (p<0.001) but a significant reduction in both mean cortisol levels (p<0.001) as well as 12 am (p<0.001) and 4 pm (p<0.01) cortisol levels.

Since acetyl-1-carnitine (ALCAR) is a natural substance and has been shown to have antidepressant properties without significant side effects and without the potential to induce mania, it is a logical new therapeutic approach.

LCAR is important in the β-oxidation of fatty acids and ALCARc contains carnitine and acetyl moieties, both of which have neurobiological properties. LCAR is important in the β-oxidation of fatty acids and the acetyl moiety of ALCAR can be used to maintain acetyl-CoA levels. Other reported neurobiological effects of ALCAR include modulation of: 1) brain energy and phospholipid metabolism; 2) cellular macromolecules including neurotrophic factors and neurohormones; 3) synaptic morphology; and 4) synaptic transmission of multiple neurotransmitters. Potential molecular mechanisms of ALCAR include: 1) acetylation of —NH2 and —OH functional groups in amino acids and N-terminal amino acids in peptides and proteins resulting in modification of their structure, dynamics, function and turnover; and 2) acting as a molecular chaperone to a larger molecule.

There is data demonstrating that ALCAR can acetylate lysine 28 in the Aβ(1-40) peptide derived from the ubiquitous protein, amyloid precursor protein. ALCAR is reported to have neuroprotective effects (Pettegrew et al., 2000) and could become recognized as a dietary component important to mental health—particularly in older populations. ALCAR has therapeutic indications for Alzheimer's disease (Pettegrew et al., 1995); geriatric depression (Pettegrew et al., 2002); schizophrenia (Masterson and Wood, 2000).

However, LCAR and ALCAR are difficult to produce. There is a need for producing a low-cost nutraceutical to treat major mental illnesses, especially in poor countries such as LCAR and ALCAR.

Thus, it is desirable to provide compositions, compounds and methods that can be used to produce LCAR and ALCAR.

REFERENCES

Aberg-Wistedt A, Ross S B, Jostell K G & Sjoqvist B. A double-blind study of a 5-HT uptake inhibitor in endogenous depression. *Acta Psychiatr Scand* 66:66-82, 1982.

Aitchison J. *The Statistical Analysis of Compositional Data*, Chapter 7, London: Chapman and Hall, 1986, Alexopoulos G S, Meyers B S, Young R C, Kakuma T, Feder M, Einhorn A & Rosendahl E. Recovery in geriatric depression. *Arch Gen Psychiatry* 53:305-312, 1996.

Altman P L and Dittmer D S (1968) *Metabolism, Biological Handbooks*. Fed. Soc. Exp. Biol., Bethesda Md.

Altshuler L L, Post R M, Leverich G S, Mikalauskas K, Rosoff A and Ackerman L (1995) Antidepressant-induced mania and cycle acceleration: A controversy revisited.[see comment]. *Am. J Psychiatry* 152, 1130-1138.

Amenta F, Ferrante F, Lucreziotti R, Ricci A & Ramacci M T. Reduced lipofuscin accumulation in senescent rat brain by long-term acetyl-L-carnitine treatment. *Arch Gerontol Geriatr* 9:147-153, 1989.

Angelucci L, Ramacci M T, Taglialatela G, Hulsebosch C, Morgan B, Werrbach-Perez K & Perez-Polo R. Nerve growth factor binding in aged rat central nervous system: effect of acetyl-L-carnitine. *J Neurosci Res* 20:491-496, 1988.

Arduini A, Gorbunov N, Arrigoni-Martelli E, Dottori S, Molajoni F, Russo F & Federici G. Effects of L-carnitine and its acetate and propionate esters on the molecular dynamics of human erythrocyte membrane. *Biochim Biophys Acta* 1146: 229-235, 1993.

Arduini A, Rossi M, Mancinelli G, Belfiglio M, Scurti R, Radatti G & Shohet S B. Effect of L-carnitine and acetyl-L-carnitine on the human erythrocyte membrane stability and deformability. *Life Sci* 47:2395-2400, 1990.

Asberg M, Traskman L & Thoren P. 5-HIAA in the cerebrospinal fluid: A biochemical suicide predictor? *Arch Gen Psychiatry* 33:1193-1197, 1976.

Ashcroft G W, Crawford T B B, Eccleston D, Sharman D F, MacDougall E J, Stanton J B & Binns J K. 5-Hydroxyindole compounds in the cerebrospinal fluid of patients with psychiatric or neurological disease. *Lancet* ii: 1049-1052, 1966.

Asplund P T and Curtis W R (2001) Intrinsic oxygen use kinetics of transformed plant root culture. *Biotechnology Progress* 17, 481-489.

Aureli T, Miccheli A, Ricciolini R, Di Cocco M E, Ramacci M T, Angelucci L, Ghirardi O & Conti F. Aging brain: Effect of acetyl-L-carnitine treatment on rat brain energy and phospholipid metabolism. A study by $^{31}$P and $^{1}$H NMR spectroscopy. *Brain Res* 526:108-112, 1990.

Aussilloux C H, Castelnau D, Chiariny J F & Frassinet M. A propos d'une autre voie d'abord des etats depressifs les precurseurs de la serotonine. *J Med (Montpellier)* 10:23-25, 1975.

Badiali D L, Bonvicini F, Bianchi D, Bossoni G & Laschi R. Ultrastructural aspects of ageing rat hippocampus and effects of L-acetyl-carnitine treatment. *Drugs Under Experimental & Clinical Research* 13:185-189, 1987.

Barnes C A, Markowska A L, Ingram D K, Kametani H, Spangler E L, Lemken V J & Olton D S. Acetyl-L-carnitine. 2: Effects on learning and memory performance of aged rats in simple and complex mazes.*Neurobiol Aging* 11:499-506, 1990.

Beekman A T, Deeg D J, van Tilburg T, Smit J H, Hooijer C & van Tilburg W. Major and minor depression in later life: a study of prevalence and risk factors. *J Affective Disorders* 36:65-75, 1995.

Bella R, Bondi R, Raffaele R & Pennisi G. Effect of acetyl-L-carnitine on geriatric patients suffering from dysthymic disorders. *Int J Clin Pharmacol Res* 10:355-360, 1990.

Benazzi F (1997) Antidepressant-associated hypomania in outpatient depression: a 203-case study in private practice. *J Affective Disord.* 46, 73-77.

Bertoni-Freddari C, Fattoretti P, Casoli T, Spagna C & Casell U. Dynamic morphology of the synaptic junctional areas during aging: the effect of chronic acetyl-L-carnitine administration. *Brain Res* 656:359-366, 1994.

Birken D L & Oldendorf W H. N-Acetyl-L-aspartic acid: A literature review of a compound prominent in $^1$H-NMR spectroscopic studies of brain. *Neurosci Biobehav Rev* 13:23-31, 1989.

Blazer D G, Hughes D C & George L K. The epidemiology of depression in an elderly community population. *Gerontologist* 27:281-287, 1987.

Blokland A, Bothmer J, Honig W & Jolles J. Behavorial and biochemical effects of acute central metabolic inhibition: effects of acetyl-L-carnitine. *Eur J Pharmacology* 235:275-281, 1993.

Bode K, Hooks M A, and Couee,I. Identification, separation, and characterization of acyl-coenzyme A dehydrogenases involved in mitochondrial beta-oxidation in higher plants. *Plant Physiol.* 119, 1305-1314. 1999.

Borson S. Psychiatric problems in the mentally ill elderly. In: *Comprehensive Textbook of Psychiatry*, edited by H I Kaplan & B J Sadock, 6$^{th}$ edition, p. 2586, 1995.

Borson S, Barnes R A, Kukull W A, Okimoto J T, Veith R C, Inui T S, Carter W & Raskind M A. Symptomatic depression in elderly medical outpatients.I.Prevalence, demography, and health service utilization. *J Am Geriatr Soc* 34:341-347, 1986.

Bostwick J M & Pankratz V S. Affective disorders and suicide risk. *Am. J. Psychiatry,* 157:1925-1932, 2000.

Botteron K N & Figiel G S. The neuromorphometry of affective disorders. In: *Brain Imaging in Clinical Psychiatry*, edited by K R R Krishnan & P M Doraiswamy. New York: Marcel Dekker,Inc., 1997, p. 145-184.

Bowers M B. Lumbar CSF 5-hydroxyindoleacetic acid and homovanillic acid in affective syndromes. *J Nerv Ment Dis* 158:325-330, 1974.

Bremer J (1983) Carnitine—metabolism and functions. *Physiol. Rev.* 63, 1420-1480. Broquist H P (1994) Carnitine, in *Modern Nutrition* (Shils M E, Olson J A and Shike M S eds), pp 459-465,Lea & Febiger, Baltimore.

Buchsbaum M S, Wu J, DeLisi L E, Holcomb H, Kessler R, Johnson J, King A C, Hazlett E, Langston K & Post R M. Frontal cortex and basal ganglia metabolic rates assessed by positron emission tomography with [$^{18}$F]2-deoxyglucose in affective illnness. *J Affective Disord* 10:137-152, 1986.

Burgard A P and Maranas C D (2003) Optimization-based framework for inferring and testing hypothesizedmetabolic objective functions. *Biotechnology & Bioengineering* 82, 670-677.

Burnell E E, Cullis P R & de Kruijff B. Effects of tumbling and lateral diffusion on phosphatidylcholine model membrane $^{31}$P-NMR lineshapes. *Biochim Biophys Acta* 603:63-69, 1980.

Butterfield D A & Rangachari A. Acetylcarnitine increases membrane cytoskeletal protein-protein interactions. *Life Sci* 52:297-303, 1993.

Callahan C M, Hui S L, Nienaber N A, Musick B S & Tierney W M. Longitudinal study of the depression and health services use among elderly primary care patients. *J Am Geriatr Soc* 42:833-838, 1994.

Calvani M & Carta A. Clues to the mechanism of action of acetyl-L-carnitine in the central nervous system. *Dementia* 2:1-6, 1991.

Carvalho E B and Curtis W R (2002) Effect of elicitation on growth, respiration, and nutrient uptake of root and cell suspension cultures of Hyoscyamus muticus. *Biotechnology Progress* 18, 282-289.

Caprioli A, Ghirardi O, Ramacci M T & Angelucci L. Age-dependent deficits in radial maze performance in the rat: effect of chronic treatment with acetyl-L-carnitine. *Progress In Neuro-Psychopharmacology & Biological Psychiatry* 14:359-369, 1990.

Caprioli A, Markowska A L & Olton D S. Acetyl-L-Carnitine: chronic treatment improves spatial acquisition in a new environment in aged rats. *J Gerontology Series A, Biological Sciences & Medical Sciences* 50:B232-B236, 1995.

Castorina M, Ambrosini A M, Giuliani A, Pacifici L, Ramacci M T & Angelucci L. A cluster analysis study of acetyl-L-carnitine effect on NMDA receptors in aging. *Exp Gerontol* 28:537-548, 1993.

Castornia M, Ambrosini A M, Pacific L, Ramacci M T & Angelucci L. Age-dependent loss of NMDA receptors in hippocampus, striatum, and frontal cortex of the rat: prevention by acetyl-L-carnitine. *Neurochem Res* 19:795-798, 1994.

Cerdan S, Subramanian V H, Hilberman M, Cone J, Egan J, Chance B & Williamson J R. $^{31}$P NMR detection of mobile dog brain phospholipids. *Magn Reson Med* 3:432-439, 1986.

Charles H C, Lazeyras K K, Krishnan K R R, Boyko O B, Payne M & Moore D. Brain choline in depression: In vivo detection of potential pharmacodynamic effects of antidepressant therapy using hydrogen localized spectroscopy. *Prog Neuropsychopharmacol Biol Psychiatry* 18:1121-1127, 1994.

Cochran E, Robin E & Grote S. Regional serotonin levels in brain: a comparison of depressive suicide and alcoholic suicides with control. *Biol Psychiatry* 11:283-294, 1976.

Coffey C E, Figiel G S & Djang W T. Leukoencephalopathy in elderly depressed patients referred for ETC. *Biol Psychiatry* 24:143-161, 1988.

Coffey C E, Wilkerson W E, Weiner R D, Parashos I A, Djang W T, Webb M C, Figiel G S & Spritzer C E. Quantative cerebral anatomy in depression. *Arch Gen Psychiatry* 50:7-16, 1993.

Cohen M M, Pettegrew J W, Kopp S J, Minshew N and Glonek T (1984) P-31 nuclear magnetic resonance analysis of brain: normoxic and anoxic brain slices. *Neurochem. Res.* 9, 785-801.

Conwell Y. Suicide in elderly patients. In: *Diagnosis and Treatment of Depression in Late Life*, edited by L S Schneider, C F Reynolds & B D Lebowitz. 1996, p. 397-418.

Cullis P R & DeKruijff B. Lipid polymorphism and the functional roles of lipids in biological membranes. *Biochim Biophys Acta* 559:399-420, 1979.

Curti D, Dagani F, Galmozzi M R & Marzatico F. Effect of aging and acetyl-L-carnitine on energetic and cholinergic metabolism in rat brain regions. *Mech Ageing Develop* 47:39-45, 1989.

de Beer R & van Ormondt D. Analysis of NMR data using time domain fitting procedures. In: *NMR Basics, Principles and Progress*, edited by P Diehl & E G Fluck. New York: Springer-Verlag, 1992, p. 201-258.

de Graaf A A, vanDijk J E, & Bovee W M M J. QUALITY: quantification improvement by converting lineshapes to the Lorentzian type. *Magn Reson Med* 13:343-357, 1990.

de Kruijff B, Rietveld A & Cullis P R. $^{31}$P-NMR studies on membrane phospholipids in microsomes, rat liver slices and intact perfused rat liver. *Biochim Biophys Acta* 600:343-357, 1980.

de Kruijff B, Verkley A J, van Echteld C J A, Gerritsen W J, Mombers C, Noordam P C & De Gier J. The occurance of lipidic particles in lipid bilayers as seen by $^{31}$P NMR and freeze-fracture electron-microscopy. *Biochim Biophys Acta* 555:200-209, 1979.

De Simone R., Ramacci M T & Aloe L. Effect of acetyl-L-carnitine on forebrain cholinergic neurons of developing rats. *Int J Develop Neurosci* 9:39-46, 1991.

Desu M M & Raghavarao D. *Sample Size Methodology*. New York: Academic Press, 1990, page 30.

Dew M A, Reynolds C F, Houck P R, Hall M, Buysse D J, Frank E & Kupfer D J. Temporal profiles of the course of depression during treatment: Predictors of pathways toward recovery in the elderly. *Arch Gen Psychiatry* 54:1016-1024, 1997.

Dunlop, D S and Curtis, W R. Synergistic response of plant hairy-root cultures to phosphate limitation and fungal elicitation. *Biotechnology Progress* 7, 434-438. 1991.

Dupont R M, Jernigan T L, Heindel W, Butters N, Shafer K, Wilson T, Hesselink J & Gillin J C. Magnetic resonance imaging and mood disorders. *Arch Gen Psychiatry* 52:747-755, 1995.

Eastmond P J, Germain V, Lange P R, Bryce J H, Smith S M and Graham I A (2000) Postgerminative growth and lipid catabolism in oilseeds lacking the glyoxylate cycle. *Proc. Natl. Acad. Sci. USA* 97, 5669-5674.

Efron B & Tibshirani R. *An Introduction to the Bootstrap*. London: Chapman and Hall, 1993.

Esposti D, Mariani M, Demartini G, Lucini V, Fraschini F & Mancia M. Modulation of melatonin secretion by acetyl-L-carnitine in adult and old rats. *J Pineal Res* 17 :132-136, 1994.

Figiel G S, Coffey C E & Weiner R D. Brain magnetic resonance imaging in elderly depressed patients receiving electroconvulsive therapy. *Convulsive Ther* 5:26-34, 1989.

Fiore L & Rampello L. L-acetylcarnitine attenuates the age-dependent decrease of NMDA-sensitive glutamate receptors in rat hippocampus. *Acta Neurol* 11:346-350, 1989.

Folstein M, Folstein S & McHugh P R. Mini-mental state: A practical method for grading the cognitive state of patients for the clinician. *J Psychiatr Res* 12:189-198, 1975.

Frahm J, Bruhn H, Gyngell M L, Merboldt K D, Hanicke W & Sauter R. Localized proton NMR spectroscopy in different regions of the human brain in vivo. Relaxation times and concentrations of cerebral metabolites. *Magn Reson Med* 11:47-63, 1989.

Frasure-Smith N, Lesperance F & Talajic. Depression following myocardial infarction. *JAMA* 270:1819-1825, 1993.

Frasure-Smith N, Lesperance F & Talajic M. Depression and 18-month prognosis after myocardial infarction. *Circulation* 91:999-1005, 1995.

Fritz I B. Carnitine and its role in fatty acid metabolism. *Adv Lipid Res* 1:285-333, 1963.

Fulgente T, Onofij M, Del Re M L, Ferracci F, Bazzano S, Ghilardi M F & Malatesta G. Laevo-acetylcarnitine (Nicetile$^R$) treatment of senile depression. *Clin Tri J* 27:155-163, 1990.

Gadaleta M N, Petruzzella V, Renis M, Fracasso F & Cantatore P. Reduced transcription of mitochondrial DNA in the senescent rat. Tissue dependence and effect of L-carnitine. *Eur J Biochem* 187:501-506, 1990.

Garzya G, Corallo D, Fiore A, Lecciso G, Petrelli G & Zotti C. Evaluation of the effects of L-acetylcarnitine on senile patients suffering from depression. *Drugs Exptl Clin Res* 16:101-106, 1990.

Gecele M, Francesetti G & Meluzzi A. Acetyl-L-carnitine in aged subjects with major depression: Clinical efficacy and effects on the circadian rhythm of cortisol. *Dementia* 2:333-337, 1991.

Geddes J W, Panchalingam K, Keller J N and Pettegrew J W (1997) Elevated phosphocholine and phosphatidyl choline following rat entorhinal cortex lesions. *Neurobiol. Aging* 18, 305-308.

Geriatric Pyschiatry Allicance. Diagnosis and treatment of late-life depression: making a difference. Monograph produced through a grant from Pfizer, Inc., 1996.

Ghirardi O., Caprioli, O., Ramacci, M. T. and Angelucci, L., Effect of long-term Acetyl-L-carnitine on stress-induced analgesia in the aging rat. *Exp Gerontol* 29:569-574, 1994.

Girton, R E. Effects of oxygen concentration on the respiration of excised root-tip segments of maize andrice, and of germinating grains of rice and buckwheat. Physiologica Plantarum 46, 58-62. 1979.

Glonek T, Kopp S J, Kot E, Pettegrew J W and Cohen M M (1982a) P-31 nuclear magnetic resonance analysis of brain. The perchloric acid extract spectrum. *Trans. Am. Soc. Neurochem.* 13, 143.

Glonek T, Kopp S J, Kot E, Pettegrew J W, Harrison W H and Cohen M M (1982b) P-31 nuclear magnetic resonance analysis of brain: The perchloric acid extract spectrum. *J Neurochem*. 39, 1210-1219.

Gonzalez-Mendez R, Litt L, Koretsky A P, von Colditz J, Weiner M W & James T L. Comparison of $^{31}$P NMR spectra of in vivo rat brain using convolution difference and saturation with a surface coil. Source of the broad component in the brain spectrum. *J Magn Reson* 57:526-533, 1984.

Goodwin F K & Jamison K R. Manic Depressive Illness, New York, N.Y., Oxford University Press, 1990.

Graham I A and Eastmond P J (2002) Pathways of straight and branched chain fatty acid catabolism in higher plants. *Prog. Lipid Res.* 41, 156-181.

Grunze H, Kasper S, Goodwin G, et al., World federation of societies of biological psychiatry (WFSBP) guidelines for biological treatment of bipolar disorder, part 1: treatment of bipolar depression. *World J. Biol. Pschiatry,* 3:115-124, 2002.

Harris G J, Barta P E, Peng L W, Lee S, Brettschneider P D, Shah A, Henderer J D, Schlaepfer T E & Pearlson G D. MR volume segmentation of gray matter and white matter using manual thresholding: Dependence on image brightness. *AJNR* 15:225-230, 1994.

Harris G J, Rhew E H, Noga T & Pearlson G D. User-friendly method for rapid brain and CSF volume calculation using transaxial MRI images. *Psychiatry Res Neuroimaging* 40:61-68, 1991.

Haselgrove J C, Subramanian J H, Christen R & Leigh P N. Analysis of in vivo NMR spectra. *Rev Magn Reson Med* 2:167-222, 1987.

Henry C, Sorbara F, Lacoste J, Gindre C and Leboyer M (2001) Antidepressant-induced mania in bipolar patients: identification of risk factors. [see comment]. *J Clin. Psychiatry* 62, 249-255.

Herschfeld R M A, Bowden C L, Gitlin M J, et al., Practice guideline for the treatment of patients with bipolar disorder (revision). *Am. J Psychiatry,* 59:1-50, 2002.

Hsu J H and Shen W W (1995) Male sexual side effects associated with antidepressants: a descriptive clinical study of 32 patients. *International Journal of Psychiatry in Medicine* 25, 191-201.

Husain M M, McDonald W M, Doraiswamy P M, Figiel G S, Na C, Escalona P R, Boyko O B, Nemeroff C B & Krishnan K R R. A magnetic resonance imaging study of putamen nuclei in major depression. *Psychiatry Res* 40:95-99, 1991.

Iacobazzi V, Naglieri M A, Stanley C A, Wanders R J and Palmieri F (1998) The structure and organization of the human carnitine/acylcarnitine translocase (CACTI) gene2. *Biochemical & Biophysical Research Communications* 252, 770-774.

Imura H, Naki Y & Yoshimi T. Effects of 5-hydroxytryptophan (5-HTP) on growth hormone and ACTH release in man. *J Clin Endocrinol Metab* 36:204-206, 1973.

International Conference. Draft consensus guideline: Statistical principles for clinical trials. *International conference on harmonisation of technical requirements for registration of pharmaceuticals for human use*, ICH Steering Committee, 1997.

Janowsky D S, Risch S C, Judd L L & et al. Cholinergic supersensitivity in affective disorder patients: Behavioral and neuroendocrine observations. *Psychopharmacol Bull* 17:129-132, 1981.

Joffe R T, MacQueen G M, Marriott M, Robb J, Begin H and Young L T (2002) Induction of mania and cycle acceleration in bipolar disorder: effect of different classes of antidepressant. *Acta Psychiatr. Scand.* 105, 427-430.

Kanfer J N, Pettegrew J W, Moossy J and McCartney D G (1993) Alterations of selected enzymes of phospholipid metabolism in Alzheimer's disease brain tissue as compared to non-Alzheimer's disease controls. *Neurochem. Res.* 18, 331-334.

Kato T, Takahashi S, Shioiri T & Inubushi T. Brain phosphorus metabolism in depressive disorders detected by phosphorus-31 magnetic resonance spectroscopy. *J Affective Disord* 26 :223-230, 1992.

Kato T, Inubushi T and Kato N (1998) Magnetic resonance spectroscopy in affective disorders. *J. Neuropsychiatry Clin. Neurosci.* 10, 133-147.

Keshavan M S, Anderson S, Beckwith C, Nash K, Pettegrew J & Krishnan K R R. A comparison of stereology and segmentation techniques for volumetric measurements of brain ventricles. *Psychiatry Res Neuroimaging* 61:53-60, 1995.

Keshavan M S, Beckwith C, Bagwell W, Pettegrew J W & Krishnan K R R. An objective method for edge detection in MRI morphometry. *Eur Psychiatry* 9:205-207, 1994.

Keshavan M S, Pettegrew J W, Panchalingam K, Kaplan D and Bozik E (1991) Phosphorus 31 magnetic resonance spectroscopy detects altered brain metabolism before onset of schizophrenia. *Arch. Gen. Psychiatry* 48, 1112-1113.

Keshavan M S, Stanley J A, Montrose D M, Minshew N J and Pettegrew J W (2003) Prefrontal membrane phospholipid metabolism of child and adolescent offspring at risk for schizophrenia or schizoaffective disorder: an in vivo $^{31}$P MRS study. *Molecular Psychiatry* 8, 316-323.

Kilby P M, Bolas N M & Radda G K.

31P-NMR study of brain phospholipid structures in vivo. *Biochim Biophys Acta* 1085:257-264, 1991.

Klunk W E, Xu C J, McClure R J, Panchalingam K, Stanley J A & Pettegrew J W. Aggregation of beta-amyloid peptide is promoted by membrane phospholipid metabolites elevated in Alzheimer's disease brain. *J Neurochem* 97:266-272, 1997.

Klunk W E, Xu C J, Panchalingam K, McClure R J and Pettegrew J W (1994) Analysis of magnetic resonance spectra by mole percent: Comparison to absolute units. *Neurobiol. Aging* 15, 133-140.

Klunk W E, Panchalingam K, McClure R J, Stanley J A and Pettegrew J W (1998) Metabolic alterations in postmortem Alzheimer's disease brain are exaggerated by Apo-E4. *Neurobiol. Aging* 19, 511-515.

Klunk W E, Xu C, Panchalingam K, McClure R J and Pettegrew J W (1996) Quantitative $^1$H and $^{31}$P MRS of PCA extracts of postmortem Alzheimer's disease brain. *Neurobiol. Aging* 17, 349-357.

Kohjimoto Y, Ogawa T, Matsumoto M, Shirakawa K, Kuwaki T, Yasuda H, Anami K, Fujii T, Satoh H & Ono T. Effects of acetyl-L-carnitine on the brain lipofuscin content and emotional behavior in aged rats. *Japanese J Pharmacology* 48:365-371, 1988.

Kordon C, Hery M, Szafarcyk A, Ixart A & Assenmacher I. Serotonin and the regulation of neuroendocrine rhythms. *J Physiol* 77:489-496, 1981.

Krieger D. Factors influencing the circadian periodicity of ACTH and corticosteriods. *Med Clin North Am* 62:87-91, 1978.

Krishnan K R, McDonald W M, Doraiswamy P M, Tupler L A, Husain M, Boyko O B, Figiel G S & Ellinwood E H, Jr. Neuroanatomical substrates of depression in the elderly. *Eur Arch Psychiatry Clin Neurosci* 243:41-46, 1993.

Krishnan K R R. Neuroanatomic substrates of depression in the elderly. *J Geriatric Psychiatry Neurol* 6:39-58, 1993.

Lebowitz B D, Pearson J L, Schneider L S, Reynolds C F, Alexopoulos G S, Bruce M L, Conwell Y, Katz I R, Meyers B S, Morrison M F, Mossey J F, Neiderehe g & Parmelee P A. Diagnosis and treatment of depression in late-life: Consensus statement update. *JAMA* 278:1186-1190, 1997.

Lehninger A L, Nelson D L and Cox M M (1993) *Principles of Biochemistry*. Worth Publishers, New York.

Leibiwitz S F, Weiss G F, Walsh U A & Viswanath D. Medial hypotalamic serotonin: Role in circadian patterns of feeding and macronutrient selection. *Brain Res* 503:132-140, 1989.

Lim K O, Pauly J, Webb P, Hurd R & Macovski A. Short TE phosphorus spectroscopy using a spin-echo pulse. *Magn Reson Med* 32:98-103, 1994.

Little J T, Reynolds C F, Dew M A, Frank E, Begley A E, Miller M D, Comes C L, Mazumdar S, Perel J M & Kupfer D J. How common is treatment-resistant geriatric depression. *Am J Psychiatry* (under editorial review) 1998.

Liu Y, Rosenthal R E, Stark-Reed P & Fiskum G. Inhibition of postcardiac arrest brain protein oxidation by acetyl-L-carnitine. *Free Radical Biol Med* 15:667-670, 1993.

Longo A, Bruno G, Curti S, Mancinelli A, Miotto G (1996) Determination of L-carnitine, acetyl-Lcarnitine and propionyl-L-carnitine in human plasma by high-performance liquid chromatography after pre-column derivatization with 1-aminoanthracene. *J Chromatography B: Biomed. Appl.* 686, 129-139.

Luyten P R, Bruntink G, Sloff F M, Vermeulen J W A H, van der Heijden J I, den Hollander J A & Heerschap A. Broadband proton decoupling in human $^{31}$P NMR spectroscopy. *NMR in Biomedicine* 1:177-183, 1989.

Manfridi A, Forloni G L, Arrigoni-Martelli E & Mancia M. Culture of dorsal root ganglion neurons from aged rats: effects of acetyl-L-carnitine and NGF. *Int J Develop Neurosci* 10:321-329, 1992.

Mason R P, Trumbore M W & Pettegrew J W. Membrane interactions of a phosphomonoester elevated early in Alzheimer's disease. *Neurobiol Aging* 16:531-539, 1995.

Masterson C and Wood C (2000) Mitochondrial beta-oxidation of fatty acids in higher plants. *Physiologia Plantarum* 109, 217-224.

Mayberg H S, Lewis P J, Regenold W & Wagner H N. Paralimbic hypoperfusion in unipolar depression. *J Nucl Med* 35:929-934, 1994.

McIlwain H & Bachelard H S. *Biochemistry and the central nervous system*. 5th edition, Edinburgh: Churchill Livingstone, 1985, p. 42.

McNamara R, Arias-Mendoza F & Brown T R. Investigation of broad resonances in $^{31}$P NMR spectra of the human brain in vivo. *NMR Biomedicine* 7:237-242, 1994.

Meltzer H Y, Wiita B, Tricou B J, Simonovic M & Fang V S. Effects of serotonin precursors and serotonin agonists on plasma hormone levels. *Adv Biochem Psychopharmacol* 34:117-140, 1982.

Meneses P and Glonek T (1988) High resolution $_{31}$P NMR of extracted phospholipids. *J. Lipid Res.* 29, 679-690.

Merboldt K D, Chien D, Hanicke W, Gyngell M L, Bruhn H & Frahm J. Localized $^{31}$P NMR spectroscopy of the adult human brain in vivo using stimulated-echo (STEAM) sequences. *J Magn Reson* 89:343-361, 1990.

Meyers B. Psychiatric intervention to improve primary care diagnosis and treatment of depression. *Am J Geriatric Psychiatry* 4:S91-S95, 1996.

Michaelis T, Merboldt K D, Bruhn H & Frahm J. Absolute concentrations of metabolites in the adult human brain in vivo: Quantification of localized proton NMR spectra. *Radiology* 187:219-227, 1993.

Mohr H and Schopfer P (1995) *Plant Physiology*. Springer-Verlag, New York.

Moore C M, Frederick B B and Renshaw P F (1999) Brain biochemistry using magnetic resonance spectroscopy: relevance to psychiatric illness in the elderly. *Journal of Geriatric Psychiatry & Neurology* 12, 107-117.

Miller B L, Moats R A, Shonk T, Ernst T, Woolley S & Ross B D. Alzheimer's disease: Depiction of increased cerebral myo-inositol with proton MR spectroscopy. *Radiology* 187: 433-437, 1993.

Moore C M, Christensen J D, Lafer B, Fava M & Renshaw P F. Lower levels of nucleoside triphosphate in the basal ganglia of depressed subjects: A phosphorous-31 magnetic resonance spectroscopy study. *Am J Psychiatry* 154:116-118, 1997a.

Moore C M & Renshaw P F. Magnetic resonance spectroscopy studies of affective disorders. In: *Brain Imaging in Clinical Psychiatry*, edited by K R R Krishnan & P M Doraiswamy. New York: Marcel Dekker, 1997b, p. 185-213.

Morley B J & Murrin L C. AF64 depletes hypothalamic high affinity choline uptake and disrupts the circadian rhythm of locomotor activity without altering the density of nicotinic acetylcholine receptors. *Brain Res* 504:238-246, 1989.

Mueller E E, Nistico G & Scapagnini U. Brain neurotransmitters and the regulation of anterior pituitary function. In: *Neurotransmitters and Anterior Pituitary Function*, edited by E E Mueller, G Nistico & U Scapagnini. New York: Academic Press, 1977.

Murphy D L, Campbell I & Costa J L. Current studies of the indoleamine hypothesis of the affective disorders. In: *Psychopharmacolgy: A Generation of Progress*, edited by M A Lipton, A DiMascio & K F Killam. New York: Raven Press, 1978, p. 1235-1248.

Murphy E J, Bates T E, Williams S R, Watson T, Brindle K M, Rajagopalan B & Radda G K. Endoplasmic reticulum: The major contributor to the PDE peak in hepatic $^{31}$P-NMR spectra at low magnetic field strengths. *Biochim Biophys Acta* 1111:51-58, 1992.

Murphy E J, Rajagopalan B, Brindle K M & Radda G K. Phospholipid bilayer contribution to $^{31}$P NMR spectra in vivo. *Magn Reson Med* 12:282-289, 1989.

Murray C J L & Lopez A D (editors). The Global Burden of Disease, Cambridge, Mass., Harvard University Press, 1996.

Nappi G & et al. Acetyl-L-carnitine normalizes pituitary-adrenocortical hyperactivity in pathological ageing brain. *Med Sci Res* 16:291-292, 1988.

Nardini M, Bonelli G, Iannuccelli M, Calvani M, Magnani N & Mancuso M. Assessment of L-acetylcarnitine efficacy against fluoxetine in the depressive syndrome. In preparation, 1998.

Nasca D, Zurria G & Aguglia E. Action of acetyl-L-carnitine in association with mianserine on depressed old people. *New Trends Clin Neuropharmacology* 3:225-230, 1989.

Nelva A, Guy C, Tardy-Poncet B, Beyens M N, Ratrema M, Benedetti C and Ollagnier M (2000) [Hemorrhagic syndromes related to selective serotonin reuptake inhibitor (SSRI) antidepressants. Seven case reports and review of the literature] [French]. *Revue De Medecine Interne* 21, 152-160.

Oxman T E, Barrett J E, Barrett J & Gerber P. Symptomatology of late-life minor depression among primary care patients. *Psychosomatics* 31:174-180, 1990.

Pannuri, S, Reddy, G R, McNeill, D, and Curtis, W R. Interpreting the role of phosphorus and growth rate in enhansed fungal induction of sesquiterpenes from Hyoscyamus muticus root cultures. *Applied and Microbial Biotechnology* 38, 550-555. 1993.

Panter R A and Mudd J B (1969) Carnitine levels in some higher plants. *FEBS Lett.* 5, 169-170.

Paradies G, Ruggiero F M, Gadaleta M N & Quagliariello E. The effect of aging and acetyl-L-carnitine on the activity of the phosphate carrier and on the phospholipid composition in rat hear mitochondria. *Biochim Biophys Acta* 1103:324-326, 1992.

Paradies G, Ruggiero F M, Petrosillo G, Gadaleta M N & Quagliariello E. Effect of aging and acetyl-L-carnitine on the activity of cytochrome oxidase and adenine nucleotide translocase in rat heart mitochondria. *FEBS Letters* 350:213-215, 1994.

Paradies G, Ruggiero F M, Petrosillo G, Gadaleta M N & Quagliariello E. Carnitine-acylcarnitine translocase activity in cardiac mitochondria from aged rats: the effect of acetyl-L-carnitine. *Mechanisms of Ageing & Development* 84:103-112, 1995.

Petroff O A C, Prichard J W, Behar K L, Alger J R, den Hollander J A & Shulman R G. Cerebral intracellular pH by $^{31}$P nuclear magnetic resonance spectroscopy. *Neurology* 35:781-788, 1985.

Pettegrew J W, Glonek T, Baskin F and Rosenberg R N (1978) Phosphorus-31-31 NMR of neuroblastoma clonal lines. Effect of cell cycle stage and dibutyryl cyclic AMP. *Proc. 14th Midwest Regional Am. Chem. Soc.* 45.

Pettegrew J W, Glonek T, Baskin F and Rosenberg R N (1979a) Phosphorus-31 NMR of neuroblastoma clonal lines: effect of cell confluency state and dibutyryl cyclic AMP. *Neurochem. Res.* 4, 795-801.

Pettegrew J W [editor] (1990) *NMR: Principles and Applications to Biomedical Research*. Springer-Verlag, New York.

Pettegrew J W, Keshavan M S, Panchalingam K, Strychor S, Kaplan D B, Tretta M G and Allen M (1991) Alterations in brain high-energy phosphate and membrane phospholipid metabolism in first-episode, drug-naive schizophrenics. A pilot study of the dorsal prefrontal cortex by in vivo phosphorus 31 nuclear magnetic resonance spectroscopy. *Arch. Gen. Psychiatry* 48, 563-568.

Pettegrew J W, Klunk W E, Kanal E, Panchalingam K and McClure R J (1995) Changes in brain membrane phospholipid and high-energy phosphate metabolism precede dementia. *Neurobiol. Aging* 16, 973-975.

Pettegrew J W, Klunk W E, Panchalingam K, Kanfer J N and McClure R J (1995) Clinical and neurochemical effects of acetyl-L-carnitine in Alzheimer's disease. *Neurobiol. Aging* 16, 1-4.

Pettegrew J W, Kopp S J, Dadok J, Minshew N J, Feliksik J M, Glonek T and Cohen M M (1986) Chemical characterization of a prominent phosphomonoester resonance from mammalian brain: $^{31}$P and $^1$H NMR analysis at 4.7 and 14.1 tesla. *J. Magn. Reson.* 67, 443-450.

Pettegrew J W, Kopp S J, Minshew N J, Glonek T, Feliksik J M, Tow J P and Cohen M M (1987a) $^{31}$P nuclear magnetic resonance studies of phosphoglyceride metabolism in developing and degenerating brain: Preliminary observations. *J. Neuropathol. Exp. Neurol.* 46, 419-430.

Pettegrew J W, Levine J, Gershon S, Stanley J A, Servan-Schreiber D, Panchalingam K and McClure R J (2002) $^{31}$P-MRS study of acetyl-L-carnitine treatment in geriatric depression: preliminary results. *Bipolar Disorders* 4, 61-66.

Pettegrew J W and Minshew N J (1981) Effects of short chain fatty acids on cellular membranes and energy metabolism: A nuclear magnetic resonance study. *Neurology* 31, 143.

Pettegrew J W, Minshew N J, Glonek T, Kopp S J and Cohen M M (1982a) Phosphorus NMR study of gerbil stroke model. *Neurology* 32, 196.

Pettegrew J W, Minshew N J, Spiker D, McClure R J and Klunk W E (1993a) Membrane alterations in erythrocytes of affective illness patients. *Biol. Psychiatry* 33, 47A.

Pettegrew J W, Minshew N J, Spiker D, Tretta M, Strychor S, McKeag D, Munez L R, Miller G M, Carbone D and McClure R J (1993b) Alterations in membrane molecular dynamics in erythrocytes of patients with affective illness. *Depression* 1, 88-100.

Pettegrew J W, Minshew N J and Stewart R M (1981a) Dynamic membrane studies in individuals at risk for Huntington's disease. *Neurology* 31, 151.

Pettegrew J W, Moossy J, Withers G, McKeag D and Panchalingam K (1988a) $^{31}$P Nuclear Magnetic Resonance study of the brain in Alzheimer's disease. *J. Neuropathol. Exp. Neurol.* 47, 235-248.

Pettegrew J W, Nichols J S, Minshew N J, Rush A J and Stewart R M (1982b) Membrane biophysical studies of lymphocytes and erythrocytes in manic-depressive illness. *J. Affective Disord.* 4, 237-247.

Pettegrew J W, Nichols J S and Stewart R M (1979b) Fluorescence spectroscopy on Huntington's fibroblasts. *J. Neurochem.* 33, 905-911.

Pettegrew J W, Nichols J S and Stewart R M (1979c) Fluorescence studies of fibroblasts, lymphocytes, and erythrocytes in Huntington's disease. *Ann. Neurol.* 6, 164.

Pettegrew J W, Nichols J S and Stewart R M (1980a) Membrane biophysical studies in manic-depressive intact peripheral tissues. *Neurology* 30, 375.

Pettegrew J W, Nichols J S and Stewart R M (1980b) Membrane studies in Huntington's disease: steady-state fluorescence studies of intact erythrocytes. *Ann. Neurol.* 8, 381-386.

Pettegrew J W, Nichols J S and Stewart R M (1981b) Membrane studies in Huntington's disease: Steady-state and time-dependent fluorescence spectroscopy of intact lymphocytes. *J. Neurochem.* 36, 1966-1976.

Pettegrew J W, Panchalingam K, Hamilton R L and McClure R J (2001) Brain membrane phospholipid alterations in Alzheimer's disease. *Neurochem. Res.* 26, 771-782.

Pettegrew J W, Panchalingam K, Klunk W E, McClure R J and Muenz L R (1994) Alterations of cerebral metabolism in probable Alzheimer's disease: A preliminary study. *Neurobiol. Aging* 15, 117-132.

Pettegrew J W, Panchalingam K, Moossy J, Martinez J, Rao G and Boller F (1988b) Correlation of phosphorus-31 magnetic resonance spectroscopy and morphologic findings in Alzheimer's disease. *Arch. Neurol.* 45, 1093-1096.

Pettegrew J W, Panchalingam K, Spiker D, Minshew N, McKeag D, Strychor S and Tretta M (1998) Membrane molecular dynamics in affective illness. *Soc. Biol. Psychiatry, 43rd Annual Sci. Program* 364.

Pettegrew J W, Panchalingam K, Withers G, McKeag D and Strychor S (1990a) Changes in brain energy and phospholipid metabolism during development and aging in the Fischer 344 rat. *J. Neuropathol. Exp. Neurol.* 49, 237-249.

Pettegrew J W, Short J W, Woessner R D, Strychor S, McKeag D W, Armstrong J, Minshew N J and Rush A J (1987b) The effect of lithium on the membrane molecular dynamics of normal human erythrocytes. *Biol. Psychiatry* 22, 857-871.

Pettegrew J W, Strychor S, Tretta M and McKeag D (1990b) Membrane molecular alterations in Alzheimer's erythrocytes. *Neurology* 40 (Suppl. 1), 404.

Pettegrew J W, Strychor S, Tretta M and McKeag D (1990c) Membrane molecular alterations in Alzheimer's erythrocytes (abstract). *Neurology* 40 (Suppl. 1), 404.

Pettegrew J W, Klunk W E, Panchalingam K, Kanfer J N & McClure R J. Clinical and neurochemical effects of acetyl-L-carnitine in Alzheimer's disease. *Neurobiol Aging* 16:1-4, 1995.

Pettegrew J W, McClure R J, Keshavan M S, Minshew N J, Panchalingam K & Klunk W E. $^{31}$P magnetic resonance spectroscopy studies of developing brain. In: *Neurodevelopement & Adult Psychopathology*, edited by M S Keshavan & R M Murray. Cambridge University Press, 1997, p. 71-92.

Pettegrew J W, Withers G, Panchalingam K & Post J F. Considerations for brain pH assessment by $^{31}$P NMR. *Magn Reson Imaging* 6:135-142, 1988.

Pettegrew J W, Levine J, and McClure R J. Acetyl-L-carnitine physical-chemical, metabolic, and therapeutic properties: Relevance for its mode of action in Alzheimer's disease and geriatric depression. *Molecular Psychiatry* 5, 616-632, 2000.

Pettegrew J W, Levine J, Gershon S, Stanley J A, Servan-Schreiber D, Panchalingam K and McClure R J (2002) $_{31}$P-MRS study of acetyl-L-carnitine treatment in geriatric depression: preliminary results. *Bipolar Disorders* 4, 61-66.

Pettegrew J W, Levine J and McClure R J (2000) Acetyl-L-carnitine physical-chemical, metabolic, and therapeutic properties: Relevance for its mode of action in Alzheimer's disease and geriatric depression. *Molecular Psychiatry* 5, 616-632.

Pettegrew J W, Panchalingam K, Withers G, McKeag D and Strychor S (1990) Changes in brain energy and phospholipid metabolism during development and aging in the Fischer 344 rat. *J. Neuropathol. Exp. Neurol.* 49, 237-249.

Pettegrew J W, Keshavan M S, Panchalingam K, Strychor S, Kaplan D B, Tretta M G and Allen M (1991) Alterations in brain high-energy phosphate and membrane phospholipid metabolism in first-episode, drugnaive schizophrenics. A pilot study of the dorsal prefrontal cortex by in vivo phosphorus 31 nuclear magnetic resonance spectroscopy. *Arch. Gen. Psychiatry* 48, 563-568.

Pettegrew J W, Panchalingam K, Klunk W E, McClure R J and Muenz L R (1994) Alterations of cerebral metabolism in probable Alzheimer's disease: A preliminary study. *Neurobiol. Aging* 15, 117-132.

Pfefferbaum A, Lim K O, Rosenbloom M & Zipursky R B. Brain magnetic resonance imaging: Approaches for investigating schizophrenia. *Schizophr Bull* 16:453-476, 1990.

Piovesan P, Pacifici L, Taglialatela G, Ramacci M T & Angelucci L. Acetyl-L-carnitine treatment increases choline acetyltransferase activity and NGF levels in the CNS of adult rats following total fimbria-fornix transection. *Brain Res* 633:77-82, 1994.

Piovesan P, Quatrini G, Pacifici L, Taglialatela G & Angelucci L. Acetyl-L-carnitine restores choline acetyltransferase activity in the hippocampus of rats with partial unilateral fimbria-fornix transection. *International Journal of Developmental Neuroscience* 13:13-19, 1995.

Prickaerts J, Blokland A, Honig W, Meng F & Jolles J. Spatial discrimination learning and choline acetyltransferase activity in streptozotocin-treated rats: effects of chronic treatment with acetyl-L-carnitine. *Brain Res* 674:142-146, 1995.

Provencher S W. Estimation of metabolite concentrations from localized in vivo proton NMR spectra. *Magn Reson Med* 30:672-679, 1993.

Rabins P V, Pearlson G D & Aylward E. Cortical magnetic resonance imaging changes in elderly inpatients with major depression. *Am J Psychiatry* 148:617-620, 1991.

Ramakrishnan, D, Luyk, D, and Curtis, W R. Monitoring biomass in root culture systems. *Biotechnol. Bioeng.* 62, 711-721. 1999.

Ramasubbu R (2001) Dose-response relationship of selective serotonin reuptake inhibitors treatment-emergent hypomania in depressive disorders. *Acta Psychiatr. Scand.* 104, 236-238.

Rao K V, Mawal Y R & Qureshi I A. Progressive decrease of cerebral cytochrome C oxidase activity in sparse-fur mice: role of acetyl-L-carnitine in restoring the ammonia-induced cerebral energy depletion. *Neurosci Lett* 224:83-86, 1997.

Rasband W. *NIH Image Manual.* Bethesda, Md.: National Institutes of Health, 1993.

Raymond, P, Spiteri, A, Dieuaide, M, Gerhardt, B, and Pradet, A. Peroxysomal beta-oxidation of fatty acids and citrate formation by a particulate fraction from early germinating sunflower seeds. *Plant Physiol. Biochem.* 30, 153-161. 1992.

Reynolds C F, Frank E, Kupfer D J, Thase M E, Perel J M, Mazumdar S & Houck P R. Treatment outcome in recurrent major depression: A post-hoc comparison of elderly ("young old") and mid-life patients. *Am J Psychiatry* 153:1288-1292, 1996.

Reynolds C F, Frank E, Perel J, Mazumdar S & Kupfer D J. Maintenance therapies for late-life recurrent major depression: Research and review circa 1995. *International Psychogeriatrics* 7:27-40, 1995.

Reynolds C F, Nowell P D, Hoch C C, Neylan T C, Buysse D J & Kupfer D J. Diagnosis and treatment of insomnia in the elderly. In: *Clinical Geriatric Psychopharmacology*, edited by C Salzman. 1997, Ricci A, Ramacci M T, Ghirardi O & Amenta F. Age-related changes of the mossy fibre system in rat hippocampus: effect of long term acetyl-L-carnitine treatment. *Arch Gerontol Geriatrics* 8:63-71, 1989.

Risch S C, Kalin N H & Janowsky D S. Cholinergic challenges, behavioral and neuroendocrine correlates. *J Clin Psychopharmacol* 1:186-192, 1981.

Rosenberg D R, Keshavan M S, Dick E L, Bagwell W W, McMaster F, Seymour A B & Birmaher A B. Quantitative morphology of the corpus callosum in pediatric obsessive compulsive disorder. *Prog Neuropsychopharmacology Biol Psychiatry*, in press, 1997.

Rosenthal R E, Williams R, Bogaert Y E, Getson P R & Fiskum G. Prevention of postischemic canine neurological injury through potentiation of brain energy metabolism by acetyl-L-carnitine. *Stroke* 23:1312-1318, 1992.

Rovner B W. Depression and increased risk of mortality in the nursing home patient. *Am J Med* 94:19S-22S, 1993.

Ruggiero F M, Cafagna F, Gadaleta M N & Quagliariello E. Effect of aging and acetyl-L-carnitine on the lipid composition of rat plasma and erythrocytes. *Biochem Biophys Res Commun* 170:621-626, 1990.

Sachs G S, Printz D J, Kahn D A, Carpenter D, & Docherty J P. The Expert Consensus Guideline Series: Medication Treatment of Bipolar Disorder, *Postgraduate Med.* April, Spec:1-104, 2000.

Salon C, Raymond P and Pradet A (1988) Quantification of carbon fluxes through the tricarboxylic acid cycle in early germinating lettuce embryos. *J. Biol. Chem.* 263, 12278-12287.

Sass R L & Wemess P. Acetylcarnitine on the relationship between structure and function. *Biochem Biophys Res Commun* 55:736-742, 1973.

Schlegel S, Aldenhoff J B, Eissner D, Linder P & Nickel O. Regional cerebral blood flow in depression: Associations with psychopathology. *J Affective Disord* 17:211-218, 1989.

Seelig J. 31P nuclear magnetic resonance and the head group structure of phospholipids in membranes. *Biochim Biophys Acta* 515:105-140, 1978.

Sershen H, Harsing L J, Banay-Schwartz M, Hashim A, Ramacci M T & Lajtha A. Effect of acetyl-L-carnitine on the dopaminergic system in aging brain. *J Neurosci Res* 30:555-559, 1991.

Singh I, Xu C, Pettegrew J W and Kanfer J N (1994) Endogenous inhibitors of human choline acetyltransferase present in Alzheimer's brain: Preliminary observation. *Neurobiol. Aging* 15, 643-649.

Smith C J (1999) Carbohydrate Biochemistry, in *Plant Biochemistry and Molecular Biology* (Lea P J and Leegood R C eds), Wiley, Chichester; New York.

Smith I C P & Ekiel I H. Phosphorus-31 NMR of Phospholipids in Membranes. In: *Phosphorus-31 NMR: Principles and Applications*, Academic Press, 1984, p. 447-474.

Stanley J A, Drost D J, Williamson P C & Thompson R T. The use of a priori knowledge to quantify short echo in vivo $^1$H MR spectra. *Magn Reson Med* 34:17-24, 1995.

Stanley J A, Panchalingam K, Miller G, McClure R J & Pettegrew J W. A new method to quantify the broad component under the phosphodiester resonance and its application to study first-episode never medicated schizophrenics [abstract]. *Proceedings of the 5th Annual meeting of the International Society of Magnetic Resonance in Medicine* SMR, Berkeley Calif.:1408, 1997.

Stanley J A, Williamson P C, Drost D J, Carr T, Tylett J & Merskey H. The study of schizophrenia via in vivo $^{31}$P and $^1$H MRS. *Schizophr Bull* 9:210-210, 1993.

Stanley J A, Williamson P C, Drost D J, Carr T J, Rylett R J, Morrison-Stewart S & Thompson R T. Membrane phospholipid metabolism and schizophrenia: An in vivo $^{31}$P-MR spectroscopy study. *Schizophr Res* 13:209-215, 1994.

Stanley M & Mann J J. Increased serotonin: 2-binding sites in frontal cortex of suicide victims. *Lancet* i:214-216, 1983.

Stark P & Hardison C D. A review of multicentre controlled studies of fluoxetine vs imipramine and placebo in our patients with major depressive disorder. *J Clin Psychiatry* 46:26-31, 1985.

Stevens M J, Lattimer S A, Feldman E L, Helton E D, Millington D S, Sima A A & Greene D A. Acetyl-L-carnitine deficiency as a cause of altered nerve myo-inositol content, Na,K-ATPase activity, and motor conduction velocity in the streptozotocin-diabetic rat. *Metabolism: Clinical & Experimental* 45:865-872, 1996.

Sweet R A, Panchalingam K, Pettegrew J W, McClure R J, Hamilton R L, Lopez O L, Kaufer D I, DeKosky S T and Klunk W E (2002) Psychosis in Alzheimer disease: postmortem magnetic resonance spectroscopy evidence of excess neuronal and membrane phospholipid pathology. *Neurobiol. Aging* 23, 547-553.

Szanto K, Prigerson H G, Houck P R & Reynolds C F. Suicidal ideation in elderly bereaved: The role of complicated grief. *Suicide and Life-Threatening Behavior* 27:194-207, 1997.

Taglialatela G, Angelucci L, Ramacci M T, Werrbach-Perez K, Jackson GR & Perez-Polo J R. Acetyl-L-carnitine enhances the response of PC12 cells to nerve growth factor. *Brain Res Develop Brain Res* 59:221-230, 1991.

Taglialatela G, Angelucci L, Ramacci M T, Werrbach-Perez K, Jackson G R & Perez-Polo J R. Stimulation of nerve growth factor receptors in PC12 by acetyl-L-carnitine. *Biochem Pharmacol* 44:577-585, 1992.

Taglialatela G, Navarra D, Cruciani R, Ramacci M T, Alema G S & Angrist B. Acetyl-L-carnitine treatment increases nerve growth factor levels and choline acetyltransferase activity in the central nervous system of aged rats. *Exp Gerontol* 29:55-66, 1994.

Talairach J & Toumoux P. *Co-planar Stereotaxic Atlas of the Human Brain*. New York: Thieme Medical Publishers, 1988.

Tamada R S, Issler C K, Amaral J A, Sachs G S and Lafer B (2004) Treatment emergent affective switch: a controlled study. *Bipolar Disorders* 6, 333-337.

Tempesta E, Casella L, Pirrongelli C, Janiri L, Calvani M & Ancona L. L-acetylcarnitine in depressed elderly subjects. A cross-over study vs placebo. *Drugs Under Experimental Clin Res* 13:417-423, 1987.

Tempesta E, Janiri L & Pirrongelli C. Stereospecific effects of acetylcarnitine on the spontaneous activity of brain-stem neurons and their responses to acetylcholine and serotonin. *Neuropharmacology* 24:43-50, 1985.

Tempesta E, Janiri L & Salera P. The effects of microiontophoretically applied acetyl-L-carnitine on single neurons in the rats brain-stem. *Neuropharmacology* 21:111982.

Thomas D R and Wood C (1986) The two beta-oxidation sites in pea cotyledons. Camitive palmitoyltransferase location and function in pea mitochondria. *Planta* 168, 261-266.

Traskman L, Asberg M, Bertilsson L & Sjostrand L. Monoamine metabolites in CSF and suicidal behavior. *Arch Gen Psychiatry* 38:631-636, 1981.

Urenjak J, Williams S R, Gadian D G & Noble M. Specific expression of N-acetylaspartate in neurons, oligodendrocyte-type-2 astrocyte progenitors, and immature oligodendrocytes in vitro. *J Neurochem* 59:55-61, 1992.

van der Veen J W, de Beer R, Luyten P R & van Ormondt D. Accurate quantification of in vivo $^{31}$P NMR signals using the variable projection method and prior knowledge. *Magn Reson Med* 6:92-98, 1988.

Vance D E. Phospholipid metabolism and cell signalling in eucaryotes. In: *Biochemistry of lipids, lipoproteins and membranes, Volume* 20, edited by D E Vance & J Vance. New York: Elsevier, 1991, p. 205-240.

Villa R F & Gorini A. Action of L-acetylcarnitine on different cerebral mitochondrial populations from hippocampus and striatum during aging. *Neurochem Res* 16:1125-1132, 1991.

Villa R F, Turpeenoja L, Benzi G & Giuffrida S M. Action of L-acetylcarnitine on age-dependent modifications of mitochondrial membrane proteins from rat cerebellum. *Neurochem Res* 13:909-916, 1988.

Villardita C, Smimi P & Vecchio I. Acetyl-L-carnitine in depressed geriatric patients. *Eur Rev Med Pharm Sci* 6:1-12, 1983.

Volz H P, Rzanny R, Riehemann S, May S, Hegewald H, Preussler B, Hubner G, Kaiser W A and Sauer H (1998) $_{31}$P magnetic resonance spectroscopy in the frontal lobe of major depressed patients. *Eur. Arch. Psychiatry Clin. Neurosci.* 248, 289-295.

Wee B E & Turek F W. Carbachol phase shifts the circadian rhythm of locomotor activity in the jungarian hamster. *Brain Res* 505:209-214, 1989.

Most of the studies have been directed toward geriatric subjects. However, it is also desirable to use acetyl-L-carnitine (ALCAR) for non-geriatric human subjects as well as for adolescent human subjects.

SUMMARY OF THE INVENTION

In accordance with preferred embodiments of the present invention, some of the problems presently associated with producing LCAR and ALCAR are overcome. Compounds, compositions and methods for treating neuropsychiatric disorders are presented.

A metabolomics-guided bioprocess method is presented to enhance LCAR and ALCAR formation in germinating plant seeds. Metabolic fluxes are manipulated by germination in bioreactors to increase oxygen availability as well as provide an aseptic environment to alter carbohydrate consumption and feedback repress gluconeogenesis. Large shifts in germinating seed fatty acid, phospholipid and high-energy metabolism change the germination environment and these metabolic changes lead to an approximate 1000-fold increase in natural LCAR and ALCAR production by the germinating seeds.

The foregoing and other features and advantages of preferred embodiments of the present invention will be more readily apparent from the following detailed description. The detailed description proceeds with references to the accompanying drawings.

BRIEF DESCRIPTION OF THE DRAWINGS

Preferred embodiments of the present invention are described with reference to the following drawings, wherein:

FIG. 1B is a graph showing the correlation of PME(s-$\tau_c$) levels from the prefrontal region with HDRS scores for both depressed patients (● subject #1; ♦ subject #2);

FIG. 1A is a graph showing the correlation of PCr levels from the prefrontal region with HDRS scores for both depressed patients (● subject #1; ♦ subject #2);

DETAILED DESCRIPTION OF THE INVENTION

Figure 2A:
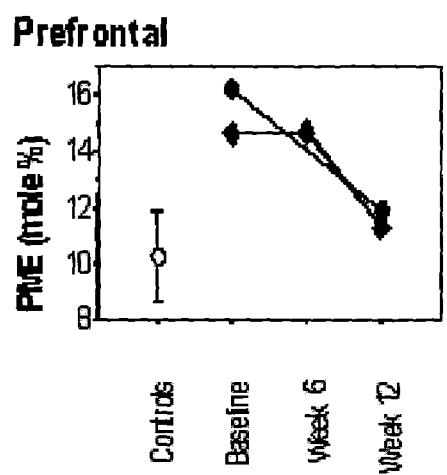
FIG. 2A is a graph showing PME(s-$\tau_c$) and FIG. 2B is a graph showing PCr levels in the a) prefrontal region of the two depressed patients (● subject #1; ♦ subject #2) and normal controls (O, n=6) at baseline and at 6 and 12 weeks follow up. The control values include meanplusSD.
Figure 2B:
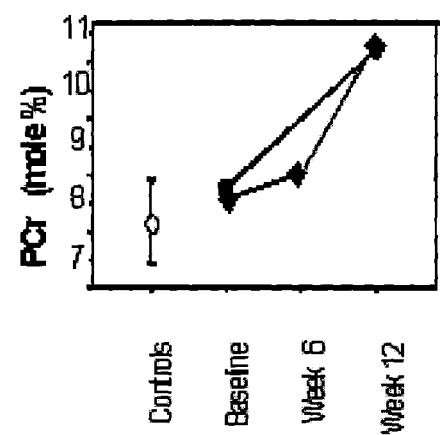
Figure 2C:
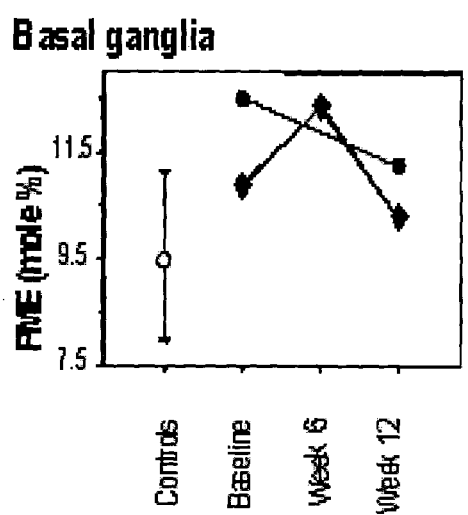
FIG. 2C is a graph showing PME(s-$\tau_c$)
Figure 2D:
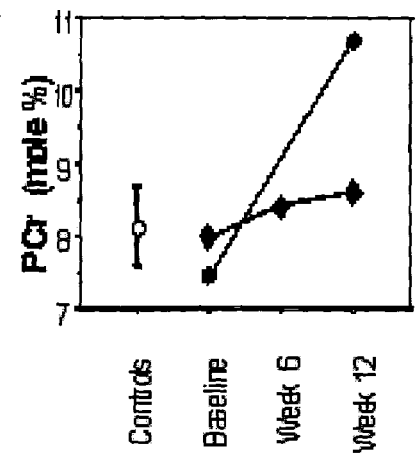
FIG. 2D is a graph showing and PCr levels in the basal ganglia region of the two depressed patients (● subject #1; ♦ subject #2) and normal controls (O, n=6) at baseline and at 6 and 12 weeks follow up. The control values include meanplusSD.
Figure 3A:
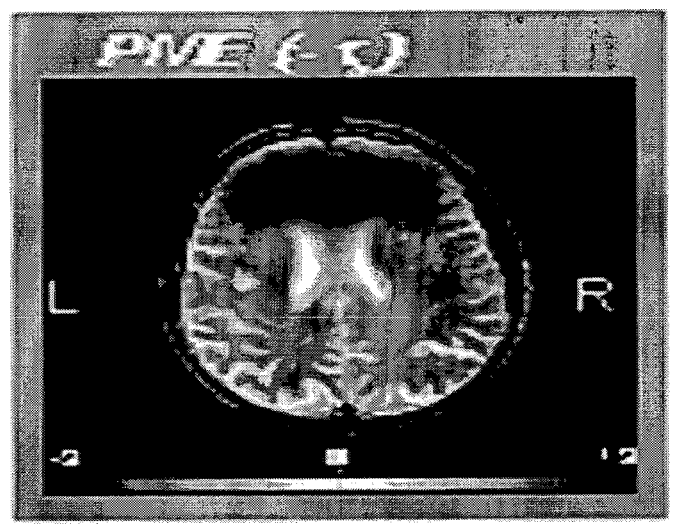
FIG. 3A is a phosphorous magnetic resonance spectroscopic image showing the Z-scores of the two depressed subjects compared with controls at entry and 12 weeks for PME(s-$\tau_c$) metabolite levels for those regions with significant differences. The intensity of the color is scaled to the z-score (mean difference/SD) given on the scale below the image. Z-scores for PME(s-$\tau_c$) and PCr levels in the frontal region exceed 3.0 and 2.0, respectively.
Figure 3A:
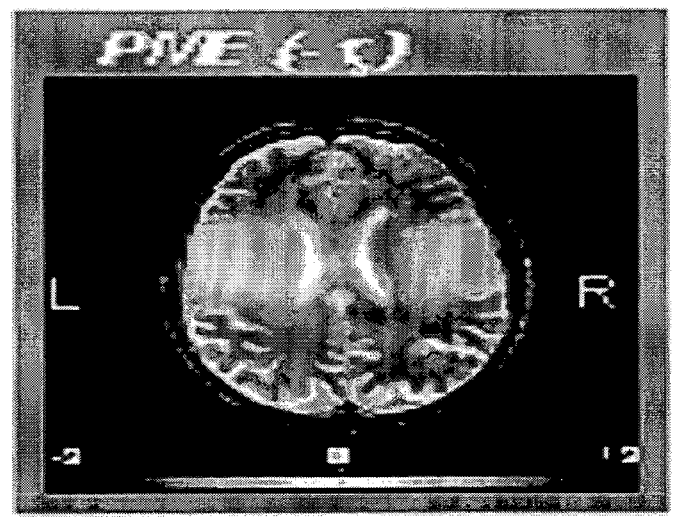
Figure 3B:
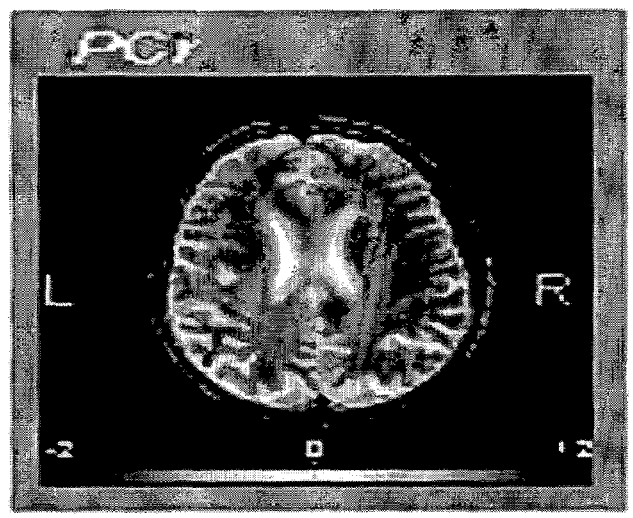
FIG. 3B is a phosphorous magnetic resonance spectroscopic image showing the Z-scores of the two depressed subjects compared with controls at entry and 12 weeks for PCr metabolite levels for those regions with significant differences. The intensity of the color is scaled to the z-score (mean difference/SD) given on the scale below the image. Z-scores for PME(s-$\tau_c$) and PCr levels in the frontal region exceed 2.0 and 2.0, respectively.
Figure 3B:
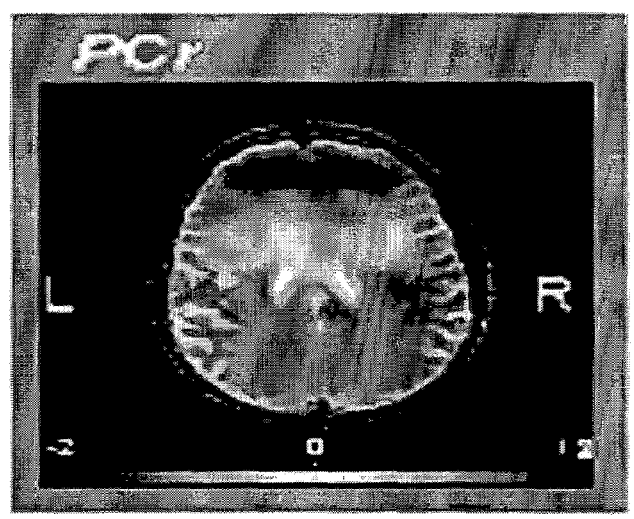

Carnitines in general are compounds of including the chemical formula (1):

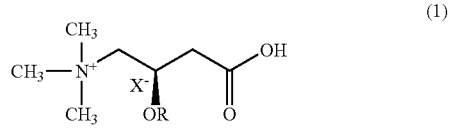

(1)

where R is hydrogen or an alkanoyl group with 2 to 8 carbon atoms, and $X^-$ represents the anion of a pharmaceutically acceptable salt.

The invention described herein includes both the administration of L-carnitine or an alkanoyl L-carnitine or one of its pharmacologically acceptable salts of formula (1) in the treatment of depression, and pharmaceutical compositions, which can be administered orally, parenterally or nasally, including controlled-release forms. Preferably, the alkanoyl L-carnitine is selected from the group consisting of acetyl-L-carnitine (hereinafter abbreviated to ALC or ALCAR), propionyl L-carnitine (hereinafter abbreviated to PLC), butyryl L-carnitine, valeryl L-carnitine and isovaleryl L-carnitine, or one of their pharmacologically acceptable salts. The ones preferred are acetyl L-carnitine, propionyl L-carnitine and butyryl L-carnitine. The most preferred is acetyl L-carnitine.

What is meant by a pharmacologically acceptable salt alkanoyl L-carnitine is any salt of the latter with an acid that does not give rise to toxic or side effects. These acids are well known to pharmacologists and to experts in pharmaceutical technology.

Examples of pharmacologically acceptable salts of L-carnitine or of the alkanoyl L-carnitines, though not exclusively these, are chloride; bromide; iodide; aspartate; acid aspartate; citrate; acid citrate; tartrate; acid tartrate; phosphate; acid phosphate; fumarate; acid fumarate; glycerophosphate; glucose phosphate; lactate; maleate; acid maleate; mucate; orotate, oxalate; acid oxalate; sulphate; acid sulphate; trichloroacetate; trifluoroacetate; methane sulphonate; pamoate and acid pamoate.

As used herein, a geriatric subject is an individual sixty-five years of age or older. See The Merck Manual, 15$^{th}$ edition (1987) p. 2389. A non-geriatric subject is less than sixty-five years old but not an adolescent.

Adolescence is the transitional stage of development between childhood and full adulthood, representing the period of time during which a person is biologically adult but emotionally may not at full maturity. The ages which are considered to be part of adolescence vary by culture. In the United States, adolescence is generally considered to begin around age thirteen, and end around twenty-four. By contrast, the World Health Organization (WHO) defines adolescence as the period of life between around age ten and end around age twenty years of age. As used herein, an adolescent subject is at least ten years old and less than twenty-six years old.

Phosphorus magnetic resonance spectroscopic imaging ($^{31}$P MRSI) analysis of two depressed elderly subjects treated with ALCAR for 12 weeks are compared with those of six normal non-demented, non-depressed subjects.

A twelve-week, open, clinical, $^{31}$P MRSI study design was used to examine the possible effects of ALCAR on brain metabolism and depressive symptomatology in non-demented geriatric major depressive disorder (NDG-MDD). Two depressed, non-demented [Folstein Mini-Mental State Exam (MMSE)>24)] male subjects, 70 and 80 years old, were compared with six age, social-economic status, and medically matched non-demented controls (all male, mean age of 73.6±3.6 years, range 69.7-78.2 years). The two elderly depressed subjects completed baseline Structural Clinical Interview of DSM-IV (SCID) I/P version 2.0, HDRS (17 item), MMSE, UKU Side Effect Rating Scale (UKU), and Cumulative Illness Rating Scale (CIRS) to assess medical burden, baseline physical, ECG, and, laboratory tests for hematology, urine analysis, immunopathology, and blood chemistry. Follow-up visits for the depressed subjects were done every other week for 12 weeks. Efficacy (psychiatric evaluation) was assessed by changes in the HDRS which was performed at baseline and every other week for 12 weeks along with secondary measures (MMSE; CIRS; and UKU), whereas the CIRS was performed at baseline, 6, and 12 weeks. Physical examinations and EKGs were performed at baseline, 6, and 12 weeks. The baseline MR evaluation was scheduled and completed prior to the administration of ALCAR. Follow-up MR evaluations were at 6 and 12 weeks. Acetyl-L-carnitine was administered in the form of oral tablets containing 590 mg of acetyl-L-carnitine hydrochloride (500 mg acetyl-L-carnitine). The dosage regimen was fixed at three grams of acetyl-L-carnitine given two tablets three times a day for 12 weeks.

$^{31}$P MRSI acquisition—A custom built, doubly tuned transmit/receive volume head coil was used to acquire the $^1$H MRI and 2D $^{31}$P MRSI data on a GE Signa 1.5 T whole body MR imager. First, sets of axial and sagittal scout MR images were collected. The 30 mm thick MRSI slice was positioned parallel with the anterior commisure-posterior commisure line to include the right and left prefrontal, basal ganglia, superior temporal, inferior parietal, occipital, and centrum semiovale regions. A self-refocused spin echo pulse sequence with an effective flip range of 60° and an echo time of 2.5 ms, was used to acquire the $^{31}$P MRSI (360 mm field of view, 30 mm$_3$ slice thickness, 8×8 phase encoding steps [45×45×30 mm nominal voxel dimensions], 2 s TR, 1024 data points, 4.0 kHz spectral bandwidth and 16 NEX).

MRSI post-processing and quantification—To optimize the right and left voxel positions for the six regions, the 8×8 $^{31}$P grid was shifted with respect to the anatomical MRI and a mild spatial apodization (i.e., Fermi window with 90% diameter and 5% transition width) was applied prior to the inverse Fourier transform. The remaining processing steps were 100% automated. A 5 Hz exponential apodization was applied and the PME, phosphodiester (PDE), PCr, α-, γ-, and β-ATP, and inorganic orthophosphate (Pi), were modeled in the time domain with exponentially damped sinusoids and by omitting the first 2.75 ms of the free induction decay (FID) using the Marquardt-Levenberg algorithm. This approach ensured that the PME and PDE resonances primarily reflected the freely mobile, short correlation time (s-$\tau_c$), water soluble PME(s-$\tau_c$) and PDE(s-$\tau_c$) metabolites without the influence of relatively broad underlying signals within the PME and PDE spectral region. The PME(s-$\tau_c$) (i.e., phosphoethanolamine, phosphocholine, and inositol-1-phosphate) are predominantly building blocks of phospholipids and therefore, the relative concentrations of these metabolites are a measure of the active synthesis of membranes; the PDE(s-$\tau_c$) (i.e., glycerophosphocholine and glycerophosphoethanolamine) are major products of membrane degradation. To obtain intermediate correlation time (i-$\tau_c$) components within the PME and PDE spectral region, the FIDs were modeled a second time but with omitting the first 0.75 ms of the FID and then taking the difference between the PME and PDE amplitudes of the two modeled results. PME(i-$\tau_c$) moieties include less mobile molecules such as phosphorylated proteins and PMEs that are tightly coupled (in terms of MRS) to macromolecules [i.e., PMEs inserting into membrane phospholipids. PDE(i-$\tau_c$) moieties include less mobile PDEs that are part of small membrane phospholipid structures such as micelles, synaptic vesicles, and transport/secretory vesicles and PDE moieties coupled to larger molecular structures (i.e., PDEs inserting into membrane phospholipid structures. The right/left side effect was eliminated by averaging the signal from the two voxels, prior to fitting (which included correcting for phase and resonance frequency). Additionally, metabolite levels are expressed as a mole % relative to the total $^{31}$P signal.

The statistical analysis was done using the Statview (SAS Institute, Inc.) software package. The pearson t correlation test used to correlate between variables.

The two elderly depressed subjects were diagnosed with MDD according to DSM-IV criteria. No previous antidepressant medications were taken by the subjects in the three months prior to the study. Subject #1 has baseline, 6 and 12 week HDRS scores of 15, 1 and 0 and subject #2 had scores of 20, 17, and 3, respectively. Thus both depressed subjects were clinically improved at endpoint, fulfilling criteria for remission (HDRS<8). Medical conditions diagnosed in the depressed subjects included s/p knee arthroscopy, s/p cervical disk removal, hearing loss and benign prostatic hypertrophy in subject #1 and benign prostatic hypertrophy in subject #2. No clinically significant abnormalities were found in the laboratory exams and EKG of either depressed subject. Baseline, 6, and 12 weeks CIRS were 7, 6, and 5 for subject #1; and 4, 4, and 2 for subject #2, respectively. The change reflects the improvement of depressive symptomatology. Side effects from ALCAR treatment were mild and included dry mouth in subject #1 and a slight increase in perspiration in subject #2.

FIG. 1 shows the correlation of PME($s$-$\tau_c$) ($r$=0.86, $p$=0.069 and PCr ($r$=0.97, $p$=0.002) levels from the prefrontal region with HDRS scores for both depressed subjects.

FIG. 2 illustrates the prefrontal and basal ganglia PCr and PME($s$-$\tau_c$) levels at baseline, 6 and 12 weeks for the two depressed subjects and the mean PCr and PME($s$-$\tau_c$) levels for the six normal controls.

Unfortunately, the 6 week $^{31}$P MRSI session for subject #1 produced poor quality, unacceptable data and this time point is missing from the graphs. Baseline prefrontal PME($s$-$\tau_c$) levels in the depressed subjects were 1.5 to 2.0 SD higher than the mean of the controls and this increase was normalized with ALCAR treatment. Both depressed subjects had prefrontal PCr levels one SD higher than the mean of controls and ALCAR treatment further increased PCr levels by 27% and 31%, respectively. Similar changes in PME($s$-$\tau_c$) and PCr levels also were observed in the basal ganglia region (FIG. 2), but these metabolite levels did not correlate with HDRS scores. Although the most marked changes occur in the prefrontal region, z-score plots of the significant PME($s$-$\tau_c$) and PCr changes between depressed subjects and controls illustrates the other brain regions also undergo changes with ALCAR treatment. FIG. 3 demonstrates that compared with normal subjects, the two untreated depressed subjects at baseline had increased levels of PME($s$-$\tau_c$) in the prefrontal region ($p$=0.006). After 12 weeks of ALCAR treatment, the PME($s$-$\tau_c$) are normalized in the prefrontal regions but elevated in the superior temporal regions ($p$=0.05. In addition, PCr levels are elevated in the prefrontal ($p$=0.001), basal ganglia ($p$=0.022), and occipital ($p$=0.027 regions after 12 weeks of ALCAR treatment. There were no significant changes in the other metabolite levels.

While not wishing to be bound by any particular theory, the above findings suggest that beneficial clinical effects of acetyl-L-carnitine appear to be associated with changes in brain prefrontal PME($s$-$\tau_c$) and PCr levels. In the prefrontal region, the depressed subjects compared with controls after 12 weeks of ALCAR treatment show normalization of PME ($s$-$\tau_c$) and elevation of PCr levels.

The PME($s$-$\tau_c$) resonance is predominantly composed of phosphocholine, phosphoethanolamine and inositol-1-phosphate which are precursors in membrane phospholipid metabolism. The increased PME($s$-$\tau_c$) in depression, as also observed by others is not fully understood and will require further study. ALCAR treatment seems to restore PME($s$-$\tau_c$) levels to normal and there was a trend for the decreasing PME levels to correlate with clinical improvement. In the prefrontal region, twelve weeks of ALCAR treatment also elevated PCr, a high-energy phosphate metabolite which is an immediate precursor of ATP.

Compared with the control group, similar findings were observed for basal ganglia PME($s$-$\tau_c$) and PCr levels, but the metabolite levels did not correlate with HDRS scores. This may be due to the small number of depressed patients analyzed. Other brain regions may be affected by depression and these changes may be altered by ALCAR treatment (FIG. 3).

Acetyl-L-Carnitine (ALCAR) Results

MDD is a major, world-wide health problem. There is a need for new treatment approaches that have a wide margin of safety and can speed the onset to remission and reduce the rate of recurrence in this major mental health problem. In addition, the molecular and metabolic factors that underlie MDD and contribute to the slow and variable treatment response are further identified. Since ALCAR has demonstrated beneficial effects on neurodegenerative processes as well as beneficial effects on energy metabolism, membrane structure/function/metabolism, and neurotrophic effects, it is used in treatement of MDD. Many of the metabolic and molecular processes in adolescent and non-geriatric subjects are altered by ALCAR and thus are amenable to ALCAR treatment.

ALCAR treatment decreases levels of phosphomonoesters (PME) and increases levels of phospocreatine (PCr) in a brain of an adolescent or non-geriatric human subject with depression or bi-polar depression. ALCAR also produces beneficial changes to membrane phospholipid and high-energy phosphate metabolism in a brain a brain of an adolescent or non-geriatric human subject with depression or bi-polar depression.

What is meant by a pharmacologically acceptable salt of ALCAR is any salt of the latter with an acid that does not give rise to toxic or side effects. These acids are well known to pharmacologists and to experts in pharmaceutical technology.

One preferred form of daily dosing of ALCAR for clinical use is a composition comprising an amount of an acetyl L-carnitine, preferably equivalent to 0.1 to 3 g, and preferably 0.5 to 3 g per day.

ALCAR does not appear to induce mania in animal models or in clinical trials to date. Since animal and basic science studies demonstrate that ALCAR shares several important molecular mechanisms with lithium, but without lithium's potential toxicity, ALCAR could provide prophylactic effects against suicidality. Given ALCAR's similarity to lithium at several molecular mechanistic levels, ALCAR is effective in treating bipolar depression and preventing recurrent episodes. Long-term therapy of MDD with therapeutic agents that have molecular properties that slow or reverse neurodegenerative changes as well as behavioral changes is desirable. ALCAR is one such therapeutic agent. Few existing $^{31}$P and $^1$H MRSI studies of MDD provide findings for compounds which demonstrate both membrane phospholipid and high-energy phosphate changes in the brain of individuals with MDD. However, new studies with ALCAR demonstrate such changes (see below). Since ALCAR can interact with both cholinergic and serotonergic neurotransmitter systems, it will modulate neurobiological and psychobiological activities controlled by these two neurotransmitter systems. This partially explains ALCAR's antidepressant activity.

Effect of ALCAR on Brain Metabolic Response to Brief Energetic Stress

ALCAR has been shown to provide a protective effect in several animal models of brain energetic stress. ALCAR also has been shown to be an effective treatment of MDD which is associated with neurodegenerative and metabolic changes consistent with energetic stress.

Figure 4:
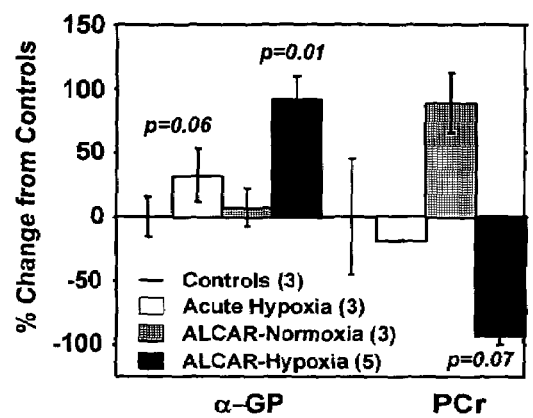
FIG. 4 is a block diagram illustrating an effect of ALCAR on in vitro $^{31}$P MRS α-GP and PCr levels under hypoxic (30 seconds) and normoxic conditions in Fischer 344 rats.

FIG. 4 is a block diagram illustrating an effect of ALCAR on in vitro $^{31}$P MRS α-GP and PCr levels under hypoxic (30 seconds) and normoxic conditions in Fischer 344 rats.

Figure 5:
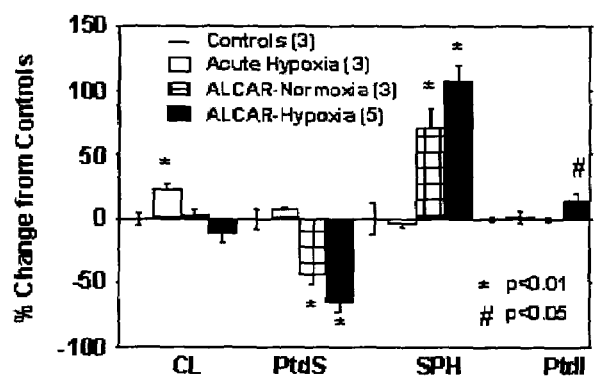
FIG. 5 is a block diagram illustrating an effect of ALCAR on in vitro $^{31}$P MRS phospholipid levels under hypoxic and normoxic conditions in Fischer 344 rats.

FIG. 5 is a block diagram illustrating an effect of ALCAR on in vitro $^{31}$P MRS phospholipid levels under hypoxic and normoxic conditions in Fischer 344 rats.

The rat brain responds differentially to brief energetic stress (30 seconds of hypoxia) depending on the age of the animal. The effect of ALCAR (75 mg/kg animal weight injected intraperitoneally 1 hour before sacrificing the animal) on both normoxic rat brain and rat brain exposed to brief hypoxia (30 seconds) was investigated (FIGS. x and x). These studies were conducted on aged rats (30 months) to provide possible insights into human aged brain and MDD. While ALCAR under normoxic conditions (ALCAR/normoxia) did not alter α-GP levels, under ALCAR/hypoxia conditions, the α-GP levels were elevated higher (approximately +80% compared with controls, p=0.01) than under 30 seconds of hypoxia alone (approximately +25% compared with controls, p=0.06). Mirror-image findings were observed for PCr levels which decrease with hypoxia (non-significant), increase with ALCAR/normoxia (non-significant), and decrease with ALCAR/hypoxia (non-significant, p=0.07)(FIG. 4).

The findings for brain phospholipids are particularly striking (FIG. 5) given the brevity of the hypoxia. Cardiolipin levels are increased (approx. +20%) after 30 seconds of hypoxia ($p<0.01$), are unchanged with ALCAR/normoxia, and non-significantly reduced with ALCAR/hypoxia. Phosphatidylserine (PtdS) levels are unchanged with hypoxia but are decreased with both ALCAR/normoxia (approx. −50%, $p<0.01$) and ALCAR/hypoxic (approx. −75%, $p<0.01$).

These studies provide direct evidence for ALCAR effects on brain membrane phospholipid metabolism and the NADH/α-GP shuttle pathway under conditions of normoxia (PtdS, SPH) and brief hypoxia (α-GP, PtdS, SPH, PtdI). These mechanisms are also important in human clinical conditions that involve brain aging and possible energetic stress such as MDD.

In Vivo $^{31}$P MRS Findings in Two Young Subjects With MDD

Figure 6:
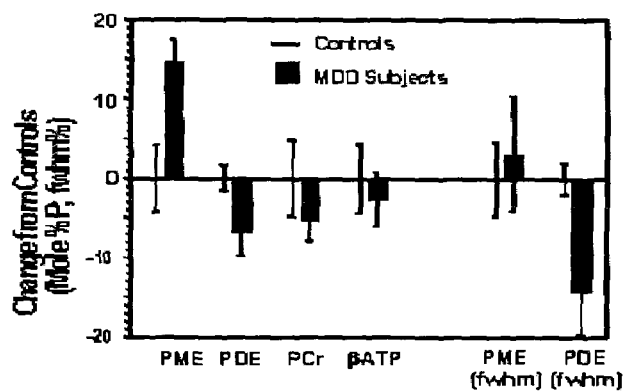
FIG. 6 is a block diagram illustrating a percent change of in vivo $^{31}$P MRSI metabolite levels and PME, PDE linewidths [full width at half maximum (fwhm)] of 2 MDD subjects compared with 13 control subjects.

FIG. 6 is a block diagram illustrating a percent change of in vivo $^{31}$P MRSI metabolite levels and PME, PDE linewidths [full width at half maximum (fwhm)] of 2 MDD subjects compared with 13 control subjects.

As part of an ongoing $^{31}$P-$^{1}$H MRSI study of never-medicated, first-episode schizophrenia subjects three $^{31}$P MRSI spectra on 2 MDD subjects (1 Asian male, 1 white female, 24∀2.3 years) were obtained. The MDD spectral results are compared with those obtained from 13 controls (6 males; 3 white, 2 African-American, 1 Asian and 7 females; 4 white, 3 African-American; 21∀1.0 years). PME levels in the MDD subjects were increased by approximately 15% (p=0.13) while there were decreases in the levels of PDE (approx. −7%; p=0.08), PCr (approx. −5%, p=0.61), and β-ATP (approx. −3%, p=0.87) (FIG. 6). Treatment with ALCAR lowered PME levels in the MDD subjects. Of note is that the PDE linewidth is decreased by approximately −15% suggesting the loss of PDE moieties is mostly those with i-$\tau_c$ such as synaptic vesicles. These findings suggest molecular alterations related to both membrane phospholipid and high-energy metabolism in these subjects.

The methods describe herein treat depression and bi-polar depression with ALCAR, thereby avoiding unwanted side-effects exhibited by conventional antidepressant agents. ALCAR also helps prevents recurrent episodes of depression and bi-polar depression.

Bioengineering of LCAR and ALCAR

LCAR is important in the β-oxidation of fatty acids and ALCAR contains carnitine and acetyl moieties, both of which have neurobiological properties. The acetyl moiety of ALCAR can be used to maintain acetyl-CoA levels. Other reported neurobiological effects of ALCAR include modulation of: (1) brain energy and phospholipid metabolism; (2) cellular macromolecules including neurotrophic factors and neurohormones; (3) synaptic morphology; and (4) synaptic transmission of multiple neurotransmitters. Potential molecular mechanisms of ALCAR include: (1) acetylation of —$NH_2$ and —OH functional groups in amino acids and N-terminal amino acids in peptides and proteins resulting in modification of their structure, dynamics, function and turnover; and (2) acting as a molecular chaperone to a larger molecule.

There is data demonstrating that ALCAR can acetylate lysine 28 in the Aβ(1-40) peptide derived from the ubiquitous protein, amyloid precursor protein. ALCAR is reported to have neuroprotective effects (Pettegrew et al., 2000) and could become recognized as a dietary component important to mental health—particularly in older populations. ALCAR has therapeutic indications for Alzheimer's disease (Pettegrew et al., 1995); geriatric depression (Pettegrew et al., 2002); schizophrenia (Masterson and Wood, 2000); and perhaps other mental heath disorders.

In vivo phosphorus MRS metabolomic studies have permitted examination of molecular indicators of pathophysiology in vivo, and the impact of novel treatments (e.g., ALCAR) upon such targets. Geriatric depression is a significant world-wide mental health problem and ALCAR could provide considerable therapeutic benefit.

Figure 7:
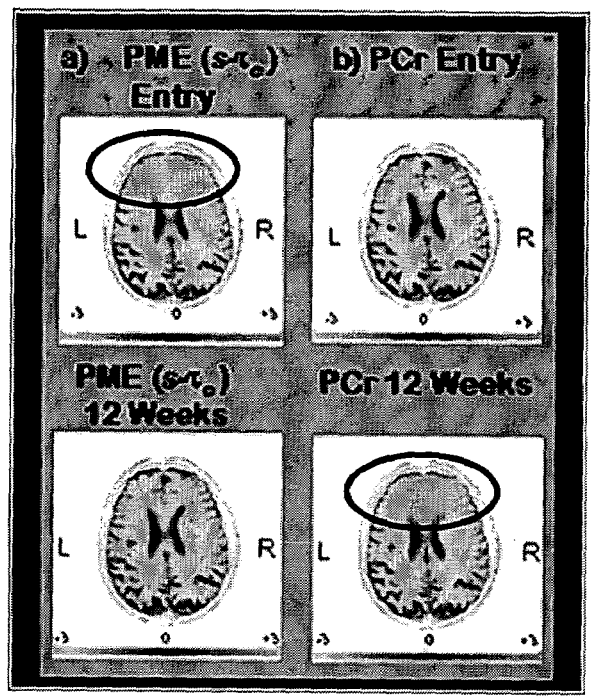
FIG. 7 is a block diagram illustrating a scan of human brain illustrating therapeutic response to ALCAR for depression.

FIG. 7 is a block diagram illustrating a scan of human brain 44 illustrating therapeutic response to ALCAR for depression. Z scores indicated by a color scale of the two mildly depressed subjects compared with six controls at entry and 12 weeks for (a) PME(s-$\tau_c$) and (b) PCr metabolite levels. Only Z scores greater than 3 are shown.

FIG. 7 at (a) illustrates higher PME levels (top right circle) and a lower PCr levels. FIG. 7 at (b) illustrates lower PME levels and higher PCr levels (bottom left circle) after treatment with ALCAR.

Environmentally directed bioprocess engineering alter plant genome expression allowing the production of molecules that the plant normally would not produce or would produce in very limited quantities. This approach allows genome expression to be altered without alteration of the genome itself. One embodiment of the invention demonstrates the ability to turn on gene expression in sunflower seeds via environmental bioprocess engineering to produce LCAR and ALCAR, two molecules that by all published accounts are either not normally made in plants or made in very limited quantities.

Figure 8:
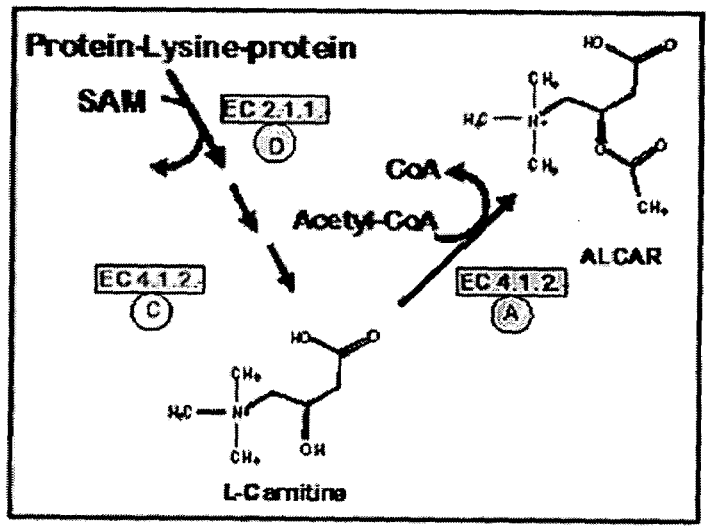
FIG. 8 is a block diagram illustrating an exemplary pathway for ALCAR formation.

FIG. 8 is a block diagram illustrating an exemplary pathway 46 for ALCAR formation. In FIG. 8, S-adenosylmethionine is abbreviated as "SAM."

Methods for Producing LCAR and ACLAR from Plant Seeds

Figure 9:
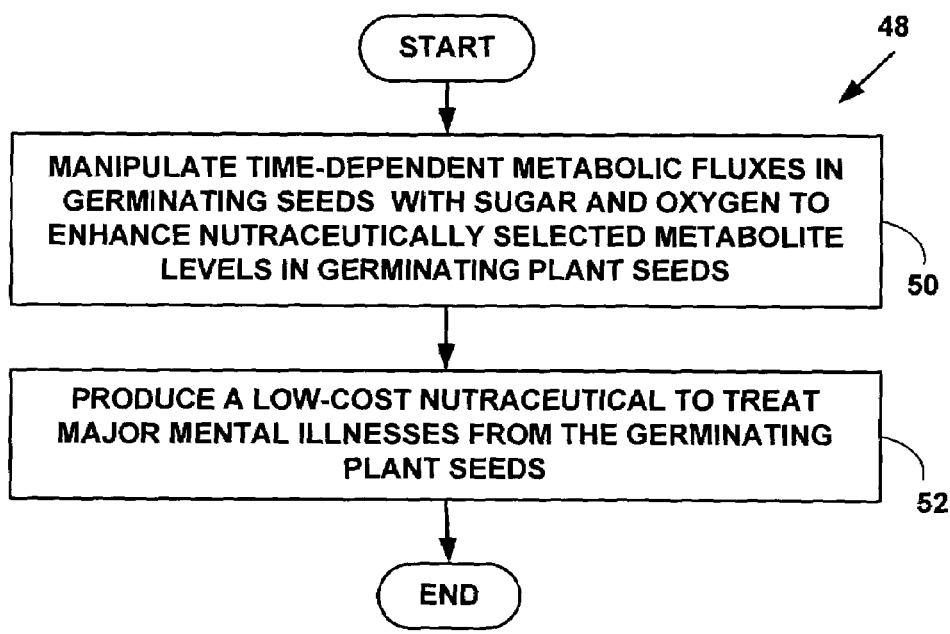
FIG. 9 is a flow diagram illustrating a method for producing a nutraceutical for human consumption.

FIG. 9 is a flow diagram illustrating a Method 48 for producing a nutraceutical for human consumption. At Step 50, time-dependent metabolic fluxes in plural germinating seeds are manipulated with sugar and oxygen to enhance nutraceutically selected metabolite levels in the plural germinating plant seeds. At Step 52, a low-cost nutraceutical to treat major mental illnesses is produced from the plural germinating plant seeds.

Method 48 is illustrated with an exemplary embodiment. However, the present invention is not limited to this exemplary embodiment and other embodiments can also be used to practice the invention.

In such an exemplary embodiment, at Step 50 time dependent metabolic fluxes are manipulated by bioprocess engineering control of environmental and physiological conditions to optimize LCAR and ALCAR formation in germinating seeds. A metabolic flux network and conduct time-dependent metabolite measurements are developed to demonstrate the influence of germination conditions on fatty acid and membrane phospholipids metabolism and mitochondrial energy production all of which influence LCAR and ALCAR production resulting in an approximate 1000-fold increase in the production of LCAR and ALCAR by germinating sunflower seeds.

In one embodiment, Step 50 includes a translational metabolomic approach for manipulating time-dependent metabolic fluxes in germinating seeds in order to enhance nutraceutically important metabolite levels in plant seeds.

At Step 52, a low-cost nutraceutical is produced including LCAR and ALCAR to treat major mental illnesses.

Plant-based methods are targeted over livestock-based methods since plant production is more economically favorable, especially for poor countries. The plasticity of gene expression in plants, ease of manipulating plants and the integral role of plants in human nutrition and health makes plant tissue an ideal candidate for developing metabolomics techniques. Dramatic shifts in seed metabolic fluxes can be accomplished with changes in seed germination environment.

A human nutraceutical is produced while gaining a better understanding of plant metabolism (which is the source of all human nutrition). LCAR and ALCAR are ideal candidates for a metabolomics approach to biomolecular engineering of plant nutraceuticals because they are linked to primary metabolism—not a "terminal" secondary metabolite. In addition, the association of this study with understanding acetyl-CoA in plants has broader implications to genetic engineering strategies in plants because of the prevalence of this co-factor in plant biochemistry.

In mammalian systems, carnitine is required for transport of fatty acids across the inner mitochondrial membrane for energy production via β-oxidation, and the acetyl moiety can be used to maintain acetyl-CoA levels (Iacobazzi et al., 1998).

In one embodiment, at Step 50 the sugar includes sucrose, the oxygen includes at least 40% $O_2$ and the plural germinating plant seeds include plural germinating sunflower seeds.

In one embodiment, at Step 50 the manipulating step includes enhancing fatty acid β-oxidation inside a plurality of mitochondrial matrixes with sucrose suppression of a plurality of glyoxylate cycles in the plurality of germinating plant seeds stimulating mitochondrial β-oxidation of the fatty acids in the plurality of germinating plant seeds with $O_2$.

In one embodiment, at Step 50, bioprocess engineering approaches are used to enhance production of the nutraceutical ALCAR as well as LCAR in germinating seeds.

Figure 10:
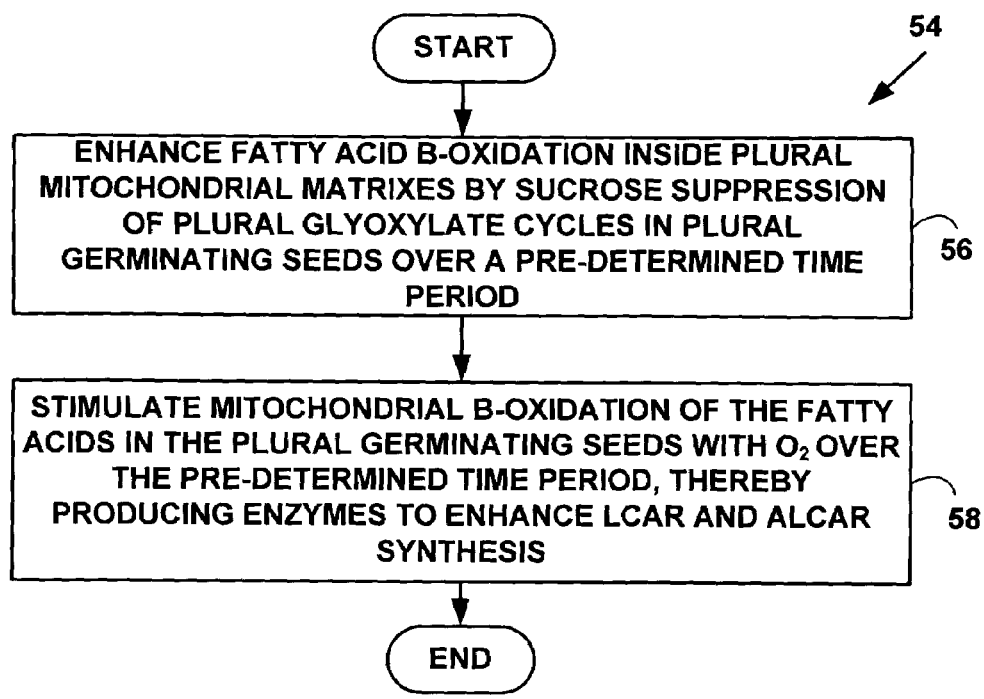
FIG. 10 is a flow diagram illustrating a method for producing LCAR and ALCAR.

FIG. 10 is a flow diagram illustrating a Method 54 for producing L-carnitine (LCAR) and acetyl-L-carnitine (AL-CAR). At Step 56, fatty acid β-oxidation is enhanced inside plural mitochondrial matrixes by sucrose suppression of plural glyoxylate cycles in plural germinating seeds over a pre-determined time period. At Step 58, mitochondrial β-oxidation of the fatty acids is stimulated in the plural germinating seeds with $O_2$ over the pre-determined time period, thereby producing enzymes to enhance LCAR and ALCAR synthesis.

Method 54 is illustrated with an exemplary embodiment. However, the present invention is not limited to this exemplary embodiment and other embodiments can also be used to practice the invention.

In such an exemplary embodiment at Step 56, fatty acid β-oxidation is enhanced inside a mitochondrial matrix of a seed genome by sucrose suppression of the glyoxylate cycle for a pre-determined time period. At Step 58, mitochondrial β-oxidation of fatty acids is stimulated with $O_2$ for the pre-determined time period. With enhanced mitochondrial β-oxidation, which needs LCAR as a fatty-acid transporter across the inner mitochondrial membrane, the seed genome will be turned on to produce proteins (enzymes) needed to enhance LCAR synthesis. With increased LCAR production and enhanced β-oxidation of fatty acids, increased ALCAR is also produced.

Figure 11:
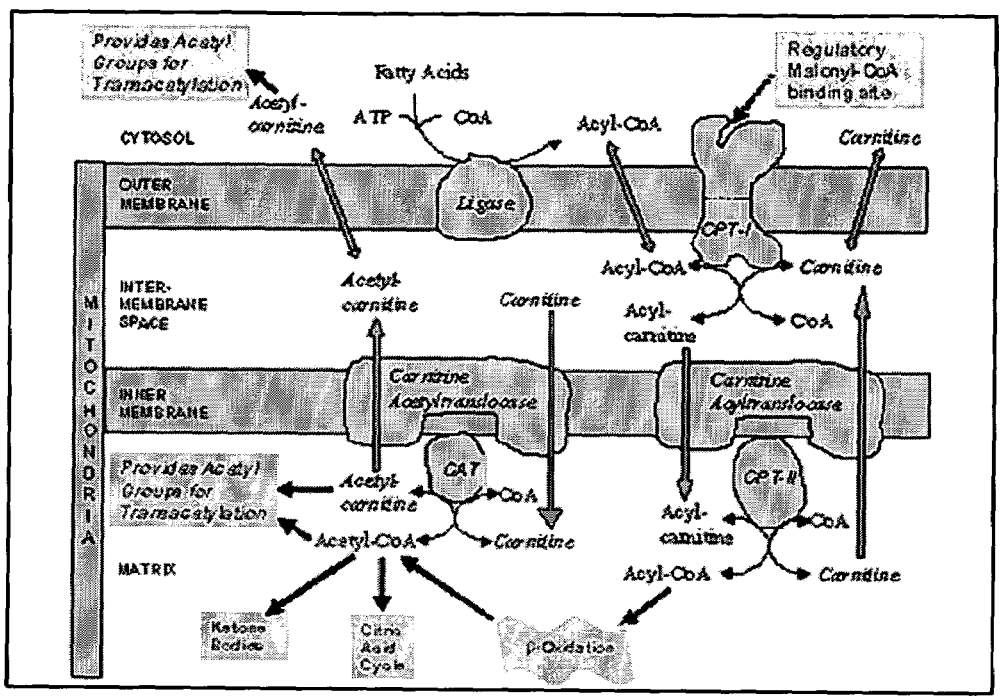
FIG. 11 is a block diagram illustrating a role of mitochondrial carnitine and ALCAR in shuttling free and acyl carnitines across the inner mitochondrial membrane.

FIG. 11 is a block diagram 60 illustrating a role of mitochondrial carnitine and ALCAR in shuttling free and acyl carnitines across the inner mitochondrial membrane. In FIG. 11, carnitine palmitoyl transferase is abbreviated "CPT" and carnitine acetyltransferase is abbreviate "CAT."

A complicating factor in interpreting experimental data in plants is the glyoxylate cycle—which is a short-circuited form of the tricarboxylic acid (TCA) cycle that is present in the glyoxysomes (Salon et al., 1988; Raymond et al., 1992). A recent study of the glyoxylate cycle in an Arabidopsis mutant knockout has definitely shown that plants can respire fatty acids (Eastmond et al., 2000). This combined with measurements of β-oxidation enzymes in mitochondria (Bode K et al., 1999) and acylcarnitine transferase activity in mitochondrial membranes (Thomas and Wood, 1986) demonstrates that carnitine dependent transport of fatty acids takes place in plant mitochondria as shown in FIG. 12 but is usually thought to play a very minor role.

Mitochondrial β-oxidation of fatty acids favors energy production. For example, the complete β-oxidation of palmitic acid in mitochondria produces a net 129 ATPs while β-oxidation and gluconeogenesis via the glyoxysomes produce a net 8 ATPs [see (Lehninger et al., 1993 pp 488-490; Mohr and Schopfer, 1995)]. In contrast, glyoxysomal β-oxidation produces "building blocks" for growth; succinate is produced from glyoxysome-generated acetyl-CoA and glucose is produced via gluconeogenesis. Beyond expediting gluconeogenesis in plants, the rationale for utilization of the energy inefficient glyoxylate pathway is not obvious.

Figure 12:
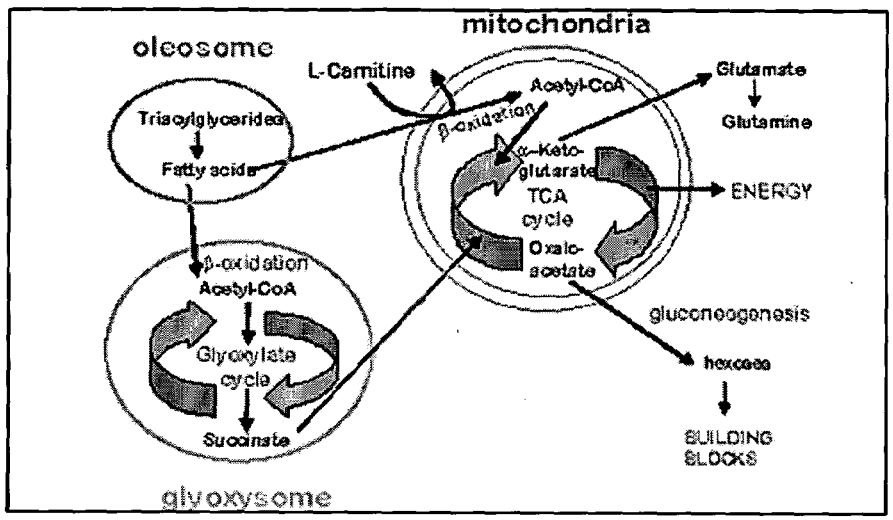
FIG. 12 is a block diagram illustrating Fatty acid β-oxidation via L-carnitine dependen tricarboxylic acid (TCA) cycle in mitochondria (respiration) and Lcarnitine independent glyoxylate cycle (gluconeogenesis).

FIG. 12 is a block diagram 62 ilustrating illustrates Fatty acid β-oxidation via L-carnitine dependent tricarboxylic acid (TCA) cycle in mitochondria (respiration) and L-carnitine independent glyoxylate cycle (gluconeogenesis).

The observation that the presence of sugar in the germination medium can reduce rather than enhance germination rate shows that there is complicated crosstalk between the competing demands of fatty acid catabolism for energy and growth.

The invention demonstrates physiological conditions that enhance energy-producing metabolic fluxes from fatty-acid catabolism that favor LCAR and ALCAR formation. Plant seeds were used because of their unique physiology and biochemistry (as well as their availability and importance to human nutrition). A survey of ALCAR levels in eukaryotic tissues provides insight into the physiology.

LCAR is present in mammalian cells and tissues in relatively high concentrations as either free LCAR (beef steak 592±260:mol/100 g) or as acyl-carnitines including ALCAR at concentrations approximately 10% of LCAR concentrations (Broquist, 1994). LCAR and ALCAR concentrations are much lower in plants (LCAR in:wheat seed 2.5 :mol/10 g; wheat germ 7.4 :mol/100 g; oat seedling 8.6 :mol/100 g; and avocado mesocarp 29.6 :mol/100 g) (Panter and Mudd, 1969). The lower ALCAR levels in plants likely reflect a reduced dependence of plants on mitochondrial energy production from fatty acids. Since fatty acids must be converted to acyl-carnitines to cross the inner mitochondrial membrane, it is desirable to facilitate the flux from plant fatty acid reserves into the mitochondria. This will take place when there is a high energy demand and oxygen is available to support β-oxidation.

While plant tissues are generally low in fat content (<1 wt %), oils are often accumulated to high levels in seeds which can sustain a high flux of fatty acids to respiration. Seed oil storage varies considerably as is illustrated by Table 1. Percent Oil and (non-fiber) carbohydrate (CHO) content of plant seeds (wt % dry seed) is illustrated in Table 1.

TABLE 1

| Plant Seed | Oil | CHO | Plant Seed | Oil | CHO | Plant Seed | Oil | CHO |
|---|---|---|---|---|---|---|---|---|
| Pecan | 72 | 12 | Sunflower | 47 | 16 | Wheat | 2.0 | 70 |
| Walnut | 60 | 13 | Soybean | 18 | 28 | Rice | 1.9 | 76 |
| Safflower | 60 | 12 | Corn (high oil) | 7.0 | 69 | Cowpea | 1.5 | 57 |
| Peanut | 48 | 16 | Corn (hybrid) | 3.0 | 72 | Pea | 1.3 | 65 |

In one embodiment, sunflower seeds are specifically chosen because lipid reserves are stored in the cotyledons (not endosperm). Storage within the seedling tissue reduces the need for carbon transport, which would have to be in the form of sucrose (and require gluconeogenesis). Respiration rates can be manipulated by controlling the environment in which the seeds germinate. The small surface area to tissue volume results in oxygen transport limitations in seeds (Girton, 1979). Therefore the initial strategy for flux manipulation was to increase oxygen partial pressure around germinating seeds. It was also desirable to feedback repress gluconeogenesis (see FIG. 12), to minimize fatty acid metabolism through the LCAR-independent glyoxylate cycle.

Control of gluconeogenesis is mediated by fructose 2,6-bisphosphate which mediates photosynthesis and respiration depending on energy and glycolytic metabolites (Smith, 1999). A large shift in seed energetics that results from this approach. To accomplish this bioprocess engineering approach to manipulating fluxes, it is necessary to carry out germination in bioreactors that have well-defined and controllable environmental conditions.

Several lines of evidence indicate that sunflower seed germination is limited by nutrient flux mobilization from seed reserves: Sunflower seed germination (radicle emergence) took 24-hours over a 20° C. range (20-40° C.), a temperature range where enzymes would experience a large change in intrinsic activity. Prototype laminar flow germination chambers were constructed for respiration studies; in these chambers the rate of germination was shown to be indistinguishable for air (21% $O_2$) and 50% oxygen.

Oxygen-independent radicle extension rates of 1.75 mm/day were observed, which are dramatically slower than roots grown heterotrophically where meristem extension is highly oxygen limited [5 mm/day; (Asplund and Curtis, 2001)].

The methods described herein provides precise control over germination of seeds. Sunflower seeds were sterilized as follows using a plant surface sterilization kit (e.g., purchased from Q.BIO gene, CA) containing solutions A and B. Sunflower seeds contain dirt or other contaminants; therefore, they were rinsed with deionized water. After rinsing in water seeds were submerged in sterilization solution A (5 seeds in 25 ml sol.A). Seeds were incubated for 5-7 minutes with gentle stirring at room temperature. The majority of the liquid decanted into a waste container using caution that the sample is not lost. The seeds, treated with solution A, were added to solution B (50 ml) and stirred slowly (100 rpm) with a magnetic stirrer for 15 minutes. The solution was decanted and discarded. The seeds, after treatment with solutions A and B were stirred in 100 ml sterile distilled water and incubated at room temperature for 5 minutes with gentle stirring. The residual liquid was decanted off and the seeds were washed with sterile distilled water 2 more times.

The sterile sunflower seeds were transferred to dry, sterile Erlenmeyer flasks (7 grams in each flask) equipped with airtight septums with gas traps for purging of gases. The set of experiments and germination conditions were as below: Flask A: Sterile sunflower seeds (10 gms, wet weight) plus deionized water (100 ml) Flask B: Sterile sunflower seeds (10 gms, wet weight) plus 2% w/v sucrose (100 ml). A controlled and highly regulated stream of air was purged into flask A which also pass through the flask B and finally the outlet of flask B was purged in a water reservoir to monitor the continuous flow of the air through the both flasks. It was continued for 60 hours.

After, 24 hours the solution becomes hazy and light yellow/brown colored. Seeds germination become visible between 36-48 hours. After 60 hours, the water and sucrose solution was decanted off and the residual seeds washed 3-4 times (100 ml each time) with distilled water. Flask C: Sterile sunflower seeds (10 gms, wet weight) plus deionized water (100 ml) Flask D: Sterile sunflower seeds (10 gms, wet weight) plus 2% w/v sucrose (100 ml) A controlled and highly regulated stream of ultra pure oxygen was purged into flask C which also passes through flask D and finally the outlet of flask D was purged in a water reservoir to monitor the continuous flow of oxygen through the both flasks. It was continued for 60 hours.

After 20 hours the solution became hazy and light yellow/brown colored. Seed germination becomes visible between 40-48 hours. After 60 hours, the water and sucrose solution was decanted off and the residual seeds were washed 3-4 times (100 ml each time) with distilled water. Each sample for subsequent extraction and NMR analysis requires ~150 seeds. Studies were carried out in triplicate in shake flasks with an aseptic flush of gas of controlled composition. The flasks were flushed at intervals of 2 hours for the first 12 hours, 3 hours for the subsequent 12 hours and every 6 hours for the second and third day.

Dry and imbibed seeds: The PCA extraction method is similar to that described by Pettegrew et al. (Pettegrew et al., 1990b). Approximately one gram of sunflower kernels are weighted out, then ground in a mortar and pestle at liquid $N_2$ temperatures. The powder is placed in a glass beaker sitting in an insulated box with liquid $N_2$. Twenty-five ml of 1M $HClO_4$ is powdered and added to the seed kernel powder. The two powders are mixed and the beaker is allowed to come to −40° C. and placed in a centrifuge tube and spun down at 18,000 rpm for 30 minutes. The supernatant is removed with oil floating on the surface. A pH is adjusted to pH 7.0 with KOH and spun again at 18,000 for 30 minutes. The supernatant is lyophilized.

Germinated seeds: Extraction of sprouted sunflower seeds with PCA is similar to the PCA extraction of dry sunflower seeds except the sprouted seeds are quick frozen in liquid $N_2$ and ground in a mortar and pestle at −80° C. to preserve the high-energy phosphate metabolites.

Seeds incubated in sucrose: The seeds incubated in sucrose are extracted the same as the procedures for dry and imbibed seeds as well as sprouted seeds described above.

A modified Folch procedure (Meneses and Glonek, 1988) is used to extract phospholipids from dry, imbibed, germinated and sucrose incubated sunflower seeds. Approximately 1 gram of sunflower kernels are weighed, and placed in a ground glass homogenizer with 15 ml of extraction solvent (5 ml methanol plus 10 ml chloroform containing 150 mg/L BHT) and 9.48 :1 of a solution [150:1 of tris(2-butoxyethyl) phosphate (94%) diluted with 2.85 ml of $CHCl_3$] for an internal $_{31}P$ NMR standard. The mixture is homogenized and eluted through a glass wool column into a 50 ml round bottom flask. 3.75 ml of an aqueous salt solution (0.04% $CaCl_2$, 0.034% $MgCl_2$, 0.74% KCl) is added and vortexed. The mixture is spun in a Dynac table top centrifuge for 10 minutes at low speed. The top phase is removed and discarded. The theoretical upper phase is used to wash (3 times total) the sample without disturbing the lower phase. The lower phase is dried under Argon. The sample is then available to be taken up in the NMR solvent.

After germination, the wet sunflower seeds were cooled to −70° C. and ground in a motor and pestle at liquid $N_2$ temperatures. The fine powder was transferred to a paper thimble, which fits in the Soxhlet apparatus.

Selection of extraction solvent: In order to extract the phytoconstituents and other nutraceuticals based on their polarity and physiochemical properties, we have chosen following three solvents in order of their increasing polarity: (1) Hexane (Dieletric constant 1.89, Polarity 0.10); (2) Methylene chloride (Dieletric constant 9.08, Polarity 3.10); and (3) Methyl alcohol ((Dieletric constant 36.6, Polarity 5.10).

Figure 13:
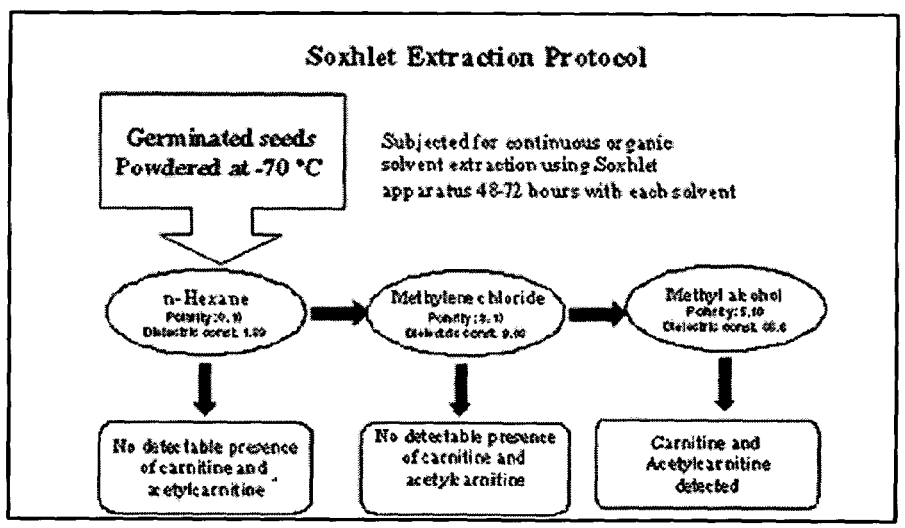
FIG. 13 is a block diagram illustrating an exemplary Soxhlet extraction protocol for sunflower seeds.

FIG. 13 is a block diagram illustrating an exemplary Soxhlet extraction protocol 64 for sunflower seeds.

A Soxhlet apparatus, equipped with a cold-water condenser, is placed on the round bottom flask containing the selected solvent and a magnetic stirring bar. The flask is submerged in a temperature controlled oil bath. The designated solvents are added and heated in succession. The solvent vapor passes up through the outer tube of the apparatus, and condensed solvent then drips down through the thimble containing sunflower seeds. Metabolites are extracted out of the seeds into the hot solvent. Once the solution level reaches the top of narrow bent tube, the solution is automatically siphoned through the narrow tube into the round bottom flask where the extracted materials accumulates.

This technique is highly efficient since the same batch of solvent is recycled through the sunflower seeds. After 60 hours of continuous extraction, completion was monitored by thin layer chromatography. The extract thus obtained was concentrated in vacuum at 40° C. by rotatory evaporator. The same procedure was repeated with each solvent after collecting earlier extracts (FIG. 13). The light brown viscous oily mass obtained from the final extraction solvent (methanol) was derivatized by 1-aminoanthracene (AA) catalyzed by carbodiimide: 1-(3-dimethylaminopropyl)-3-ethylcarbodiimide for High Performance Liquid Chromatography (HPLC) and mass spectroscopic analysis.

Derivatization of LCAR and ALCAR with AA provides a highly sensitive method to quantify LCAR and ALCAR by HPLC.

Figure 14:
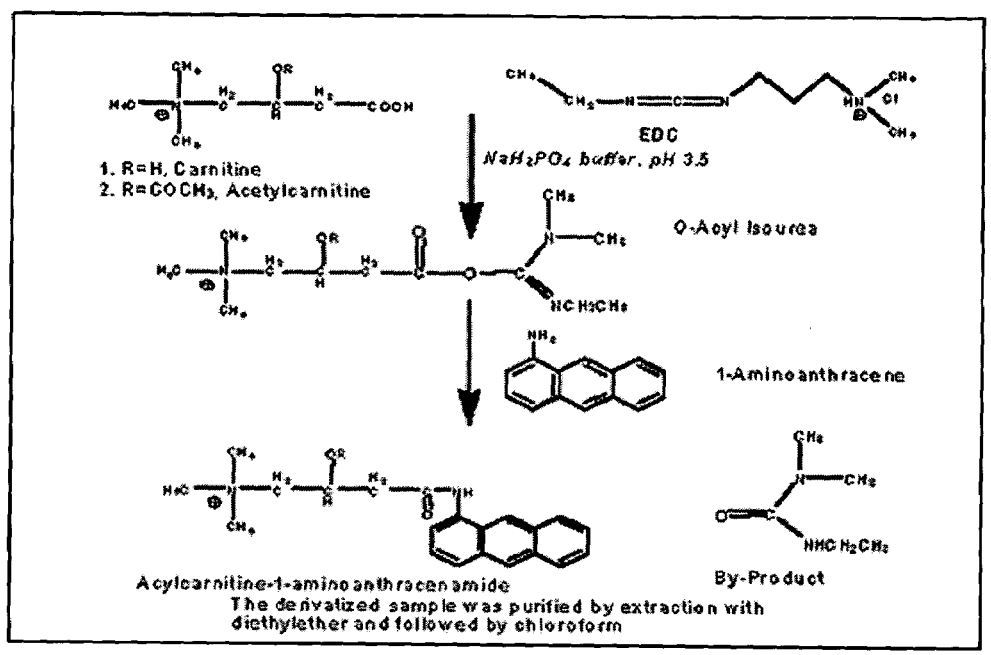
FIG. 14 is a block diagram of a chemical reaction for derivatization of acylcarnitines with 1-aminoanthracene.

FIG. 14 is a block diagram of a chemical reaction 66 for derivatization of acylcarnitines with 1-aminoanthracene. The reaction is catalyzed by 1-(3-dimethylaminopropyl)-3-ethylcarbodiimide (EDC).

The derivatization is catalyzed by the carbodiimide: 1-(3-dimethylaminopropyl)-3-ethylcarbodiimide (E.C.). To obtain AA derivatives, 100 mg of standard or seed extract was dissolved in 3.5 ml of 0.01M $NaH_2PO_4$ buffer (pH 3.5). To the above reaction mixtures was added 1 ml of EDC (142 mg/ml in 0.01M $NaH_2PO_4$ buffer of pH 3.5) (add 200:1 at a time while continuously vortexing the sample). After forming the EDC-activated moiety of the standards or extract components, 120:1 1.0 N hydrochloric acid was added slowly drop wise with continuous stirring.

Finally, the fluorescent reagent, AA, dissolved in acetone (7 ml, at a concentration of 16 mg /ml) was added to there action mixture. The reaction mixture incubated at 25° C. for 30-35 minutes. Upon conjugation the reaction was worked up by transferring the reaction mixture to a separating funnel and the aqueous reaction content was extracted with diethyl ether (2×5 ml) to remove the excess reagents and fluorescent tag. The aqueous layer was collected after separating the same from ether layer. The pH of the aqueous layer adjusted from 9.1 to 7.0 using 0.01 M $Na_2HPO_4$. Further, AA-conjugated molecules present in aqueous layer were purified by washing with chloroform (2×10 ml).

At this pH value the amides resulting from the reaction of amino acids with AA are highly soluble in chloroform, whereas the solubility of derivatives of carnitines in chloroform is negligible. After organic solvent washes, the aqueous layer thus obtained was lyophilized to obtain the solid conjugate which was desalted to get rid of buffer salts by dissolving the lyophilized material in methanol (25 ml) while stirring at room temperature for 15 minutes. The methanolic solution was filtered through 0.45:PTFE syringe filters and filtrate concentrated in vacuum at 40° C. to remove methanol from it. Finally, the semisolid mass thus obtained was dried in high vacuum at 25° C. in a desiccator containing anhydrous calcium chloride. The 1-aminoanthracene derivatives of LCAR and ALCAR standards and methanolic extracts of sunflower seeds were analyzed by HPLC and Electrospray Mass Spectrometry.

Determination of ALCAR and LCAR Content of Sunflower Seeds

In one embodiment, the HPLC is carried out using a Perkin-Elmer Series 200 Quaternary Pump with a Series 200 UV/VIS detector at 248 nm. The column is a Phenomenex Gemini C18, 5 micron, 110 A, 100×4.6 mm. The mobile phase is made up of 700 ml of a 0.1M ammonium acetate pH 3.5 plus 300 ml of acetonitrile. The flow rate is 1.3 ml/minute. The equilibration time is 5 minutes and the run time is 24 minutes. The sample is mixed 1:1 with 0.01 M Sodium phosphate buffer pH 3.5 and 10:1 is injected. Under these conditions LCAR elutes around 4.5 to 5.2 minutes whereas ALCAR elutes at 7.80-8.40 minutes.

Figure 15:
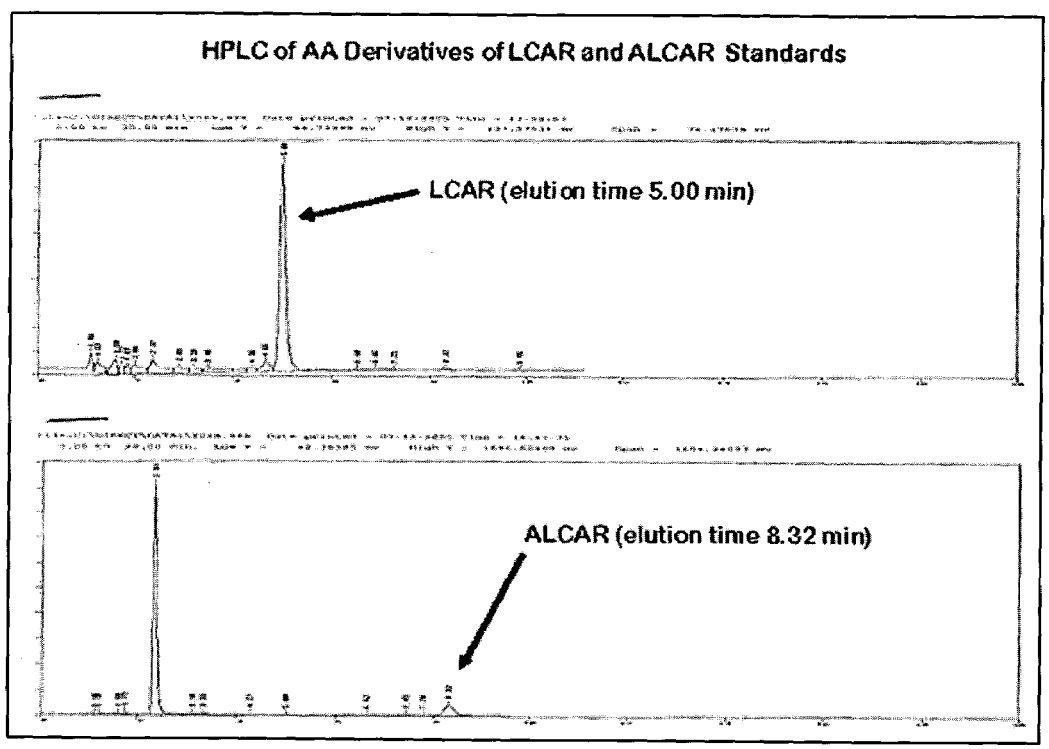
FIG. 15 is a block diagram illustrating HPLC of AA derivatives of standard LCAR and ALCAR.

FIG. 15 is a block diagram 68 illustrating HPLC of AA derivatives of standard LCAR and ALCAR.

Figure 16:
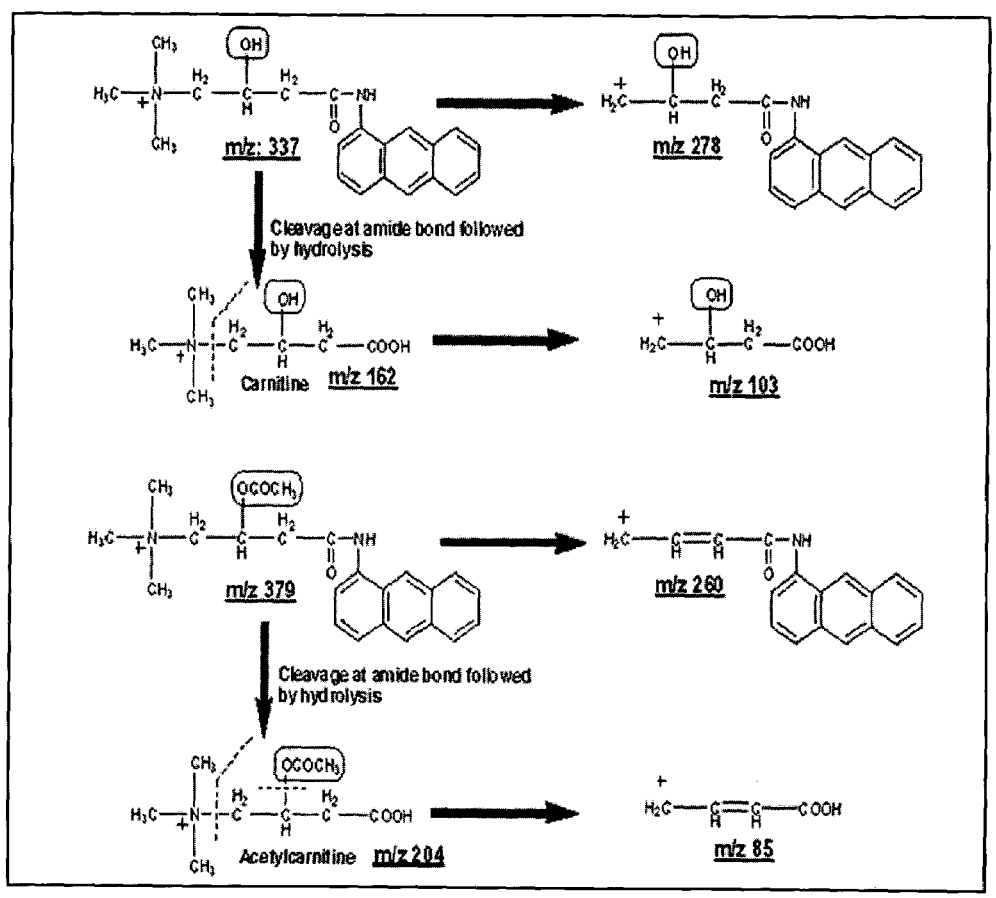
FIG. 16 is a block diagram illustrating selected ion structures possible from the AA derivatives of LCAR and ALCAR.

FIG. 16 is a block diagram 70 illustrating selected ion structures possible from the AA derivatives of LCAR and ALCAR;

Electrospray Mass Spectrometry was used to identify the AA derivatives of LCAR and ALCAR. The mass spectral studies were carried out with a Finnigan LCQ which is a quadrupole field ion trap mass spectrometer with electrospray ionization and atmospheric pressure chemical ionization sources using helium as the collision gas. Mass and their fragmentation spectrum of the molecular ions of the 1-aminoanthracene derivatized carnitine, acetylcarnitine and methanolic extract (seeds germinated under $O_2$/sucrose conditions) were obtained with the MS/MS mode within the range of 80-600.

The mass spectral analysis of samples show molecular ion peaks of m/z 337 and m/z 379 corresponding to the AA-derivatized LCAR and ALCAR, respectively.

Upon fragmentation of AAderivatized LCAR, loss of trimethylamine (m/z 59) from the parent molecule was observed giving an m/z 278 whereas in the case of AAderivatized ALCAR, first the molecule loses trimethylamine followed by loss of the ester group and rearrangement giving m/z 260. Further, a fragment with m/z 103 was obtained from the loss of the trimethylamine moiety (m/z 162−m/z 59=m/z 103) from the parent molecule, i.e., LCAR, which can be obtained by cleavage at the amide linkage of the AA-derivative followed by hydrolysis.

Similarly, by way of analogy with AA-derivatized LCAR, ALCAR gave rise m/z 204 corresponding to the molecular weight of ALCAR followed by loss of ester and rearrangement resulting in a molecular ion of m/z 85. The MS and MS/MS spectra of AA-derivatized methanolic extract were found to be in full agreement with the MS and MS/MS spectra of the AA-derivatized standards of LCAR and ALCAR which confirm the parallel fragmentation patterns in the samples obtained from the methanolic extract of seeds germinated under controlled conditions of oxygen and sucrose.

Figure 17:
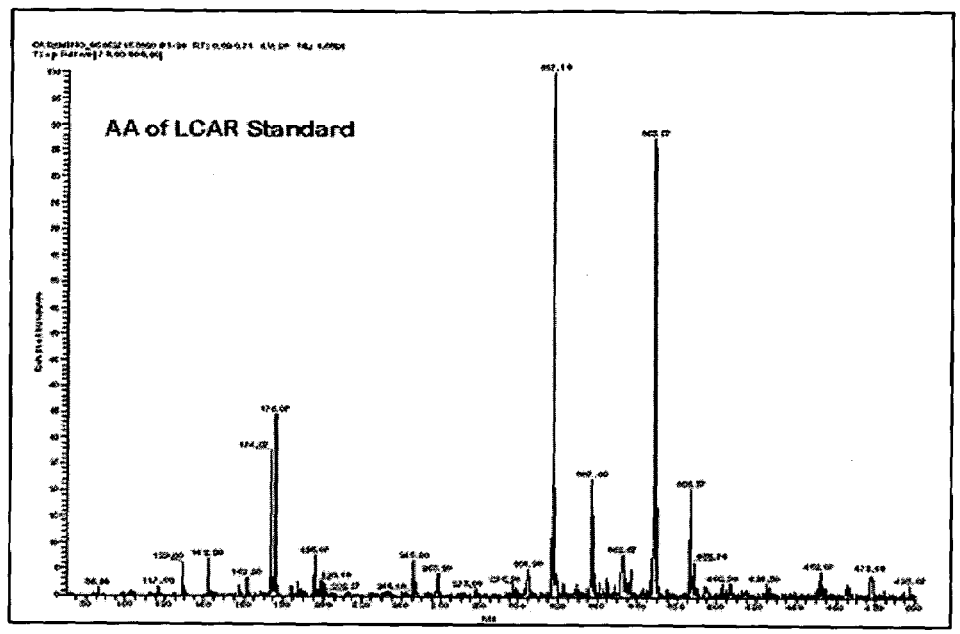
FIG. 17 is a block diagram illustrating mass spectra of AA derivatives of ALCAR.

FIG. 17 is a block diagram 72 illustrating mass spectra of AA derivatives of LCAR.

Figure 18:
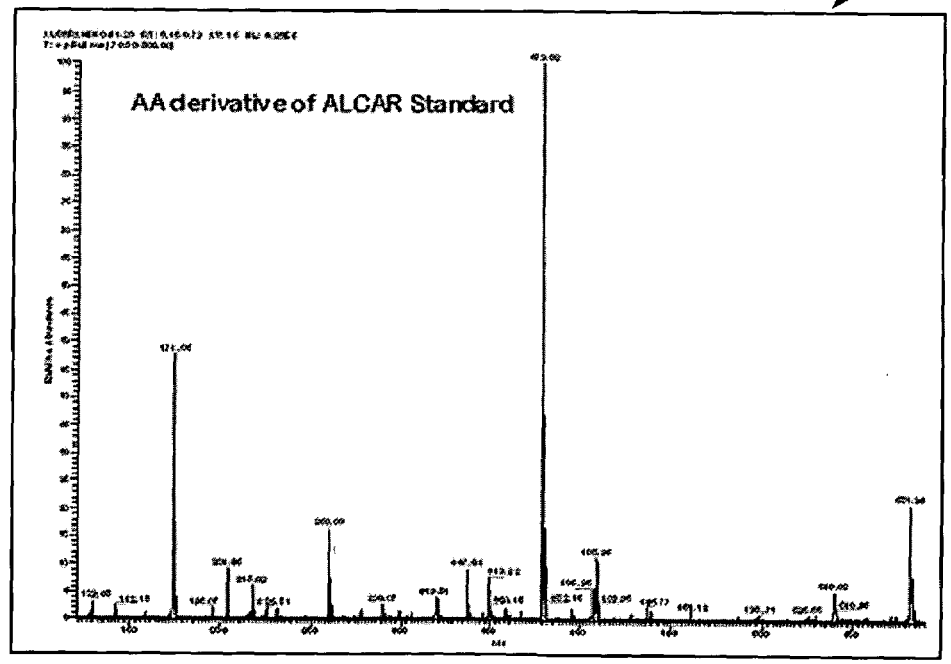
FIG. 18 is a block diagram illustrating 1H NMR spectra of a known concentration of ALCAR (1 mM) diluted 100-fold twice to obtain concentrations of 10:M and 100 nM, respectively.

FIG. 18 is a block diagram 74 illustrating mass spectra of AA derivatives of ALCAR.

Related mass fragmentation pattern studies of LCAR and ALCAR have been reported by Longo et al., (1996). NMR analytical methods are uniquely suited to follow the metabolite changes in sunflower seeds under different germination conditions and the following methods adapt existing NMR procedures to the analysis of sunflower seed metabolites.

The $_{31}P$ NMR procedure for PCA extracts has been previously described (Pettegrew et al., 1990; Klunk et al., 1994) and is now applied to sunflower seeds. Briefly, the analysis are conducted on a Bruker AM500 spectrometer operating at a field strength of 11.7 T for a $_{31}P$ observe frequency of 202.49 MHz. The extract sample (about 1.2 ml, pH adjusted to 8.5) is placed in a 10 mm microcell assembly and analyzed at 27/C while spinning at 20 Hz to enhance signal resolution. A single pulse followed by composite-pulse proton decoupling is used during data acquisition to remove dipolar coupling between phosphorus and proton nuclei. Typical experimental parameters are: 10:sec pulse (45° flip angle to prevent saturation of long relaxation time components); 2 sec repetition delay; 16-K data size; 8064-Hz sweep width and 20,000 acquisitions. In addition, a 2 Hz exponential digital filter is used before a Fourier transform.

The $_{31}P$ chemical shifts are reported relative to 85% orthophosphoric acid. Resonances were fitted with Lorenzian functions to obtain areas of the resonances. The total area of all resonances were set to 100% and the individual metabolites were quantified as a fraction of the total area to give mole %. The $_{31}P$ NMR spectra of PCA extracts of dry sunflower seeds was obtained at pH 8.5 and pH 9.8. At pH 8.5 the chemical-shift dispersion of phytic acid resonances from 1 to 3.5 ppm is optimized compared with the chemical-shift dispersion at pH 9.8. Subsequent $_{31}P$ NMR spectra for PCA extracts in this patent are reported at pH 8.5 instead of at pH 9.8 which is used for mammalian tissues that do not contain phytic acid.

The $_{31}P$ NMR procedure for Folch extracts has been previously described (Pettegrew et al., 2001) and applied to sunflower seeds. Briefly, the analysis are conducted on a Bruker AM500 spectrometer operating at a field strength of 11.7 T for a $_{31}P$ observe frequency of 202.49 MHz. The lipid samples are prepared for $_{31}P$ MRS analysis by resuspending the dried lipids in 3 ml of chloroform:methanol (2:1 v/v). Cs-EDTA (250:1) is added to this solution and chelates any cations in the sample. Deuterated benzene (250:1) is added to the sample to provide the MRS lock signal. The sample is analyzed under bi-level decoupling to maintain a constant Overhauser enhancement while spinning at 20 Hz to enhance signal resolution.

A single pulse sequence is used with a 45° pulse flip angle, 4K data points per free induction decay, 1000 Hz sweep width, a 4.1 s acquisition time giving a digital resolution of 0.45 Hz per point and a 2 s inter-pulse delay. In addition, a 0.2 Hz exponential multiplication line-broadening is applied to the free induction decay. The number of scans is 1000. $^1H$ NMR analyses are conducted on the PCA extracts at 500.13 MHz (11.7 T) at 27° C. LCAR and ALCAR spiking demonstrates resolution from choline in the TMA region.

Figure 19:
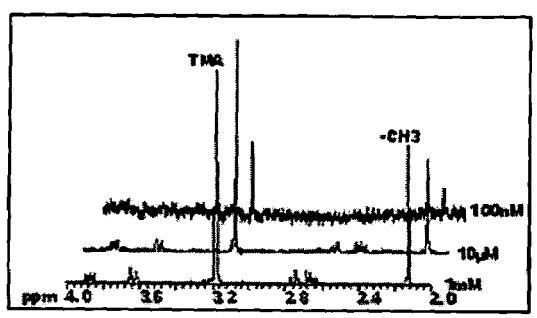
FIG. 19 is a block diagram HPLC of the methanolic extract of germinated seeds in high $O_2$/sucrose.

FIG. 19 is a block diagram 76 illustrating 1H NMR spectra of a known concentration of ALCAR (1 mM) diluted 100-fold twice to obtain concentrations of 10:M and 100 nM, respectively. The spectra were obtained with an identical number (e.g., 64) of acquisitions.

FIG. 19 shows the sensitivity of the NMR method to detect ALCAR. About 500:1 of sample dissolved in 99.8% $D_2O$ is placed in a 5 mm NMR tube and the pH adjusted to 5.2 to obtain optimum separation between various resonance peaks. NMR measurements involve a single pulse with solvent suppression by pre-saturating the water signal at very low decoupling radio-frequency power during the period of the repetition delay. Typical parameters are: 3:sec pulse (about 45° flip angle); 3.6 sec acquisition time; 2-sec repetition delay; 32-K data length; 5000 Hz sweep width; and 200 acquisitions for signal averaging. An exponential noise filter is used introducing 0.3 Hz line broadening before a Fourier transform. The $_1H$ NMR chemical shifts are reported relative to the trimethylsilylpropionic acid signal, which is assigned a chemical shift of 0.00 ppm. The resonances were quantified to give mole % values by the same method used for the $_{31}P$ NMR of PCA extracts.

The $_1H$ NMR analyses of the Folch extract are the same as those for the PCA extracts except for: $CDCl_3:CD_3OD$ (2:1) solvent; deuterated benzene for the NMR lock signal; 4-µsec pulse; 3.3 sec acquisition time; 5 sec inter-pulse delay; and 16 acquisition signal averaging. Data points are zero filled.

$_{13}C$ NMR analyses of Folch extracts are conducted at a $_{13}C$ observe frequency of 125.77 MHz (11.7 T). The samples are prepared for $_{13}C$ NMR analyses by dissolving the extract in a mixture of $CDCl_3:CD_3OD$ (2:1 v/v). $CDCl_3$ provides the NMR lock signal. A single pulse sequence followed by composite pulse decoupling during acquisition is used to acquire the free induction decay signal. Typical NMR acquisition parameters are: 4:sec pulse width (45 pulse flip angle); 64-K data points per free induction decay; 25000 Hz sweep width; 1.31 sec acquisition time giving a digital resolution of 0.73 Hz per point; a 10 sec inter-pulse delay; and 600 acquisitions for signal averaging. An external reference sample of 100 mM of PtdCho was used to determine the molarity of the naturally abundant $_{13}C$ in the NMR solvent chloroform. To obtain the absolute concentration of triacetyl glyceride (TAG), the area of the number 2 gylcerol carbon of TAG was compared with the area of the chloroform carbon, given the weight of the tissue extracted, the volume of the NMR sample, and that all of the extract was contained in the NMR sample.

HPLC of methanolic Soxhlet extraction of sunflower seeds demonstrated LCAR and ALCAR in seeds germinated under high $O_2$/Sucrose conditions as shown in FIG. 17.

Figure 20:
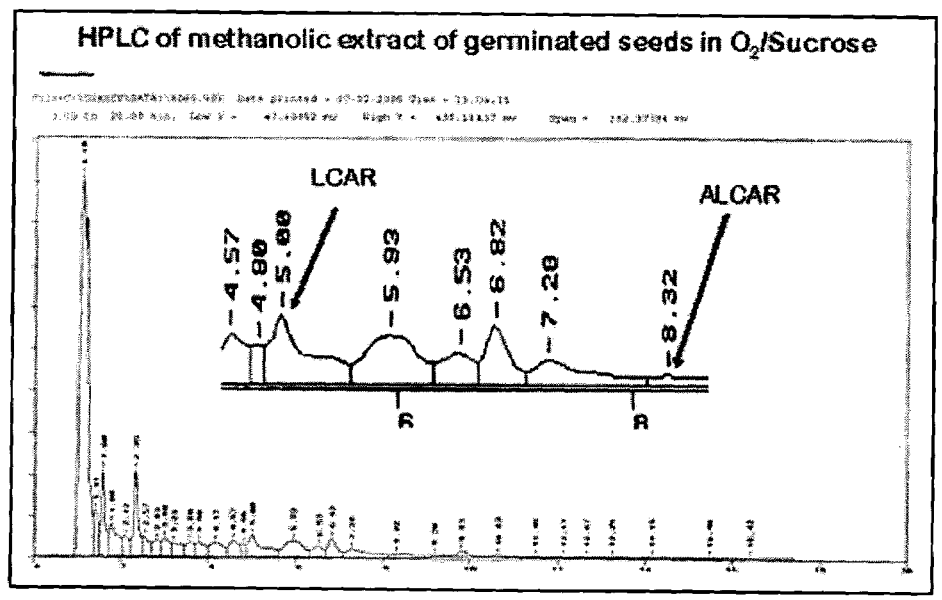
FIG. 20 is a block diagram illustrating Mass Spectrum of the derivatized methanolic extract of sunflower seeds germinated under high $O_2$/sucrose conditions.

FIG. 20 is a block diagram 78 HPLC of the methanolic extract of germinated seeds in high $O_2$/sucrose.

There was no detectable LCAR or ALCAR in the methanolic Soxhlet extraction under the following conditions: (1) air/sucrose; (2) air/no sucrose; or (3) high $O_2$/no sucrose.

Figure 21:
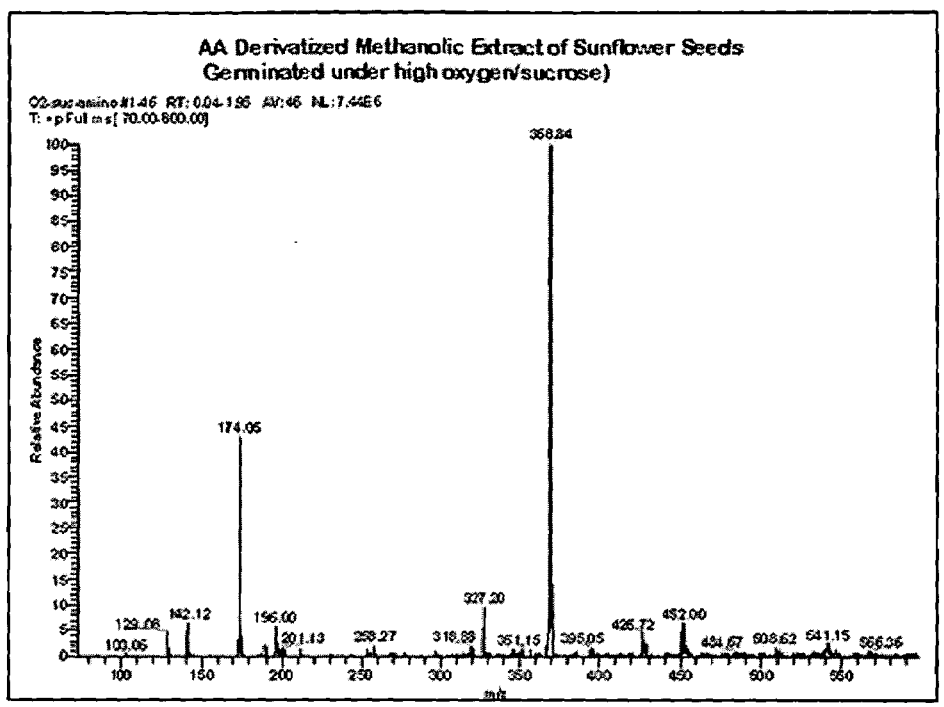
FIG. 21 is a block diagram illustrating Mass Fragmentation pattern of the methanolic extraction of sunflower seeds germinated under high $O_2$/sucrose conditions.

FIG. 21 is a block diagram 80 illustrating Mass Spectrum of the derivatized methanolic extract of sunflower seeds germinated under high $O_2$/sucrose conditions.

Figure 22:
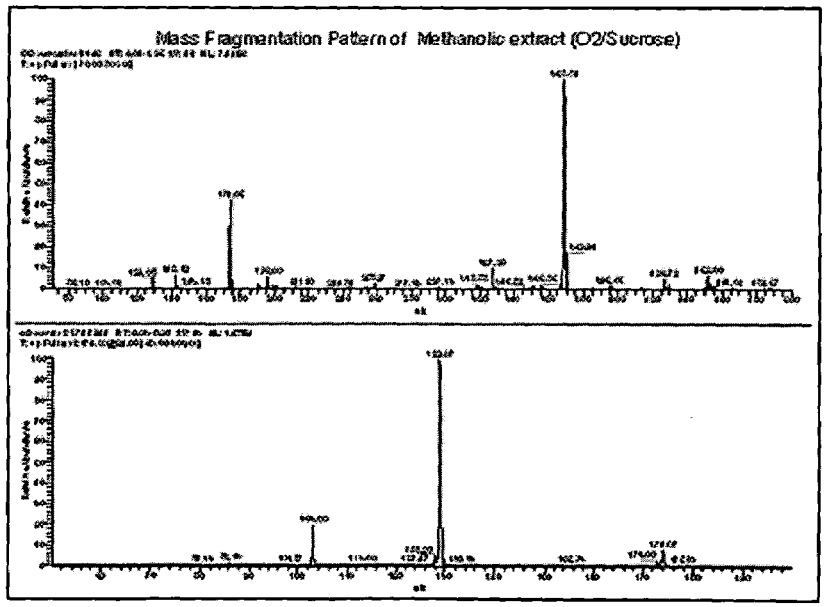
FIG. 22 is a block diagram illustrating $^{13}$C NMR of Folch 13C NMR of Folch extracts of sunflower seeds.

FIG. 22 is a block diagram 82 illustrating Mass Fragmentation pattern of the methanolic extraction of sunflower seeds germinated under high $O_2$/sucrose conditions.

Positive identification of the AA derivative of LCAR in the methanolic extract of sunflower seeds germinated under high $O_2$/sucrose conditions was provided by mass spectrometry (FIG. 21) and the mass fragmentation pattern of the same sample (FIG. 22).

Figure 23:
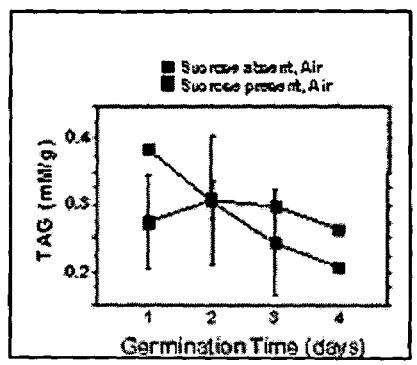
FIG. 23 is a block diagram illustrating $^{13}$C NMR of Folch 13C NMR of Folch extracts of sunflower seeds.
Figure 24:
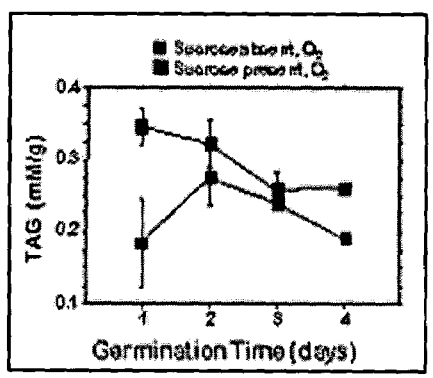
FIG. 24 is a block diagram illustrating $_{31}$P NMR of PCA extract of sunflower seeds.

Triacylglycerides (a storage form of fatty acids) are broken down more rapidly under certain conditions (sucrose plus $O_2$ incubation) in which fatty acid β-oxidation should be enhanced. Incubation in air without added sucrose (air minus sucrose) leads to decline in TAG levels from 0.38 mM/g to 0.20 mM/g over the 4-day incubation (FIG. 23). Under air plus sucrose conditions the levels of TAG remain at 0.28 mMig over the 4 days. Incubation under $O_2$ minus sucrose conditions leads to TAG levels 0.18 mM/g at day 1 with increases to 0.28 mM/g at day 2 and then down to 0.20 mM/g at day 4 (FIG. 24). $O_2$ plus sucrose incubation results in TAG levels of 0.35 mM/g at day 1, declining to 0.28 at day 4. Therefore, the levels of TAG start out higher under either air minus sucrose or $O_2$ plus sucrose conditions but drop to lower levels under air minus sucrose than under $O_2$ plus sucrose incubation.

The results of incubation in air and sucrose demonstrate that TAG catabolism by the glyoxylate cycle can be suppressed with sucrose inhibition of the cycle. The $O_2$ incubation studies demonstrate that TAG catabolism is greatest in $O_2$ minus sucrose which could be due to TAG fatty acids being metabolized by both the glyoxylate and mitochondrial routes. With addition of sucrose to $O_2$ incubation, the TAG levels go up because the glyoxylate pathway is now suppressed and the decline of TAG levels under these conditions ($O_2$ and sucrose) could be primarily via mitochondrial β-oxidation.

FIG. 23 is a block diagram 84 illustrating $^{13}$C NMR of Folch 13C NMR of Folch extracts of sunflower seeds with air.

FIG. 24 is a block diagram 86 illustrating $^{13}$C NMR of Folch 13C NMR of Folch extracts of sunflower seeds.

Figure 25:
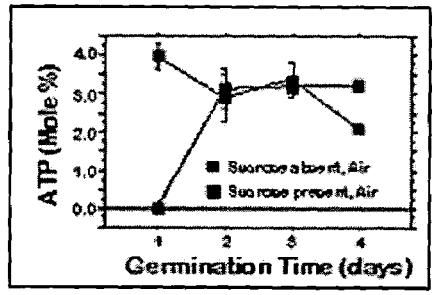
FIG. 25 is a block diagram illustrating $_{31}$P NMR of a PCA extract of sunflower seeds.

FIG. 25 is a block diagram 88 illustrating $_{31}$P NMR of PCA extract of sunflower seeds.

Figure 26:
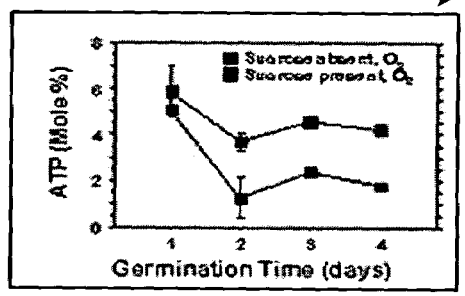
FIG. 26 is a block diagram illustrating $_{31}$P NMR of a PCA extract of sunflower seeds.

FIG. 26 is a block diagram 90 illustrating $_{31}$P NMR of a PCA extract of sunflower seeds.

Figure 27:
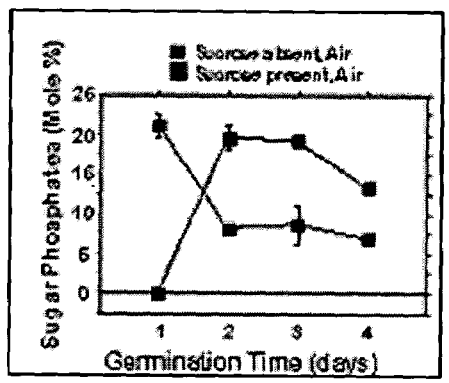
FIG. 27 is a block diagram illustrating $_{31}$P NMR of a PCA extract of sunflower seeds.

FIG. 27 is a block diagram 92 illustrating $_{31}$P NMR of a PCA extract of sunflower seeds.

Figure 28:
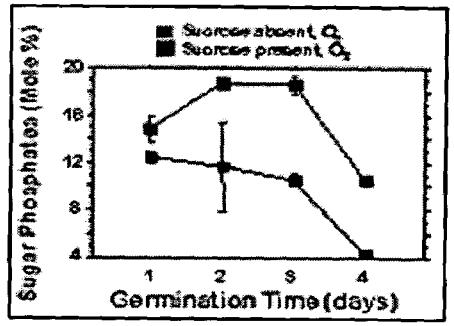
FIG. 28 is a block diagram illustrating $^{1}$H NMR of a PCA extract of sunflower seeds.

FIG. 28 is a block diagram 94 illustrating $_{31}$P NMR of a PCA extract of sunflower seeds.

Figure 29:
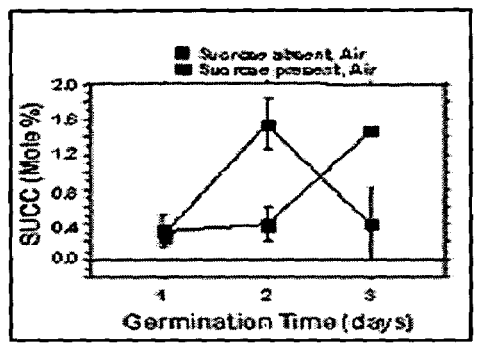
FIG. 29 is a block diagram illustrating $_{31}$P NMR of a PCA extract of sunflower seeds.

FIG. 29 is a block diagram 96 illustrating $^1$H NMR of a PCA extract of sunflower seeds.

Figure 30:
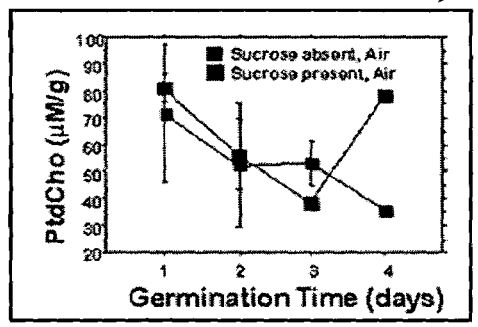
FIG. 30 is a block diagram illustrating $_{31}$P NMR of a PCA extract of sunflower seeds.

FIG. 30 is a block diagram 98 illustrating $_{31}$P NMR of a PCA extract of sunflower seeds.

Figure 31:
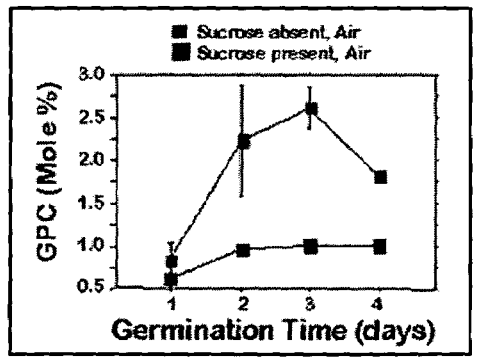
FIG. 31 is a block diagram illustrating $_{31}$P NMR of a PCA extract of sunflower seeds.

FIG. 31 is a block diagram 100 illustrating $_{31}$P NMR of a PCA extract of sunflower seeds.

Figure 32:
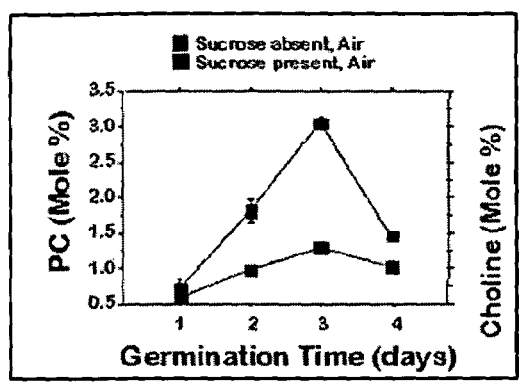
FIG. 32 is a block diagram illustrating $^{1}$H NMR of a PCA extract of sunflower seeds.

FIG. 32 is a block diagram 102 illustrating $_{31}$P NMR of a PCA extract of sunflower seeds.

Figure 33:
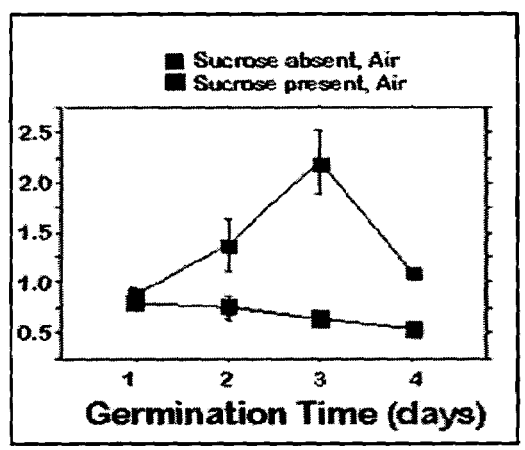
FIG. 33 is a block diagram illustrating $_{31}$P NMR of a PCA extract of sunflower seeds.

FIG. 33 is a block diagram 104 illustrating $^1$H NMR of a PCA extract of sunflower seeds.

Figure 34:
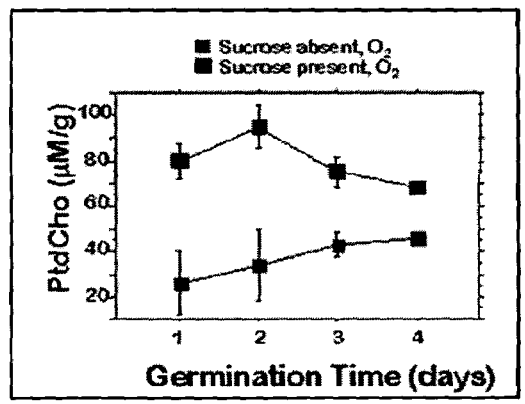
FIG. 34 is a block diagram illustrating $_{31}$P NMR of a PCA extract of sunflower seeds.

FIG. 34 is a block diagram 106 illustrating $_{31}$P NMR of a PCA extract of sunflower seeds.

Figure 35:
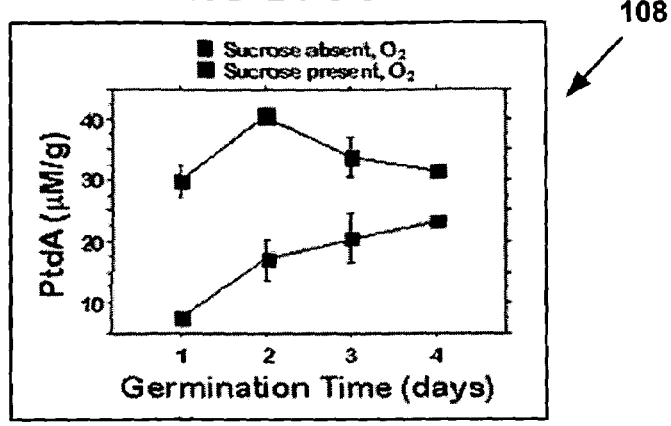
FIG. 35 is a block diagram illustrating $_{31}$P NMR of a PCA extract of sunflower seeds.

FIG. 35 is a block diagram 108 illustrating $_{31}$P NMR of a PCA extract of sunflower seeds.

Figure 36:
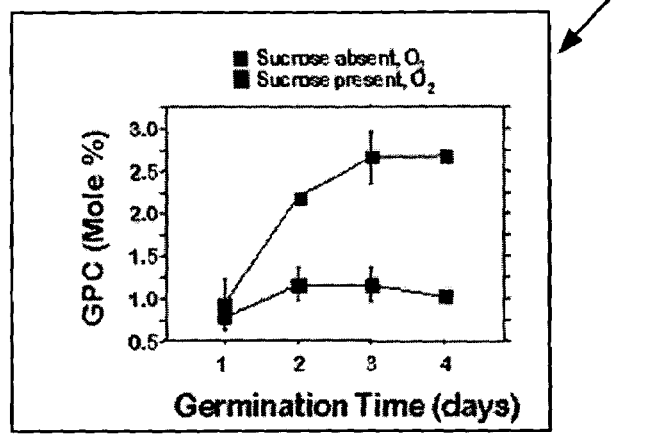
FIG. 36 is a block diagram illustrating $_{31}$P NMR of a PCA extract of sunflower seeds.

FIG. 36 is a block diagram 110 illustrating $_{31}$P NMR of a PCA extract of sunflower seeds.

Figure 37:
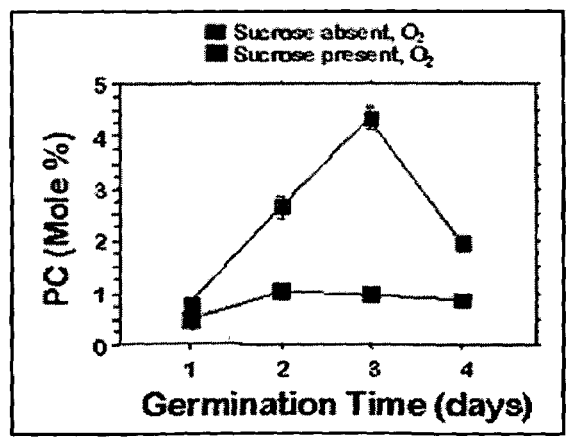
FIG. 37 is a block diagram illustrating $^{1}$H NMR of a PCA extract of sunflower seeds.

FIG. 37 is a block diagram 112 illustrating $_{31}$P NMR of a PCA extract of sunflower seeds.

Figure 38:
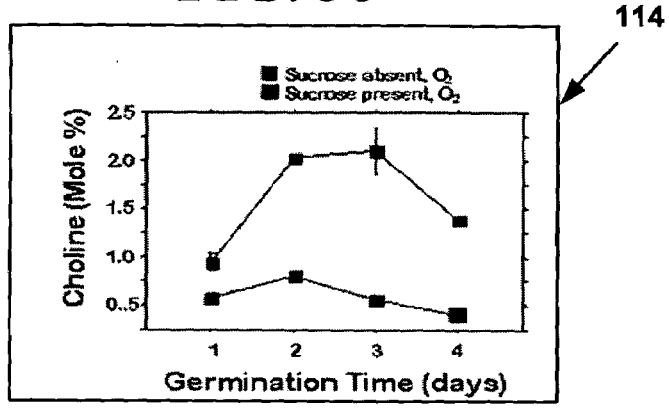
FIG. 38 is a block diagram illustrating $_{1}$H NMR of a PCA extract of sunflower seeds.

FIG. 38 is a block diagram 114 illustrating $^1$H NMR of a PCA extract of sunflower seeds.

Figure 39:
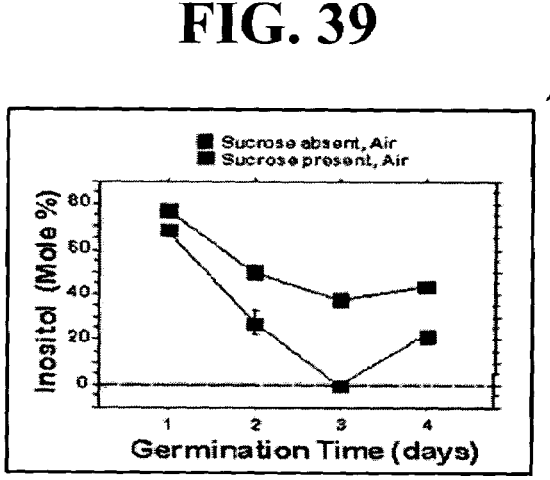
FIG. 39 is a block diagram illustrating $_{1}$H NMR of a PCA extract of sunflower seeds.

FIG. 39 is a block diagram 116 illustrating $_1$H NMR of a PCA extract of sunflower seeds.

Figure 40:
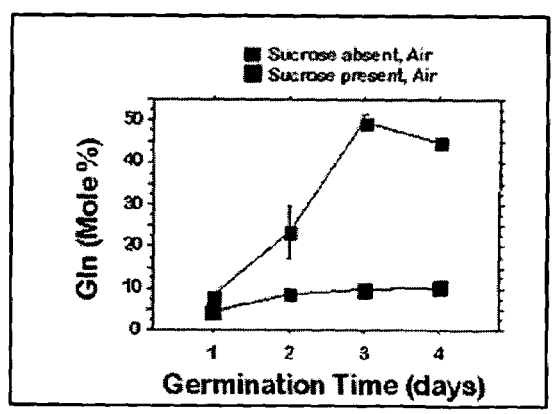
FIG. 40 is a block diagram illustrating $_{1}$H NMR of a PCA extract of sunflower seeds.

FIG. 40 is a block diagram 118 illustrating $_1$H NMR of a PCA extract of sunflower seeds.

Figure 41:
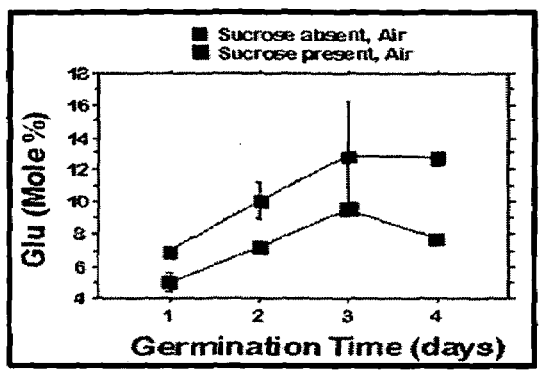
FIG. 41 is a block diagram illustrating $_{1}$H NMR of a PCA extract of sunflower seeds.

FIG. 41 is a block diagram 120 illustrating $_1$H NMR of a PCA extract of sunflower seeds.

Figure 42:
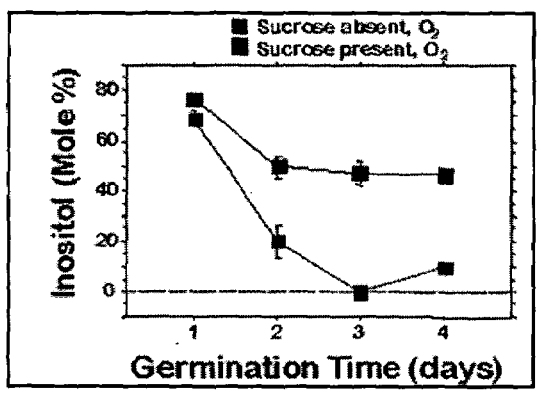
FIG. 42 is a block diagram illustrating $_{1}$H NMR of a PCA extract of sunflower seeds.

FIG. 42 is a block diagram 122 illustrating $_1$H NMR of a PCA extract of sunflower seeds.

Figure 43:
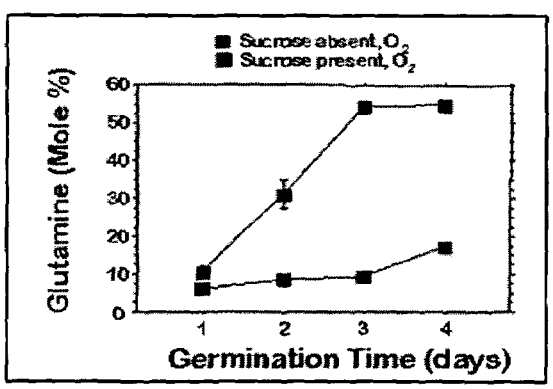
FIG. 43 is a block diagram illustrating $_{1}$H NMR of a PCA extract of sunflower seeds.

FIG. 43 is a block diagram 124 illustrating $_1$H NMR of a PCA extract of sunflower seeds.

Figure 44:
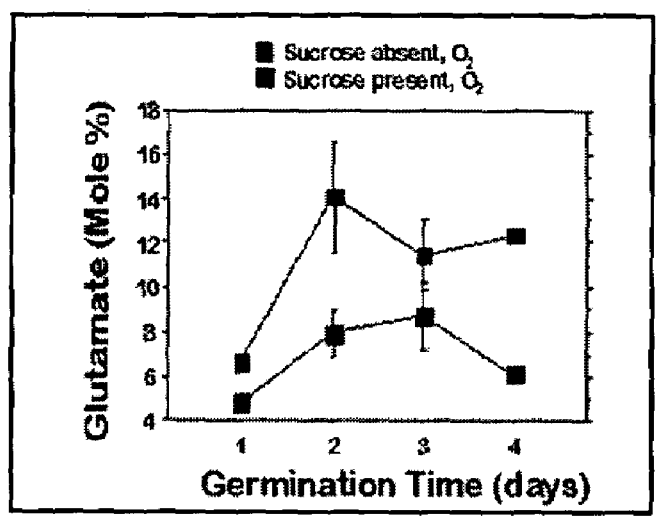
FIG. 44 is a block diagram illustrating $_{1}$H NMR of a PCA extract of sunflower seeds.

FIG. 44 is a block diagram 126 illustrating $_1$H NMR of a PCA extract of sunflower seeds.

Germination over a 4-day time period in air without added sucrose is associated with approximately a 2-fold reduction in the levels of ATP. The addition of sucrose leads to barely detectable ATP levels at day 1 with a 3-fold increase by day 2 which is maintained at day 4 (FIG. 24). Germination in the presence of 40% $O_2$ and sucrose yields higher ATP levels at all time points compared to incubation in air with or without added sucrose (FIG. 25).

Incubation in 40% $O_2$ without added sucrose yields ATP levels that start out at similar levels to those with added sucrose then drop to levels slightly below those obtained in air without sucrose (FIG. 26). These findings suggest that ATP levels are normally maintained in germinating sunflower seeds by the glyoxylate cycle. Inhibition of the glyoxylate cycle by sucrose initially depresses ATP levels which increase by 48 hours of germination possibly due to stimulation of fatty acid β-oxidation in the mitochondrial matrix by genome activation mechanisms. Stimulation of β-oxidation by $O_2$ and suppression of the glyoxylate cycle by sucrose results in the highest levels of ATP. The striking increase in ATP levels from 24 to 48 hours of incubation in air plus sucrose could reflect bioprocess engineering induced alterations in genomic activity resulting in enhanced ATP production by fatty acid β-oxidation in the mitochondria.

Sugar phosphate levels are high in seeds incubated for 24 hours in air without added sugar but then the levels drop greater than 50% by 48 hours with little further reductions. In contrast, sugar phosphate levels are barely detectable after 24 hours of incubation in air plus added sucrose then rise approximately 20 fold by 48 hours with reductions over the next two days (FIG. 27). These findings suggest that for the first 24 hours added sucrose can significantly suppress sugar-phosphate production via the glyoxylate cycle mediated gluconeogenesis, but by 48 hours sugar phosphate production exceeds that obtained by an unsuppressed glyoxylate cycle. Did the seeds "escape" from glyoxylate cycle suppression or are the sugar phosphates being produced by other pathways? Seeds incubated in $O_2$ plus sucrose have higher levels of sugar phosphate at all time points compared to seeds incubated in $O_2$ without added sucrose (FIG. 28).

This suggests that the combination of stimulation of respiration and inhibition of glyoxylate-mediated gluconeogenesis results in the highest levels of sugar phosphates. Some of the ATPs required for sugar phosphorylation under $O_2$ plus sucrose incubation conditions have been generated in the mitochondrial matrix by β-oxidation of fatty acids. Conditions that inhibit the glyoxylate cycle in plants would be expected to alter succinate levels which are a product of the cycle. Incubation in air in the absence of sucrose shows succinate levels to increase approximately 8-fold between days 1 and 2 of germination. This is in keeping with stimulation of the glyoxylate cycle during germination. By day 3 the succinate levels drop to approximately day 1 levels. Under air in the presence of sucrose incubation, conditions that should inhibit glyoxylate cycle activity, succinate levels remain low until day 3 when there is an approximate 7-fold increase. This suggests that by day 3 the seeds have "escaped" from sucrose inhibition of the glyoxylate cycle (FIG. 29) or that succinate is being produced by the TCA cycle which is activated by increased levels of acetyl-CoA generated by β-oxidation of fatty acids inside the mitochondrial matrix.

The latter explanation supports the hypothesis that inhibition of the glyoxylic cycle by sucrose levels leads to activation of genes responsible for LCAR production which leads to enhanced β-oxidation of fatty acids in the mitochondrial matrix. Incubation conditions that either stimulate respiration ($O_2$ in the absence of sucrose) or stimulate respiration and inhibit glyoxylate cycle ($O_2$ in the presence of sucrose) have little effect on succinate levels (not shown).

Germination in air without added sucrose is associated with breakdown of phosphatidylcholine (FIG. 30) to yield glycerophosphocholine (FIG. 31) which can be further broken down by phosphodiester-phosphodiesterases to phosphocholine (FIG. 31) plus glycerol or "-glycerolphosphate plus choline (FIG. 32). Incubation of seeds in air plus sucrose decreases the production of GPC, PC, and choline with apparent increase in PtdCho at day 4 of incubation. These findings suggest that sucrose inhibition of the glyoxylate pathway reduces the breakdown of the membrane phospholipid PtdCho as evidenced by decreased levels of GPC, PC, and choline. Germination in the presence of 40% $O_2$ without added sucrose demonstrates increases in the levels of PtdCho (FIG. 34) and PtdA (FIG. 35) and slight increases in PtdCho breakdown products (GPC) (FIG. 36) with concomitant increases in PC (FIG. 37) and choline (FIG. 38).

Germination in the presence of 40% $O_2$ plus sucrose results in increased levels of PtdCho and PtdA at all time points compared to incubation without sucrose (FIGS. 34 and 35) with some reduction in the levels over the 4 days. Under the same 40% $O_2$ plus sucrose conditions, GPC, PC, and choline levels are reduced compared to no added sucrose with only slight changes (±) over the 4-day period. A possible explanation for the increased levels of PtdCho and PtdA along with decreased levels of PtdCho breakdown products (GPC, PC, choline) under conditions of glyoxylate cycle suppression (plus sucrose) and mitochondrial respiration stimulation (plus $O_2$) is that with increased β-oxidation of TAG-derived fatty acids in the mitochondria there would be less need for production of fatty acids (via phospholipase $A_1$ and $A_2$) from PtdCho and PtdA.

Germination in air without added sucrose decreases myo-inositol levels (FIG. 39) and increases in glutamine (FIG. 40) and glutamate (FIG. 41) levels which are blunted by the addition of sucrose. The initial high levels of myo-inositol under air (-sucrose) incubation could reflect the breakdown of phytic acid to myo-inositol since phytic acid levels are barely detectable at day 1. The further drop in myo-inositol levels could reflect conversion of myo-inositol into myo-inositol phosphate (i.e., sugar phosphates) but this is not likely as sugar phosphate levels drop under these same conditions (FIG. 27). "-Ketoglutamate generated by the TCA cycle can be converted to glutamate and glutamine. Sucrose inhibition of glyoxyate cycle-driven TCA would be expected to decrease glutamate and glutamine synthesis as is shown. Germination in the presence of 40% $O_2$ without added sucrose results in myo-inositol levels dramatically decreasing (FIG. 42) with dramatic increases in glutamine (FIG. 43) and lesser increases in glutamate (FIG. 44).

Addition of sucrose to the 40% $O_2$ incubation conditions significantly blunts the fall in myoinositol and the elevations in glutamine and glutamate. Inhibition of the glyoxylate cycle (air plus sucrose) and stimulation of β-oxidation ($O_2$ plus sucrose) both slow the breakdown of myo-inositol. Since glyoxylate cycle inhibition and mitochondrial respiration stimulation both should enhance fatty acid mitochondrial β-oxidation, the excess ATP produced by β-oxidation could be stored as phosphorylated myo-inositol; these same incubation conditions elevate sugar phosphate levels.

Acetyl-L-carnitine (ALCAR) and L-camtine (LCAR) are nutraceuticals with indications in treating a variety of mental health disorders including Alzheimer's disease, geriatric depression, and schizophrenia. A metabolomics-guided bioprocess method is presented to enhance aLCAR and LCAR formation in germinating plant seeds. Metabolic fluxes are manipulated by germination in bioreactors to increase oxygen availability as well as provide an aseptic environment to alter carbohydrate consumption and feedback repress gluconeogenesis. Large shifts in sunflower seed fatty acid, phospholipid and high-energy metabolism change the germination environment and these metabolic changes lead to an approximate 1000-fold increase in natural LCAR and ALCAR production by the seeds. The resulting LCAR and ALCAR products from the seeds are used for treating mental health disorders.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

It should be understood that the architecture, programs, processes, methods and systems described herein are not related or limited to any particular type of component, composition, compound, concentration, pressure or temperature and other components, compositions, compounds, concentrations, pressures or temperatures can be used to practice the invention. Various types of general purpose or specialized components, compositions, compounds, concentrations, pressures or temperatures may be used with or perform operations in accordance with the teachings described herein.

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more or fewer elements may be used in the block diagrams.

The claims should not be read as limited to the described order or elements unless stated to that effect. In addition, use of the term "means" in any claim is intended to invoke 35 U.S.C. §112, paragraph 6, and any claim without the word "means" is not so intended.

Therefore, all embodiments that come within the scope and spirit of the following claims and equivalents thereto are claimed as the invention.

We claim:

1. A method for producing a pharmaceutical composition comprising:
  i) a manipulated germination process wherein a sucrose controlled and oxygen controlled environment are applied to a plurality of germinating sunflower seeds to enhance the generation of a metabolite selected from L-camitine (LCAR), acetyl-L-camitine (ALCAR) and combinations thereof wherein the oxygen controlled environment includes at least 40% $O_2$;

ii) isolating said metabolite therefrom by solvent extraction; and iii) mixing said metabolite with one or more pharmaceutically acceptable carriers or excipients.

2. A method for producing L-carnitine (LCAR) and acetyl-L-carnitine (ALCAR), comprising:

i) enhancing fatty acid β-oxidation with sucrose suppression of a plurality of germinating sunflower seeds; and ii) stimulating β-oxidation of the fatty acids in the plurality of sunflower seeds with an oxygen enhanced environment for a pre-determined time period, wherein the oxygen enhanced environment comprises at least 40% $O_2$, thereby enhancing LCAR and/or ALCAR synthesis in the plurality of germinating sunflower seeds.

3. The method of claim 2 further comprising: extracting LCAR and ALCAR from the plurality of germinating sunflower seeds by contacting said seeds with an organic solvent.

4. The method of claim 3 wherein the step of extracting LCAR and ALCAR from the plurality of germinating sunflower seeds comprises contacting said seeds with an organic solvent or solvents selected from the group consisting of hexane, methylene chloride and methyl alcohol.

5. The method of claim 4 further comprising contacting said extracted LCAR and ALCAR with a pharmaceutically acceptable carrier(s) or excipient(s) to generate a pharmaceutically acceptable composition suitable for human consumption.

6. A method for producing L-carnitine (LCAR) and/or acetyl-L-carnitine (ALCAR), comprising:

i) enhancing fatty acid β-oxidation with sucrose suppression of a plurality of glycoxylate cycles in a plurality of germinating sunflower seeds over a pre-determined time period; and ii) stimulating β-oxidation of the fatty acids in the plurality of sunflower seeds with $O_2$ for a pre-determined time period, wherein the $O_2$ enhanced environment comprises at least 40% $O_2$, thereby enhancing LCAR and/or ALCAR synthesis in the plurality of germinating sunflower seeds.

* * * * *